United States Patent
Yu et al.

(10) Patent No.: US 12,427,211 B2
(45) Date of Patent: Sep. 30, 2025

(54) PEPTIDE-UREA DERIVATIVE, PHARMACEUTICAL COMPOSITION CONTAINING SAME AND APPLICATION THEREOF

(71) Applicant: Bivision Pharmaceuticals, Inc., Jiangsu (CN)

(72) Inventors: Haihua Yu, Jiangsu (CN); Eric Yanjun Wang, Jiangsu (CN); Kevin Yu Wang, Jiangsu (CN)

(73) Assignee: Bivision Pharmaceuticals, Inc., Nanjing (CN)

( * ) Notice: Subject to any disclaimer, the term of this patent is extended or adjusted under 35 U.S.C. 154(b) by 0 days.

(21) Appl. No.: 18/776,861

(22) Filed: Jul. 18, 2024

(65) Prior Publication Data

US 2024/0366813 A1     Nov. 7, 2024

Related U.S. Application Data

(63) Continuation of application No. 18/688,290, filed as application No. PCT/CN2022/116897 on Sep. 2, 2022.

(30) Foreign Application Priority Data

Sep. 3, 2021 (CN) .......................... 202111031423.6

(51) Int. Cl.
*A61K 51/08* (2006.01)
*A61K 47/18* (2017.01)
*A61K 47/22* (2006.01)

(52) U.S. Cl.
CPC .......... *A61K 51/088* (2013.01); *A61K 47/183* (2013.01); *A61K 47/22* (2013.01); *A61K 2121/00* (2013.01)

(58) Field of Classification Search
None
See application file for complete search history.

(56) References Cited

U.S. PATENT DOCUMENTS

| | | | |
|---|---|---|---|
| 10,406,240 B2 | 9/2019 | Low et al. | |
| 11,045,564 B2 | 6/2021 | Eder et al. | |
| 12,128,114 B2 * | 10/2024 | Ferro Flores | ........... C07F 5/003 |
| 2002/0147997 A1 * | 10/2002 | Turner | ................... A61K 38/13 424/9.1 |
| 2013/0034494 A1 | 2/2013 | Babich et al. | |
| 2019/0343970 A1 * | 11/2019 | Ferro Flores | ......... C07F 13/005 |
| 2021/0220493 A1 | 7/2021 | Pomper et al. | |
| 2022/0105194 A1 * | 4/2022 | Akaiwa | .............. A61K 51/1045 |

FOREIGN PATENT DOCUMENTS

| | | |
|---|---|---|
| CN | 105636924 A | 6/2016 |
| CN | 109641924 A | 4/2019 |
| CN | 110740757 A | 1/2020 |
| CN | 111253465 A | 6/2020 |
| CN | 111491668 A | 8/2020 |
| CN | 111630059 A | 9/2020 |
| CN | 112074526 A | 12/2020 |
| CN | 112770785 A | 5/2021 |
| CN | 112898270 A | 6/2021 |
| CN | 113004371 A | 6/2021 |
| EP | 3766893 A1 | 1/2021 |
| EP | 4227315 A1 | 8/2023 |
| EP | 4397322 A1 | 7/2024 |
| WO | 2002098885 A1 | 12/2002 |
| WO | 2015171792 A1 | 11/2015 |
| WO | 2016062370 A1 | 4/2016 |
| WO | 2018108287 A1 | 6/2018 |
| WO | 2020220023 A1 | 10/2020 |
| WO | 2021013978 A1 | 1/2021 |
| WO | 2021168028 A1 | 8/2021 |
| WO | 2022101352 A1 | 5/2022 |
| WO | 2022126275 A1 | 6/2022 |
| WO | 2022253785 A2 | 12/2022 |

(Continued)

OTHER PUBLICATIONS

Chinese International Search Report mailed on Dec. 2, 2022 in PCT/CN2022/116897.
Chinese Written Opinion mailed on Dec. 2, 2022 in PCT/CN2022/116897.
English translation of International Search Report mailed on Dec. 2, 2022 in PCT/CN2022/116897.
English translation of Written Opinion mailed on Dec. 2, 2022 in PCT/CN2022/116897.
L Greifenstein et al., "Synthesis, labeling and preclinical evaluation of a squaric acid containing PSMA-inhibitor labeled with 68Ga—a comparison with PSMA-11 and PSMA-617," copyright 2019, ChemMedChem 10.1002/cmdc.201900559, pp. 1-12.

(Continued)

*Primary Examiner* — Michael G. Hartley
*Assistant Examiner* — Kaila A Craig
(74) *Attorney, Agent, or Firm* — Fox Rothschild LLP

(57) ABSTRACT

A peptide-urea derivative, a pharmaceutical composition containing same and an application thereof are provided, the derivative being as shown in formula I. The derivative can be used for preoperative imaging diagnosis and grading of PSMA-positive prostate cancer, and can also be used for the treatment of various types and stages of prostate cancer, achieving the integration of diagnosis and treatment, and having broad application prospects.

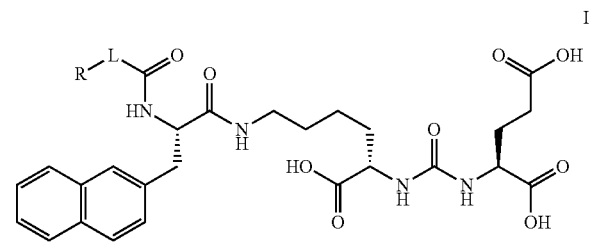

16 Claims, 12 Drawing Sheets

(56) References Cited

FOREIGN PATENT DOCUMENTS

| WO | 2023030434 A1 | 3/2023 |
| WO | 2023083209 A1 | 5/2023 |

OTHER PUBLICATIONS

Claus Zippel et al., "Current Status of PSMA-Radiotracers for Prostate Cancer: Data Analysis of Prospective Trials Listed on ClinicalTrials.gov," copyright 2020, Pharmaceuticals, vol. 13, No. 12, doi:10.3390/ph13010012, pp. 1-13.

Frederik L. Giesel et al., "F-18 labelled PSMA-1007: biodistribution, radiation dosimetry and histopathological validation of tumor lesions in prostate cancer patients," copyright 2016, Eur J Nucl Med Mol Imaging, vol. 44, DOI 10.1007/s00259-016-3573-4, pp. 678-688.

Klaus Kopka et al., "Glu-Ureido-Based Inhibitors of Prostate-Specific Membrane Antigen: Lessons Learned During the Development of a Novel Class of Low-Molecular-Weight Theranostic Radiotracers," copyright 2017, J Nucl Med, vol. 58, DOI: 10.2967/jnumed. 116. 186775, pp. 17S-26S.

Nasim Vahidfar et al., "Historical review of pharmacological development and dosimetry of PSMA-based theranostics for prostate cancer," copyright 2019, Journal of Radioanalytical and Nuclear Chemistry, Akadémiai Kiadó, Budapest, Hungary 2019, published online Sep. 2019, https://doi.org/10.1007/s10967-019-06800-6, pp. 1-12.

Martina Benesova et al., "Linker Modification Strategies To Control the Prostate-Specific Membrane Antigen (PSMA)—Targeting and Pharmacokinetic Properties of DOTA-Conjugated PSMA Inhibitors," copyright 2016, J. Med. Chem., vol. 59, DOI: 10.1021/acs.jmedchem.5b01210, pp. 1761-1775.

Martina Weineisen et al., "68Ga- and 177Lu-Labeled PSMA I&T: Optimization of a PSMA-Targeted Theranostic Concept and First Proof-of-Concept Human Studies," copyright 2015, J. Nucl. Med., vol. 56, DOI: 10.2967/jnumed.115.158550, pp. 1169-1176.

Martina Benesova et al., "Albumin-Binding PSMA Ligands: Optimization of the Tissue Distribution Profile," copyright date unknown, Mol. Pharmaceutics, DOI: 10.1021/acs.molpharmaceut.7b00877, pp. A-M.

Zhantong Wang et al., "Single Low-Dose Injection of Evans Blue Modi?ed PSMA-617 Radioligand Therapy Eliminates Prostate-Specific Membrane Antigen Positive Tumors," copyright date unknown, Bioconjugate Chem., DOI: 10.1021/acs.bioconjchem.8b00556, pp. A-I.

Greifenstein et al., "Synthesis, labeling and preclinical evaluation of a squaric acid containing PSMA-inhibitor labeled with 68Ga—a comparison with PSMA-11 and PSMA-617", Feb. 14, 2020, ChemMedChem 10.1002/cmdc.201900559.

Zippel et al., "Current Status of PSMA-Radiotracers for Prostate Cancer: Data Analysis of Prospective Trials Listed on ClinicalTrials.gov", copyright 2020, Jan. 13, 2020, Pharmaceuticals, vol. 13, No. 12; DOI:10.3390/ph13010012.

Giesel et al., "F-18 labelled PSMA-1007: biodistribution, radiation dosimetry and histopathological validation of tumor lesions in prostate cancer patients", published online Nov. 26, 2016, Eur J Nucl Mol Imaging, vol. 44, pp. 678-688, DOI:10.1007/s00259-016-3573-4.

Kopka et al., "Glu-Ureido-Based Inhibitors of Prostate-Specific Membrane Antigen: Lessons Learned During the Development of a Novel Class of Low-Molecular-Weight Theranostic Radiotracers", copyright 2017, Sep. 2017, J Nucl Med, vol. 58, pp. 17S-26S, Doi: 10.2967/jnumed.116.186775.

Vahidfar et al., "Historical review of pharmacological development and dosimetry of PSMA-based theranostics for prostate cancer", copyright 2019, Sep. 24, 2019, Journal of Radioanalytical and Nuclear Chemistry, https://doi.org/10.1007/s10967/019-06800-6.

Benesova et al., "Linker Modification Strategies To Control the Prostate-Specific Membrane Antigen (PSMA)—Targeting and Pharmacokinetic Properties of DOTA-Conjugated PSMA Inhibitors", copyright 2016, Feb. 15, 2016, J. Med. Chem., vol. 59, pp. 1761-1775, DOI: 10.1021/acs.jmedchem.5b01210.

Weineisen et al., "68Ga- and 177Lu-Labeled PSMA I&T: Optimization of a PSMA-Targeted Theranostic Concept and First Proof-of-Concept Human Studies", copyright 2015, Published online Jun. 18, 2015. J Nucl Med, vol. 56, pp. 1169-1176, DOI: 10.2967/jnumed. 115.158550.

Benesova et al., "Albumin-Binding PSMA Ligands: Optimization of the Tissue Distribution Profile", Feb. 5, 2018, Mol. Pharmaceutics, DOI: 10.1021/acs.molpharmaceut.7b00877.

Wang et al., "Single Low-Dose Injection of Evans Blue Modified PSMA-617 Radioligand Therapy Eliminates Prostate-Specific Membrane Antigen Positive Tumors", Aug. 14, 2018, Bioconjugate Chem., DOI: 10.1021/acs.bioconjchem.8b00556.

English translation of International Search Report and Written Opinion mailed on Dec. 2, 2022 in PCT/CN2022/116897.

English translation of First Office Action mailed on May 1, 2024 in CN Application No. 202211073924.5.

Extended European Search Report mailed on Jul. 25, 2025 in European Patent Application No. 22863643.7.

\* cited by examiner

1 H  5 H  24 H  48 H  72 H

¹⁷⁷Lu-E16

177Lu-E18

PEPTIDE-UREA DERIVATIVE, PHARMACEUTICAL COMPOSITION CONTAINING SAME AND APPLICATION THEREOF

This application is a continuation application of U.S. patent application Ser. No. 18/688,290, which is the U.S. national phase of International Patent Application No. PCT/CN2022/116897 filed on Sep. 2, 2022, which claims the priority of Chinese patent application No. 202111031423.6 filed on Sep. 3, 2021. This application cites the full text of the above-mentioned patent applications.

TECHNICAL FIELD

The present disclosure relates to a peptide-urea derivative, pharmaceutical composition containing the same and use thereof.

BACKGROUND OF THE INVENTION

According to the report "Global Cancer Statistics 2018," published online in the A Cancer Journal for Clinicians, the official journal of the American Cancer Society, an assessment of the incidence and mortality of 36 cancers in 185 countries found that: prostate cancer is the second most common cancer in men, after lung cancer. The "Cancer Statistics 2018" report in the United States predicts that the incidence of prostate cancer in American men accounts for about 19% of the incidence of tumors, ranking first. According to the "national cancer statistics 2014" released by the National Cancer Center of China, the incidence of prostate cancer in Chinese men is 3.25%, ranking sixth, but it has gradually increased in recent years. Therefore, either in the world or in China, prostate cancer is a high incidence of cancer.

Early imaging diagnosis and treatment of prostate cancer has become an urgent problem to be solved in China and in the whole world. Prostate cancer begins in the tissue surrounding the prostate, and as it grows, it gradually spreads to other vital organs such as the lung and bone. In the early stage, there is no obvious symptom, but as the prostate cancer grows, it can cause problems such as urethral compression and urinary tract obstruction, and further spread to the spine or pelvis. For the diagnosis of prostate cancer, imaging diagnostic methods such as SPECT (Single Photon Emission Computed Tomography) or PET (Positron Emission Tomography) has been used % currently, wherein the principle is to label PSMA-targeted polypeptide substances with radioactive isotopes emitting γ-rays or positrons, and then display the presence and distribution of tumor cells in tomographic images and three-dimensional images through prostate cancer-specific targeted distribution. These diagnostic imaging methods have recently been widely used due to the dramatic improvement in image quality via the development of SPECT-CT/MRI and PET-CT/MRI that combine CT and MRI with SPECT or PET. The radiopharmaceuticals currently used for prostate cancer-specific imaging use PSMA specific ligands as targeting vectors, which can bind to the protein PSMA (prostate-specific membrane antigen) specifically expressed in prostate cancer. PSMA is a type II transmembrane glycoprotein, also known as glutamic acid carboxypeptidase, which is a specific molecular marker of prostate cancer. It is expressed in a very small amount in kidney, small intestine, and brain tissue, and the expression level in tumor tissue is much higher than the expression in normal tissues. A representative ligand of PSMA is a peptide derivative such as Glu-urea-Lys (GUL) or Glu-urea-Cys (GUC). Therefore, by labeling radioactive isotopes to ligands containing this peptide structure, the resulting radiopharmaceuticals can be used for PET or SPECT imaging of prostate cancer, or for the treatment of prostate cancer (MEder, et al., Bioconjugate Chem 2012, 23:688-697). The radioisotopes used for labeling peptides are mainly α-ray-emitting radionuclides, β-ray-emitting radionuclides, γ-ray-emitting radionuclides, and positron beam-emitting radionuclides. Among the radioisotopes, α-ray-emitting radionuclides and β-ray-emitting radionuclides are used for therapy, and γ-ray-emitting radionuclides and positron beam-emitting radionuclides are used for diagnosis by nuclear imaging. There are generally two methods for radioactive isotope labeling of ligands: the method of directly attaching the ligand to the radioisotope, or the method of chelating the radioisotope by the ligand through bifunctional chelating agents (BFCA) such as DTPA, DOTA, TETA, HYNIC, N2S2, and MAG3. The direct attaching method is mainly used for the labeling of various non-metallic radioactive isotopes such as 125I and 131I. The method using a bifunctional chelating agent (BFCA) is mainly used for the labeling of various metal radioisotopes, and the type of a bifunctional chelating agent (BFCA) can be selected according to the properties of the ligand and the radioisotope.

At present, castration surgery, anti-androgen castration method, and androgen receptor inhibitor are the mainstream treatment options for prostate cancer. Although these treatment options are very effective in the initial stage, a large proportion of patients will develop castration resistant prostate cancer (CRPC for short), or even metastatic castration resistant prostate cancer (mCRPC). mCRPC is a disease with limited treatment options and significant unmet medical needs, so radiopharmaceuticals targeting PSMA have become a research hotspot in recent years.

A series of clinical studies have been conducted using PSMA-targeted radiopharmaceuticals to treat mCRPC patients. Although the initial clinical results of radiopharmaceuticals such as $^{177}$Lu-PSMA-617 and $^{177}$Lu-PSMA I&T are encouraging, but there are some problems, for example, nearly 30% of patients do not respond to this treatment method. One possible explanation is that not enough radiopharmaceuticals are delivered to the tumor lesion due to unsatisfactory pharmacokinetics. Another concern is the long-term accumulation of radiopharmaceuticals such as $^{177}$Lu-PSMA-617 in kidneys, salivary glands and other organs. Therefore, a radiopharmaceutical with high activity, high selectivity and better pharmacokinetics targeting PSMA is a continuous hotspot in the field of treatment and diagnosis of mCRPC.

SUMMARY OF THE INVENTION

The technical problem to be solved by the present disclosure is lack of structural diversity in the existing peptide-urea derivatives, and the uptake and too long residence time of the radiopharmaceuticals prepared by the existing peptide-urea derivatives in the kidney and other organs may cause potential harm to the human body, while the retention time of the radiopharmaceuticals on the targeted tumor cells is not long enough. To this end, the present disclosure provides a peptide-urea derivative, a pharmaceutical composition containing the same and the use thereof. The disclosed derivative has better chemical and biological properties than other similar peptide-urea derivatives known so far, and the uptake and residence time on non-target organs such as kidneys are greatly reduced, while the uptake and retention time on target cells are significantly increased. The derivative can be used not only for the imaging diagnosis and grading of PSMA-positive prostate cancer before surgery, but also for the treatment of various types and stages of prostate cancer, achieving the integration of diagnosis and treatment. The derivative has a wide application prospect.

The present disclosure provides a peptide-urea derivative of formula I, a pharmaceutically acceptable salt thereof, a solvate thereof or a solvate of a pharmaceutically acceptable salt thereof;

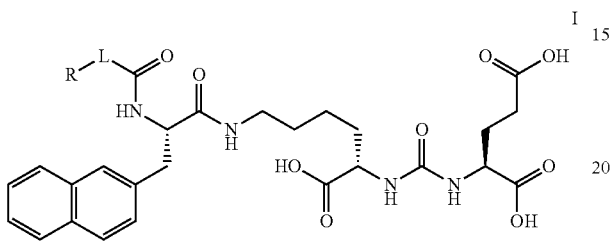

I wherein L is -$L^1$-$L^2$- or -$L^3$-$L^4$-$L^5$-.

$L^1$ is a 5-12 membered carbon heterocyclic ring, a 5-12 membered heteroaromatic ring, a 5-12 membered carbon heterocyclic ring substituted by $R^{1-1}$ or a 5-12 membered heteroaromatic ring substituted by $R^{1-2}$; in the above-mentioned carbon heterocyclic ring, the number of heteroatoms is 1, 2 or 3, and the heteroatoms are selected from one or more of N, O and S; in the above-mentioned heteroaromatic ring, the number of heteroatoms is 1, 2 or 3, and the heteroatoms are selected from one or more of N, O and S; $R^{1-1}$ and $R^{1-2}$ are independently F, Cl, Br or $C_1$-$C_3$ alkyl; and the $L^1$ is linked to R through a N atom;

$L^2$ is a bond, a 5-12 membered carbocyclic ring, a 5-12 membered carbon heterocyclic ring, a 6-14 membered aromatic ring, a 5-12 membered heteroaromatic ring, a 5-12 membered carbocyclic ring substituted by $R^{2-1}$, a 5-12 membered carbon heterocyclic ring substituted by $R^{2-2}$, a 6-14 membered aromatic ring substituted by $R^{2-3}$ or a 5-12 membered heteroaromatic ring substituted by $R^{2-4}$; in the carbon heterocyclic ring, the number of heteroatoms is 1, 2 or 3, and the heteroatoms are selected from one or more of N, O and S; in the heteroaromatic ring, the number of heteroatoms is 1, 2 or 3, and the heteroatoms are selected from one or more of N, O and S; $R^{2-1}$, $R^{2-2}$, $R^{2-3}$ and $R^{2-4}$ are independently F, Cl, Br or $C_1$-$C_3$ alkyl; and the $L^2$ is linked to

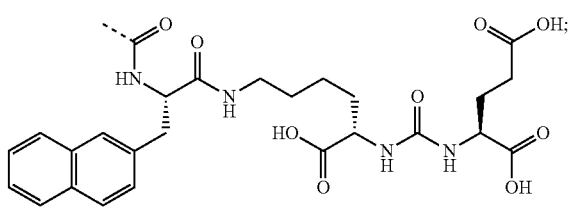

$L^3$ is —N($R^{3-1}$)— or —N($R^{3-2}$)-$L^{3-1}$-; and the $L^3$ is linked to R through a N atom;

$R^{3-1}$ and $R^{3-2}$ are independently H or $C_1$-$C_3$ alkyl;

$L^{3-1}$ is $C_1$-$C_3$ alkylene;

$L^4$ is a 3-6 membered monocyclic carbocyclic ring, a 5-12 membered bridged carbocyclic ring, a 5-12 membered carbon heterocyclic ring, a 6-14 membered aromatic ring, a 5-12 membered heteroaromatic ring, a 5-12 membered carbon heterocyclic ring substituted by $R^{4-1}$, a 6-14 membered aromatic ring substituted by $R^{4-2}$, a 5-12 membered heteroaromatic ring substituted by $R^{4-3}$ or a 5-12 membered bridged carbocyclic ring substituted by $R^{4-4}$; in the carbon heterocyclic ring, the number of heteroatoms is 1, 2 or 3, and the heteroatoms are selected from one or more of N, O and S; in the heteroaromatic ring, the number of heteroatoms is 1, 2 or 3, and the heteroatoms are selected from one or more of N, O and S; $R^{4-1}$, $R^{4-2}$, $R^{4-3}$ and $R^{4-4}$ are independently F, Cl, Br or $C_1$-$C_3$ alkyl; when $L^4$ is a 3-6 membered monocyclic carbocyclic ring, $L^3$ is —N($R^{3-1}$)—;

$L^5$ is a bond, a 5-12 membered carbocyclic ring, a 5-12 membered carbon heterocyclic ring, a 6-14 membered aromatic ring, a 5-12 membered heteroaromatic ring, a 5-12 membered carbocyclic ring substituted by $R^{5-1}$, a 5-12 membered carbon heterocyclic ring substituted by $R^{5-2}$, a 6-14 membered aromatic ring substituted by $R^{5-3}$ or a 5-12 membered heteroaromatic ring substituted by $R^{5-4}$; in the carbon heterocyclic ring, the number of heteroatoms is 1, 2 or 3, and the heteroatoms are selected from one or more of N, O and S; in the heteroaromatic ring, the number of heteroatoms is 1, 2 or 3, and the heteroatoms are selected from one or more of N, O and S; $R^{5-1}$, $R^{5-2}$, $R^{5-3}$ and $R^{5-4}$ are independently F, Cl, Br or $C_1$-$C_3$ alkyl; and the $L^5$ is linked to

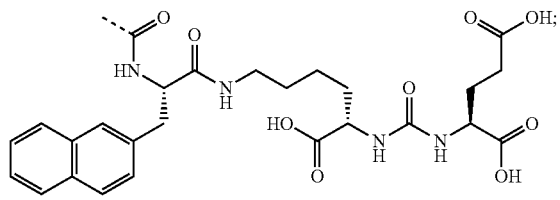

R is a group containing a radioactive metal ion or a group capable of optical imaging.

In a certain embodiment, in the peptide-urea derivative of formula I, a pharmaceutically acceptable salt thereof, a solvate thereof or a solvate of a pharmaceutically acceptable salt thereof, the definitions of certain groups are described as follows, and the definitions of remaining groups are described as in any of other embodiments (hereinafter referred to as "in a certain embodiment"):

$L^1$ is a bicyclic ring, wherein the ring directly linked to R is not aromatic.

In a certain embodiment, $L^1$ is a fused ring, wherein the ring directly attached to R is not aromatic.

In a certain embodiment, $L^1$ is a monocyclic ring.

In a certain embodiment, in $L^1$, the 5-12 membered carbon heterocyclic ring is a 6-11 membered carbon heterocyclic ring.

In a certain embodiment, in $L^1$, the 5-12 membered carbon heterocyclic ring is a 3-6 membered carbon monoheterocyclic ring.

In a certain embodiment, in $L^1$, in the 5-12 membered carbon heterocyclic ring, the number of heteroatoms is 1 or 2.

In a certain embodiment, in $L^1$, in the 5-12 membered carbon heterocyclic ring, the heteroatom is N.

In a certain embodiment, in L¹, the 5-12 membered carbon heterocyclic ring is a bicyclic ring.

In a certain embodiment, in L¹, the 5-12 membered carbon heterocyclic ring is a bicyclic ring, and the bicyclic ring is a bridged ring or a spiro ring.

In a certain embodiment, in L¹, the 5-12 membered heteroaromatic ring is a 9-10 membered heteroaromatic ring.

In a certain embodiment, in L¹, the 5-12 membered heteroaromatic ring is a bicyclic ring.

In a certain embodiment, in L¹, in the 5-12 membered heteroaromatic ring, the number of heteroatoms is 1 or 2.

In a certain embodiment, L¹ is

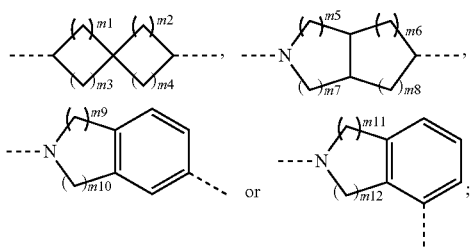

wherein m1, m2, m3, m4, m5, m6, m7, m8, m9, m10, m11 and m12 are independently 0, 1, 2, 3 or 4, m1+m3=1, 2, 3 or 4, m2+m4=1, 2, 3 or 4, m5+m7=0, 1, 2 or 3, m6+m8=0, 1, 2 or 3, m9+m10=0, 1, 2 or 3, and m11+m12=0, 1 2 or 3.

In a certain embodiment, L¹ is

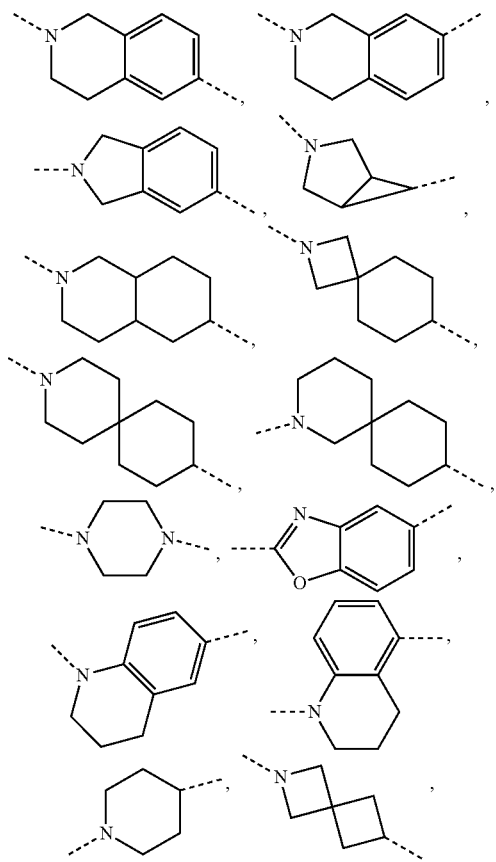

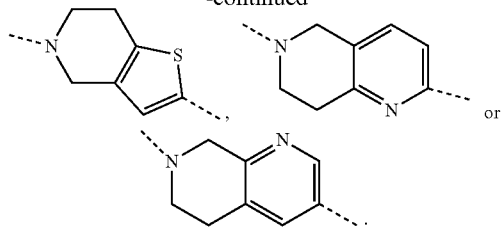

In a certain embodiment, L² is a bond

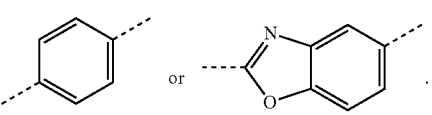

In a certain embodiment, in L², the 5-12 membered heteroaromatic ring is a 9-10 membered heteroaromatic ring.

In a certain embodiment, in L², the 5-12 membered heteroaromatic ring is a bicyclic ring.

In a certain embodiment, in L², the 5-12 membered heteroaromatic ring is a fused ring.

In a certain embodiment, in L², in the heteroaromatic ring, the number of heteroatoms is 2.

In a certain embodiment, in L², in the heteroaromatic ring, the heteroatoms is N and/or O.

In a certain embodiment, in L², the 6-14 membered aromatic ring is a benzene ring or a naphthalene ring.

In a certain embodiment, L³ is —NH— or —NH—CH₂—.

In a certain embodiment, the L⁴ is linked to L³ through a C atom.

In a certain embodiment, in L⁴, the 5-12 membered bridged carbocyclic ring is a 5-8 membered bridged carbocyclic ring.

In a certain embodiment, in L⁴, the 6-14 membered aromatic ring is a 9-10 membered aromatic ring.

In a certain embodiment, in L⁴, the 6-14 membered aromatic ring is a bicyclic ring.

In a certain embodiment, in L⁴, the 6-14 membered aromatic ring is a fused ring.

In a certain embodiment, in L⁴, the 5-12 membered heteroaromatic ring is a 5-10 membered heteroaromatic ring.

In a certain embodiment, in L⁴, the 5-12 membered heteroaromatic ring is a monocyclic or bicyclic ring.

In a certain embodiment, L⁴ is

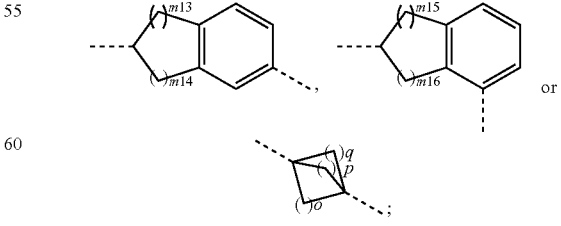

wherein m13, m14, m15 and m16 are independently 0, 1, 2 or 3, m13+m14=0, 1, 2 or 3, m15+m16=0, 1, 2 or 3; o, p and q are independently 1 or 2.

In a certain embodiment, $L^4$ is
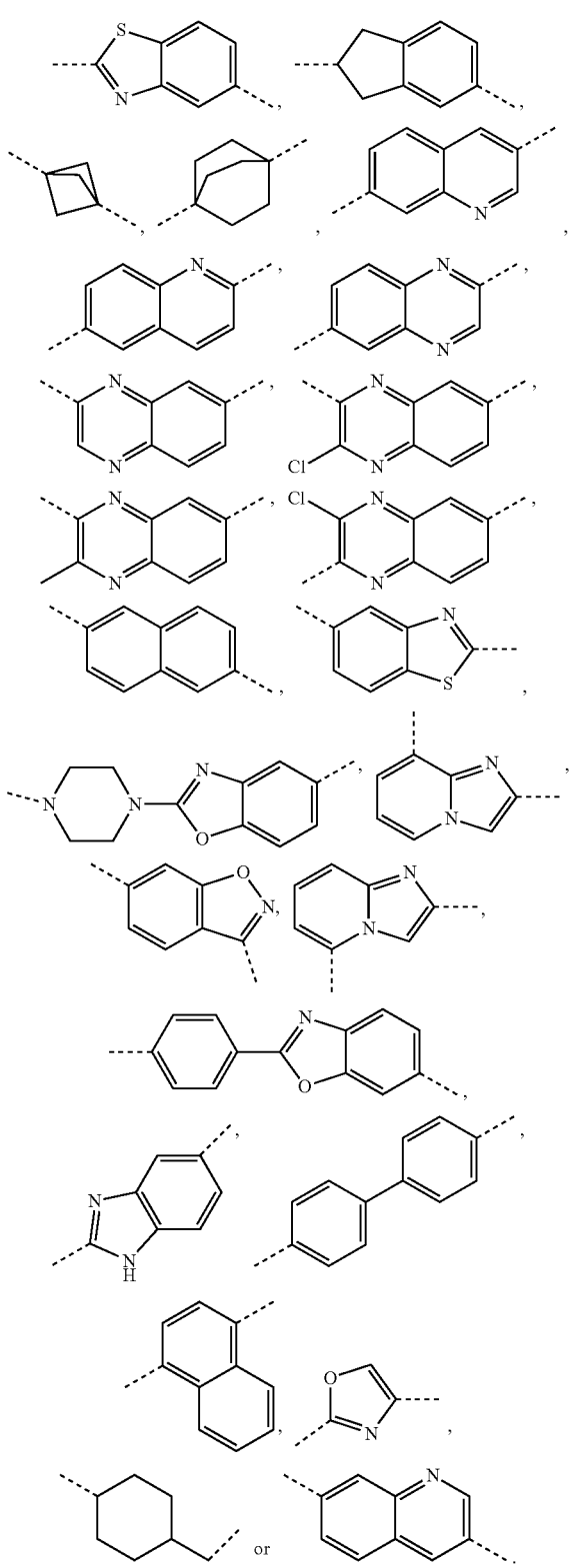
In a certain embodiment, in $L^5$, the 6-14 membered aromatic ring is a benzene ring or a naphthalene ring.
In a certain embodiment, $L^5$ is a bond or a benzene ring.
In a certain embodiment, L is
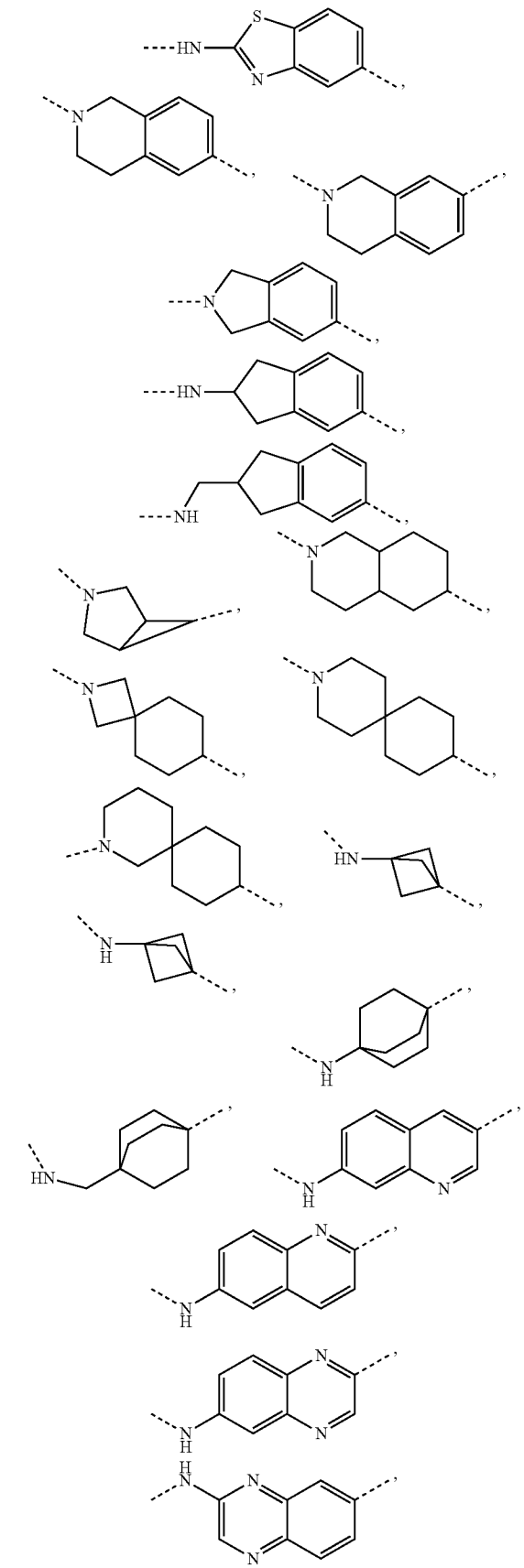

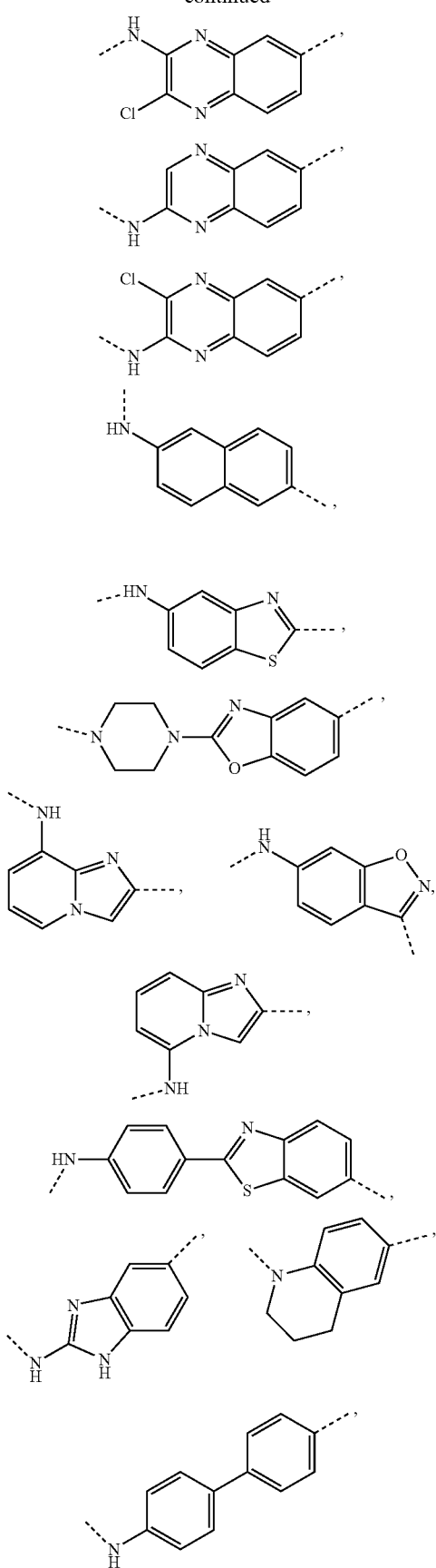

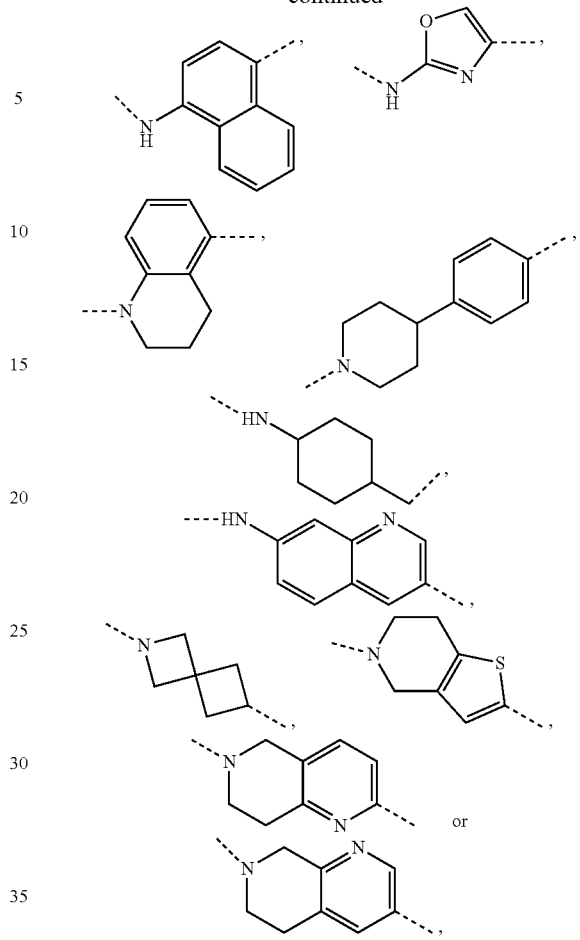

wherein the N atom is linked to R.

In a certain embodiment, the $C_1$-$C_3$ alkyl is methyl, ethyl, n-propyl or isopropyl.

In a certain embodiment, the $C_1$-$C_3$ alkylene is methylene, ethylene or propylene.

In a certain embodiment, the group containing a radioactive metal ion is composed of a radioactive metal ion and a group with the function of chelating a metal ion, and the radioactive metal ion is chelated with the group with the function of chelating a metal ion to form a chelate compound containing the radioactive metal ion.

In a certain embodiment, the group with the function of chelating a metal ion is

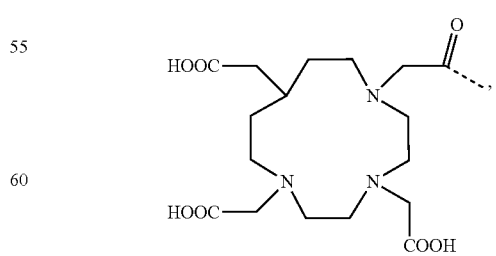

DOTA, NOTA, HBED-CC, NODAGA, NOTAGA, DOTAGA, TRAP, NOPO, PCTA, DFO, DTPA, CHX-DTPA, AAZTA or DEDPA.

-continued
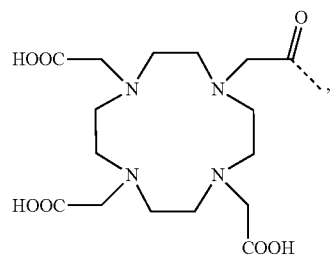
DOTA
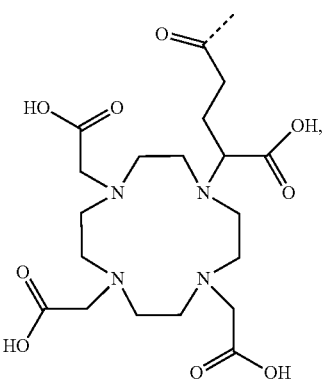
DOTAGA
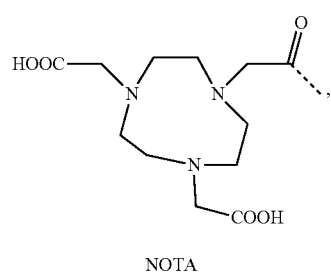
NOTA
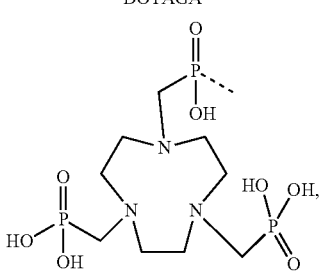
TRAP
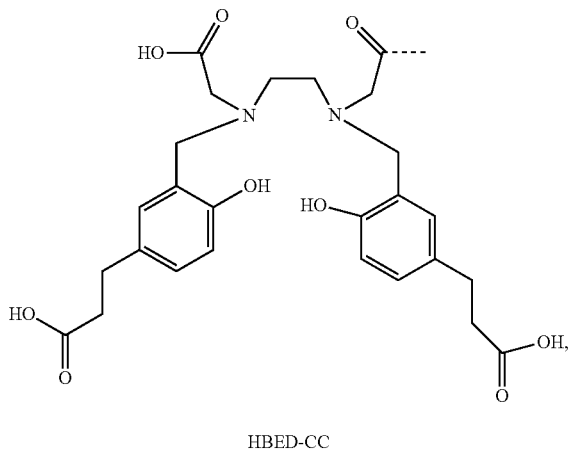
HBED-CC
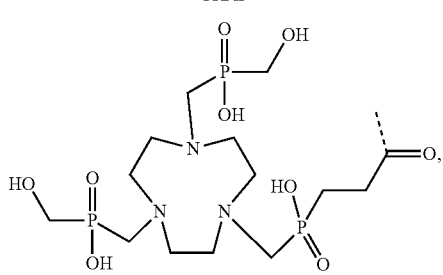
NOPO
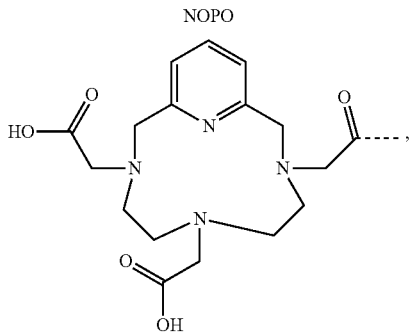
PCTA
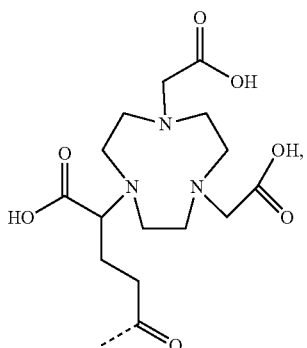
NODAGA
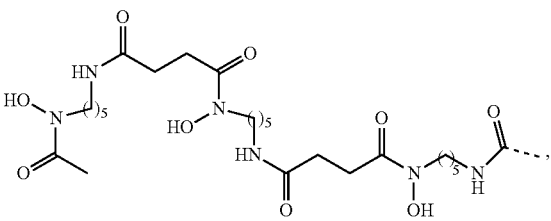
DFO -continued
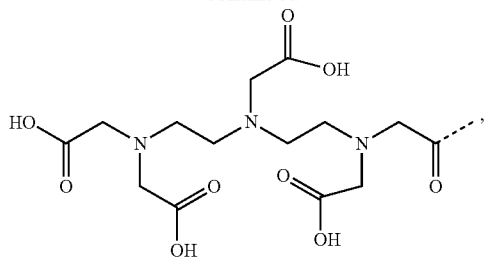
DTPA
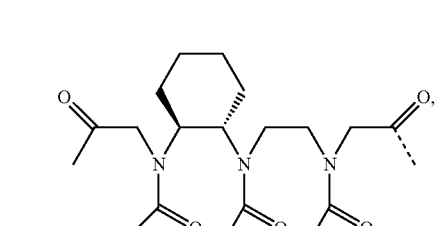
CHX-DTPA
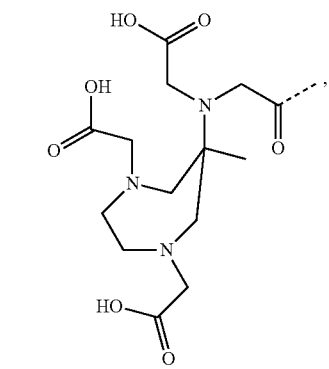
AAZTA
-continued
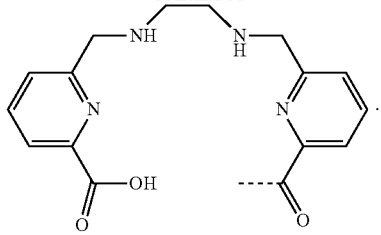
DEDPA
In a certain embodiment, the group with the function of chelating a metal ion is
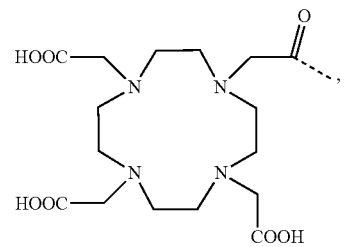
DOTA
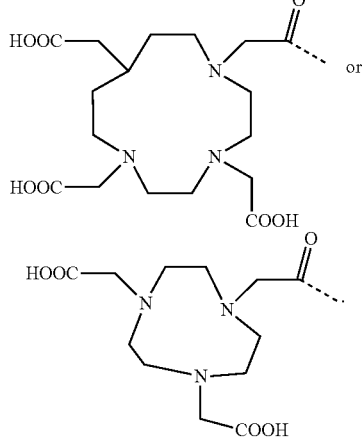
NOTA
In a certain embodiment, the peptide-urea derivative of formula I is the peptide-urea derivative of formula I-1,
I-1
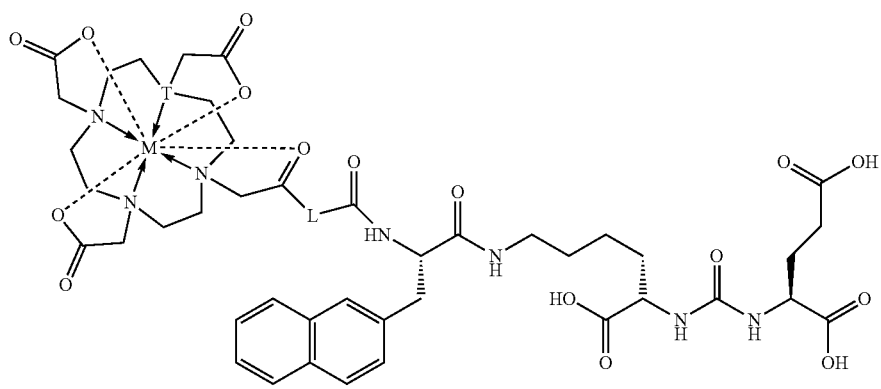
wherein T is N or CH, and M is the radioactive metal ion.

In a certain embodiment, when $L^4$ is a benzene ring, $L^3$ is —$N(R^{3-1})$— or $L^5$ is not a bond.

In a certain embodiment, the radioactive metal ion has one or more of the following effects:
(1) PET imaging;
(2) SPECT imaging;
(3) radiation treatment.

In a certain embodiment, the radioactive metal ion has one or more of the following effects:
(1) tracer;
(2) delivery;
(3) imaging;
(4) treatment.

In a certain solution, the radioactive metal ion is a radioactive metal ion releasing α, β or γ rays.

In a certain embodiment, the radioactive metal ion is $^{68}$Ga, $^{89}$Zr, $^{64}$Cu, $^{86}$Y, $^{99m}$Tc, $^{111}$In, $^{90}$Y, $^{67}$Ga, $^{177}$Lu, $^{211}$At, $^{153}$Sm, $^{186}$Re, $^{188}$Re, $^{67}$Cu, $^{212}$Pb, $^{225}$Ac, $^{223}$Ra, $^{213}$Bi, $^{212}$Bi or $^{212}$Pb.

In a certain embodiment, the radioactive metal ion is $^{68}$Ga$^{3+}$, $^{89}$Zr$^{4+}$, $^{64}$Cu$^{2+}$, $^{86}$Y$^{3+}$, $^{99m}$Tc$^{4+}$, $^{111}$In$^{3+}$, $^{90}$Y, $^{67}$Ga$^{3+}$, $^{177}$Lu$^{3+}$, $^{211}$At, $^{153}$Sm, $^{186}$Re, $^{188}$Re, $^{67}$Cu$^{2+}$, $^{212}$Pb$^{2+}$, $^{225}$Ac$^{3+}$, $^{223}$Ra, $^{213}$Bi$^{3+}$, $^{212}$Bi or $^{212}$Pb$^{2+}$.

In a certain solution, the radioactive metal ion is $^{68}$Ga or $^{177}$Lu.

In a certain solution, the radioactive metal ion is $^{68}$Ga$^{3+}$ or $^{177}$Lu$^{3+}$.

In a certain embodiment, the group capable of optical imaging is a fluorescent group, such as cy3, cy5 or cy7.

In a certain embodiment, L is -$L^1$-$L^2$- or -$L^3$-$L^4$-$L^5$-.
$L^1$ is a 5-12 membered carbon heterocyclic ring or a 5-12 membered heteroaromatic ring;
$L^2$ is a bond;
$L^3$ is —$N(R^{3-1})$— or —$N(R^{3-2})$-$L^{3-1}$-; and the $L^3$ is linked to R through a N atom;
$R^{3-1}$ and $R^{3-2}$ are independently H or $C_1$-$C_3$ alkyl;
$L^{3-1}$ is $C_1$-$C_3$ alkylene;
$L^4$ is a 5-12 membered bridged carbocyclic ring or a 5-12 membered heteroaromatic ring;
$L^5$ is a bond;
R is a group containing a radioactive metal ion.

In a certain embodiment, the peptide-urea derivative of formula I is a compound formed by chelating compound A and the radioactive metal ion (such as $^{68}$Ga$^{3+}$ or $^{177}$Lu$^{3+}$) wherein the structure of compound A is as shown in any of the following structures:

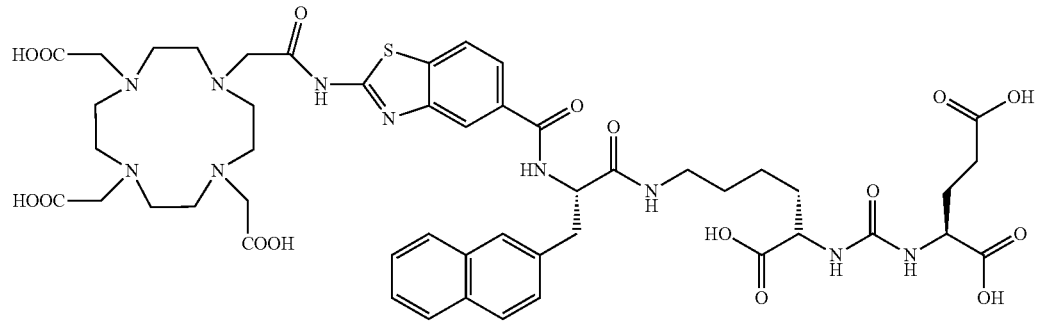

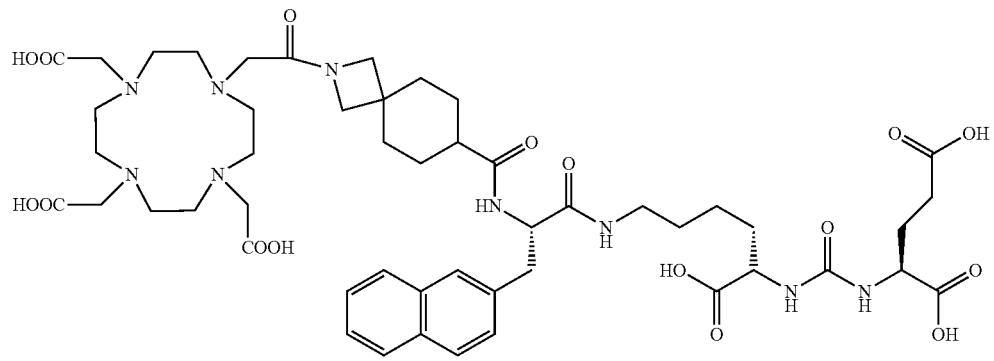

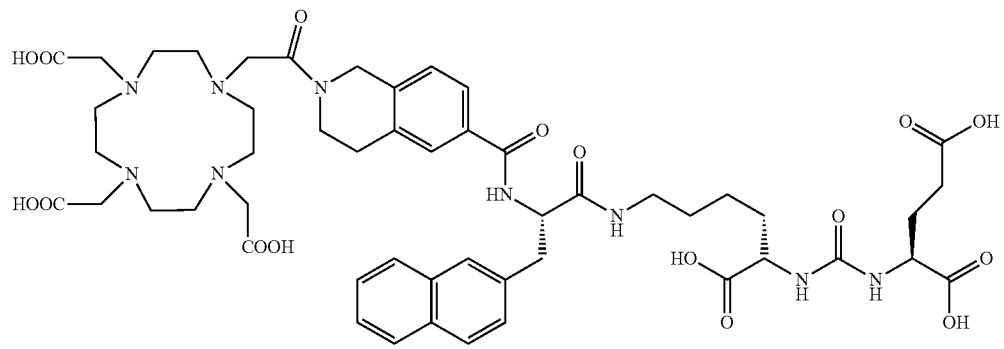

-continued
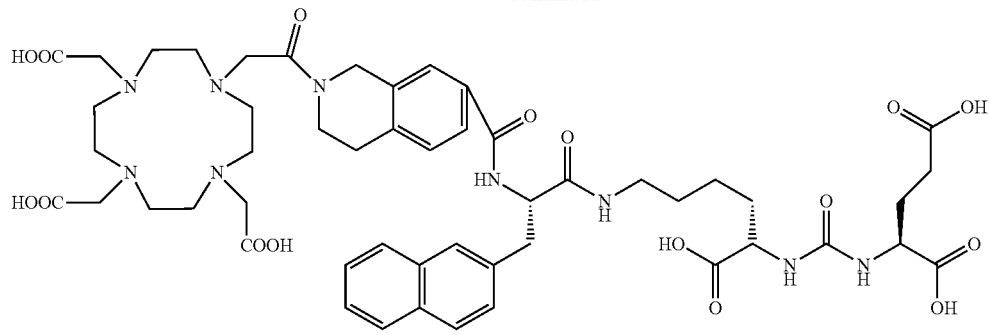
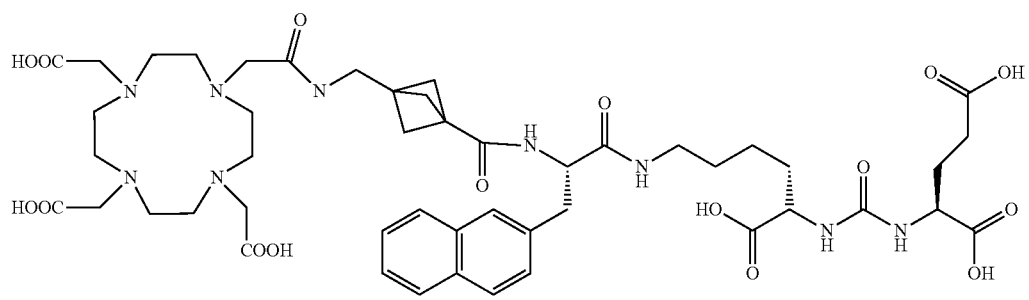
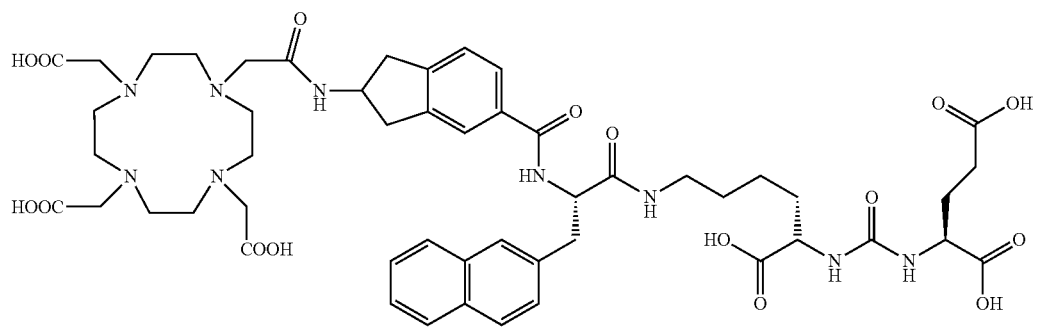
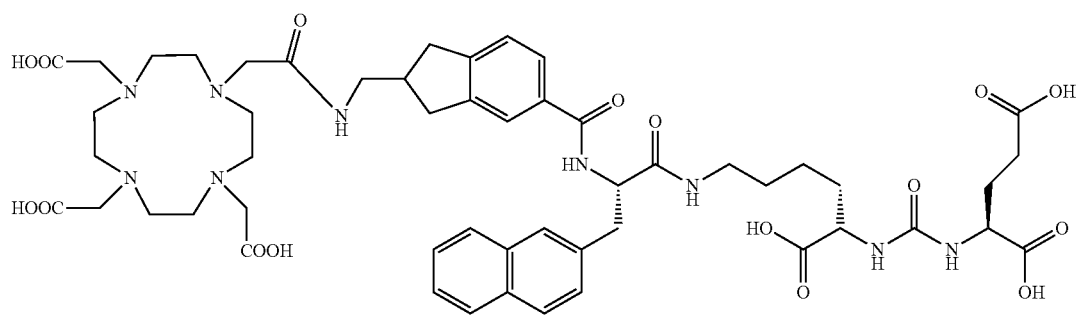
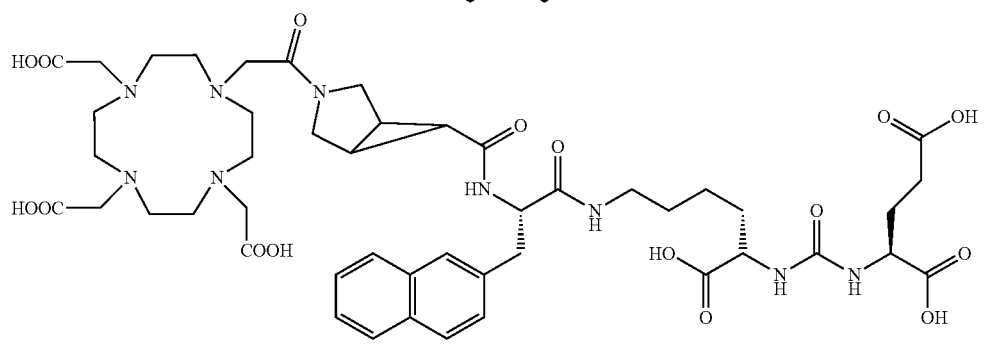

-continued
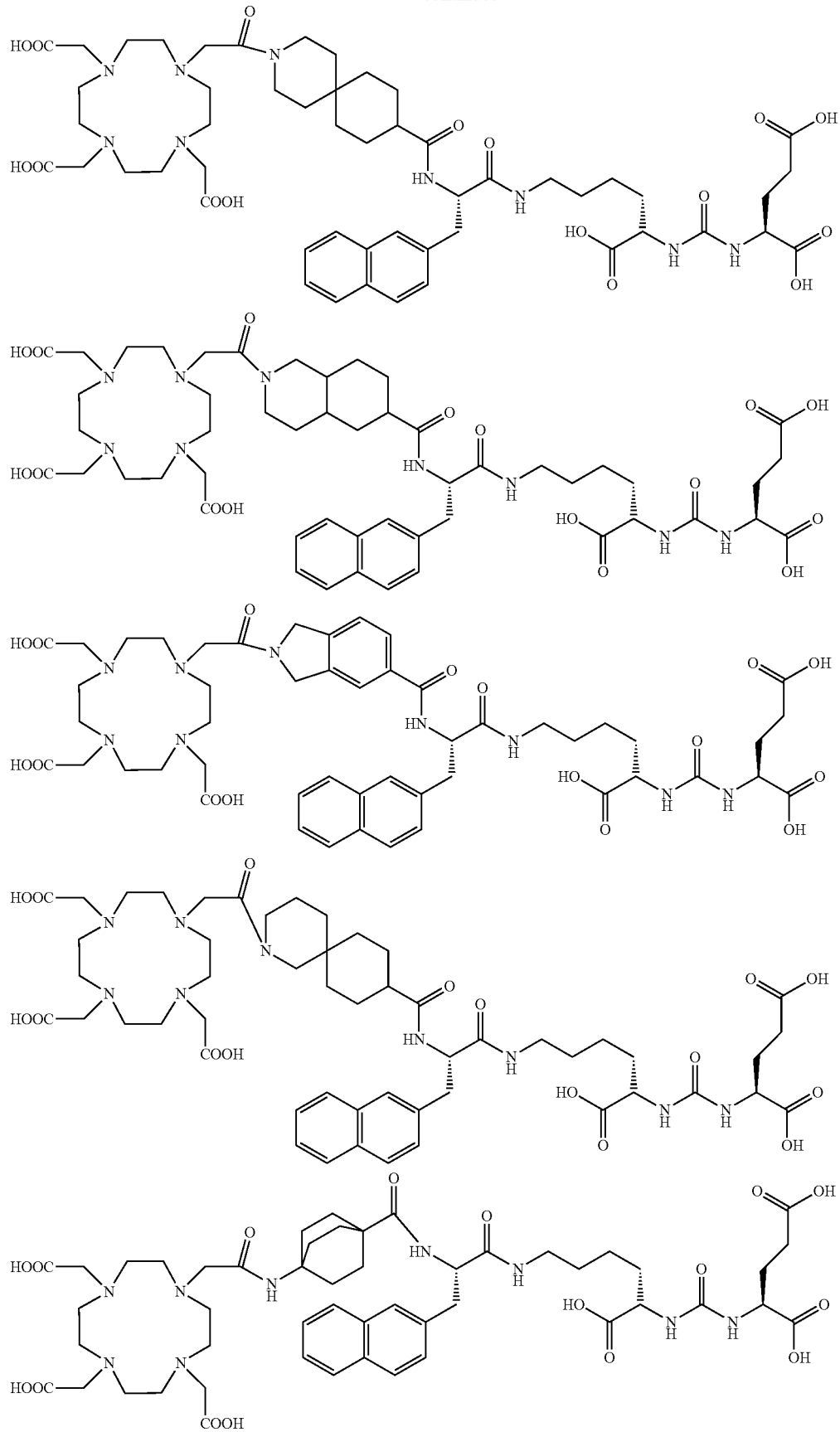

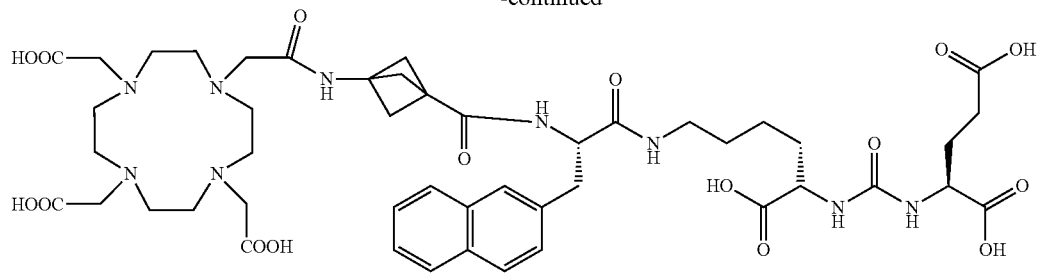
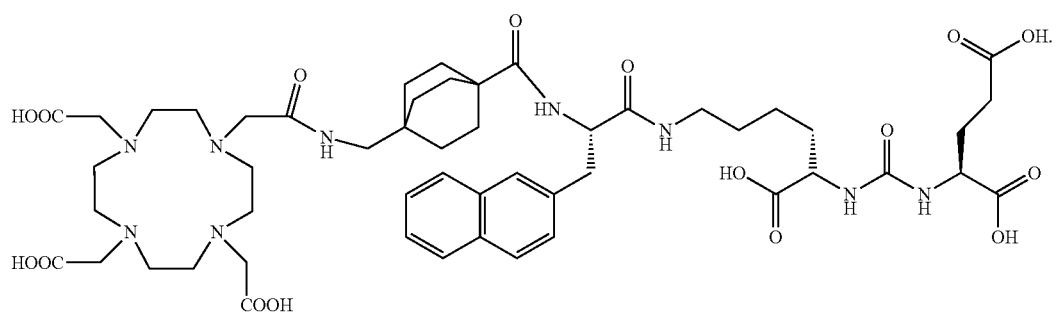
In a certain embodiment, the peptide-urea derivative of formula I is a compound formed by chelating compound A and $^{68}Ga^{3+}$, wherein the structure of compound A is as shown in any of the following structures:
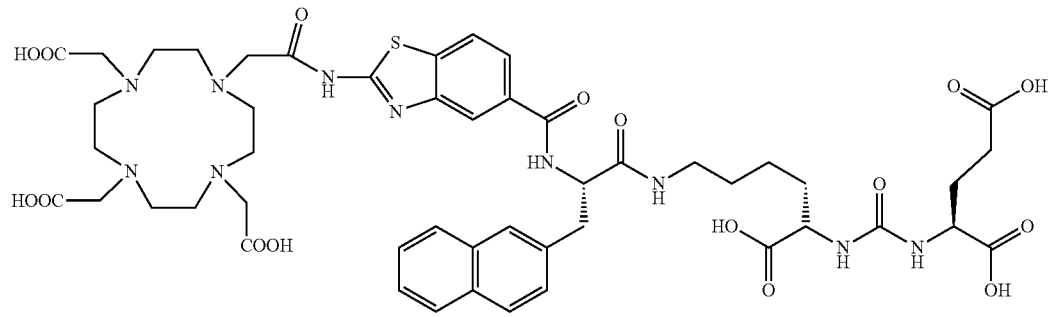
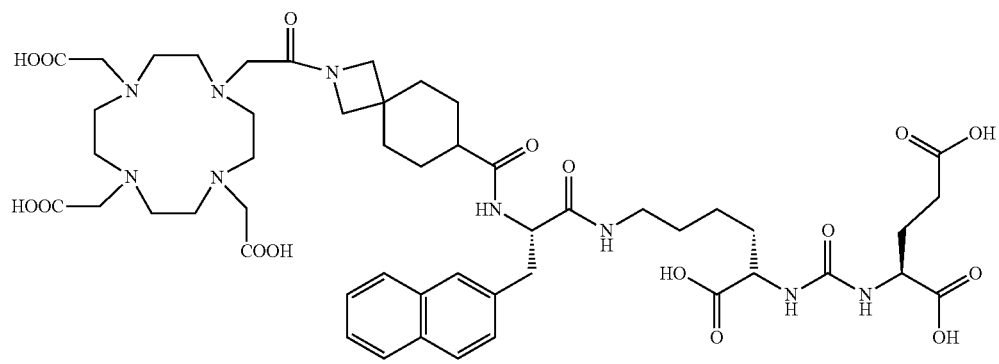

-continued
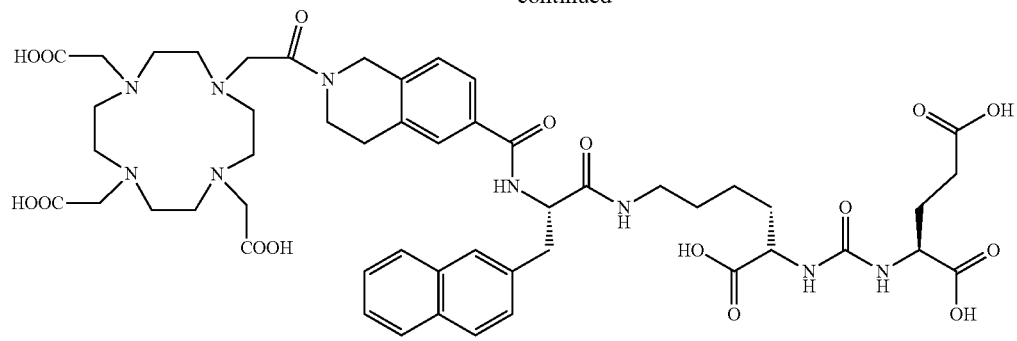
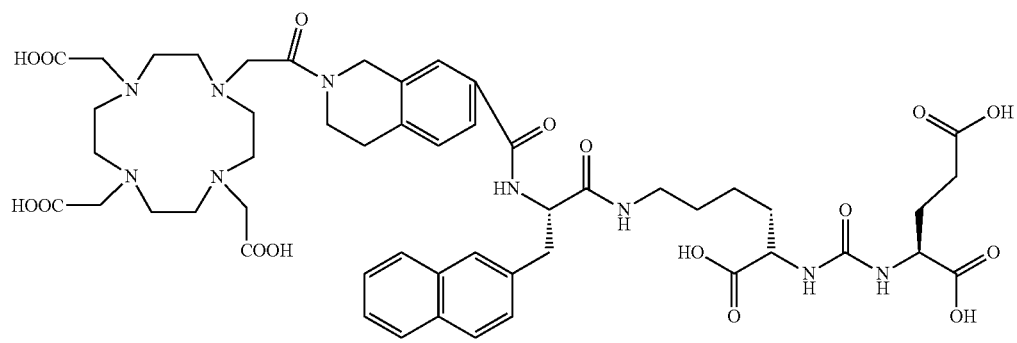
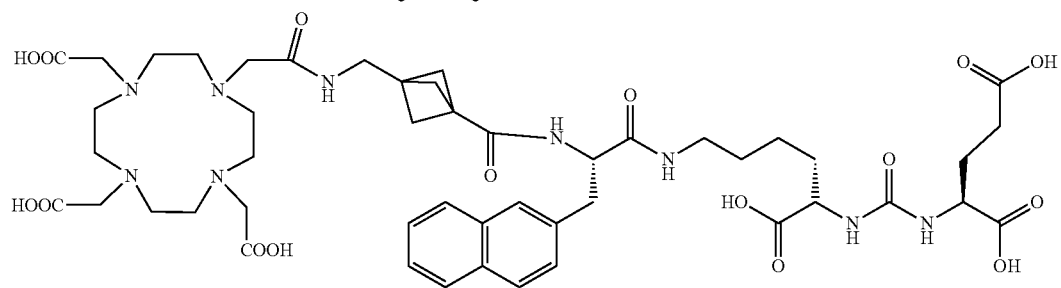
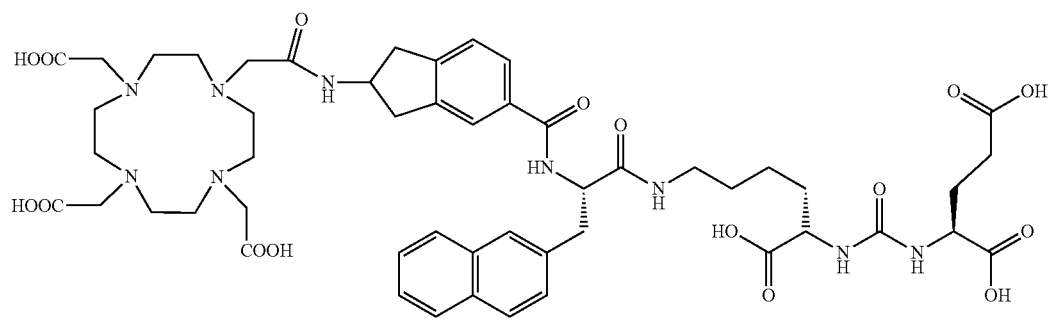
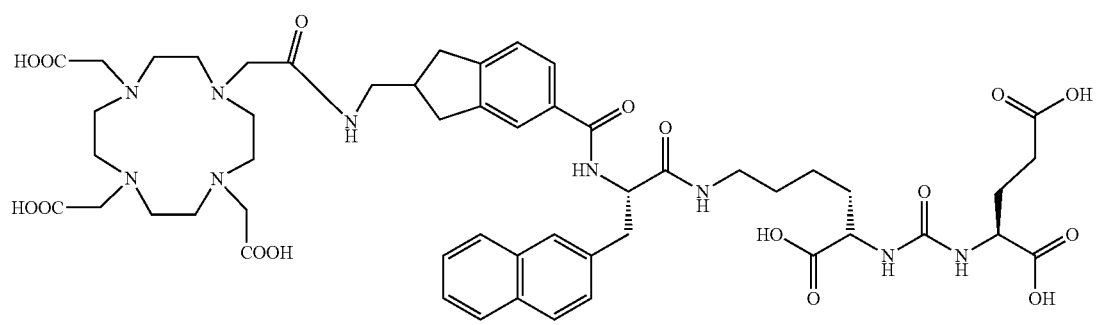

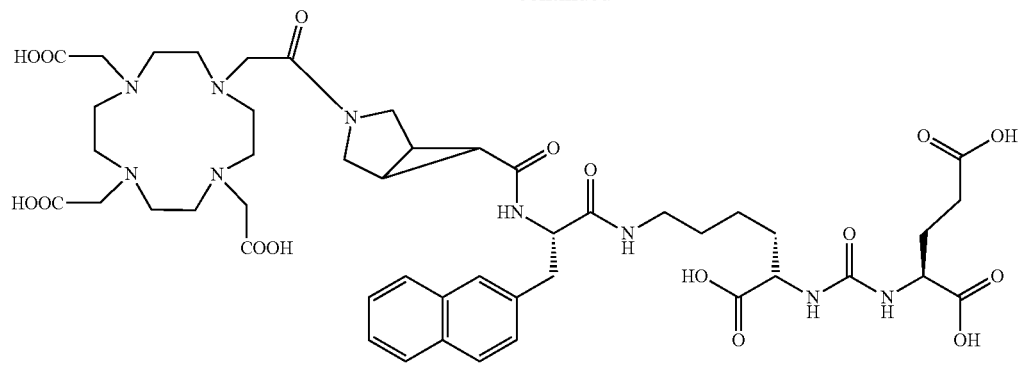
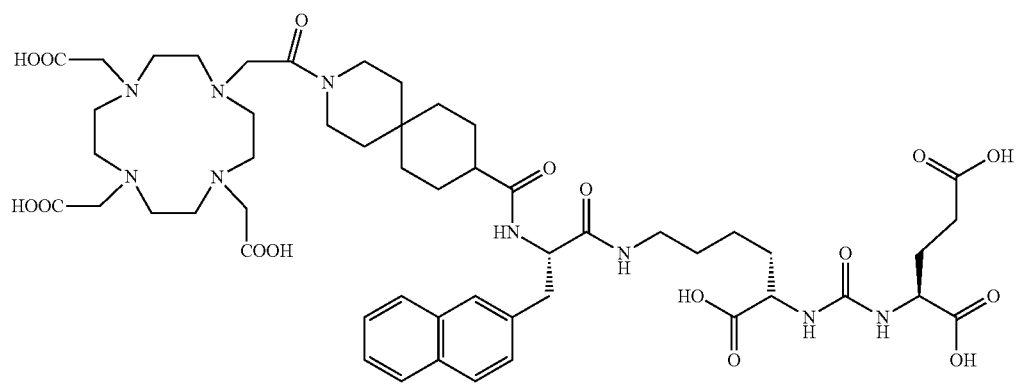
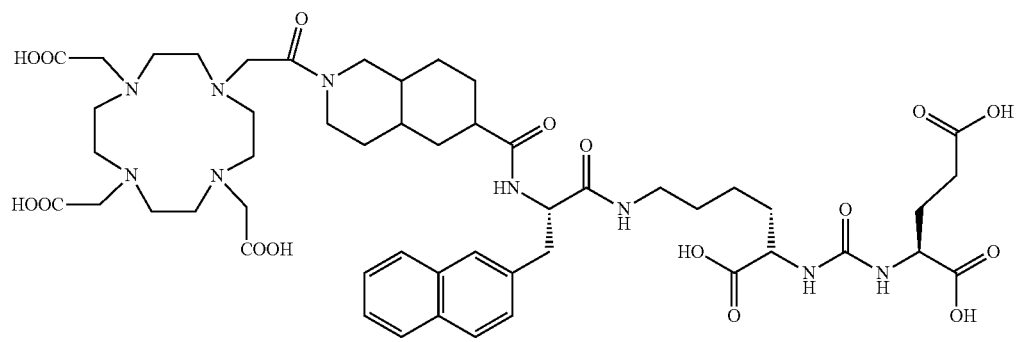
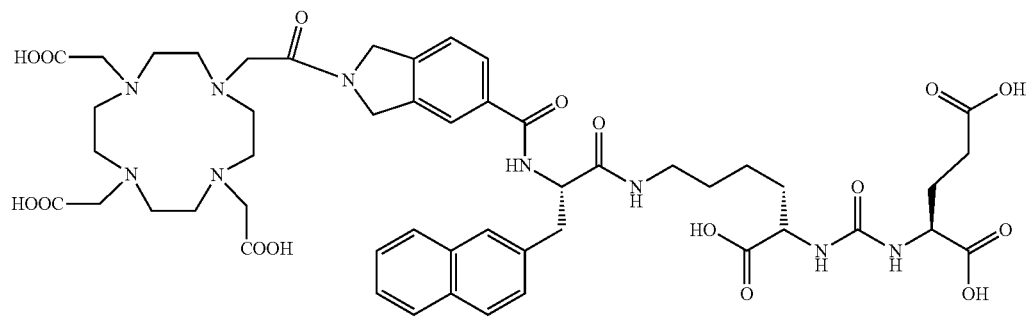

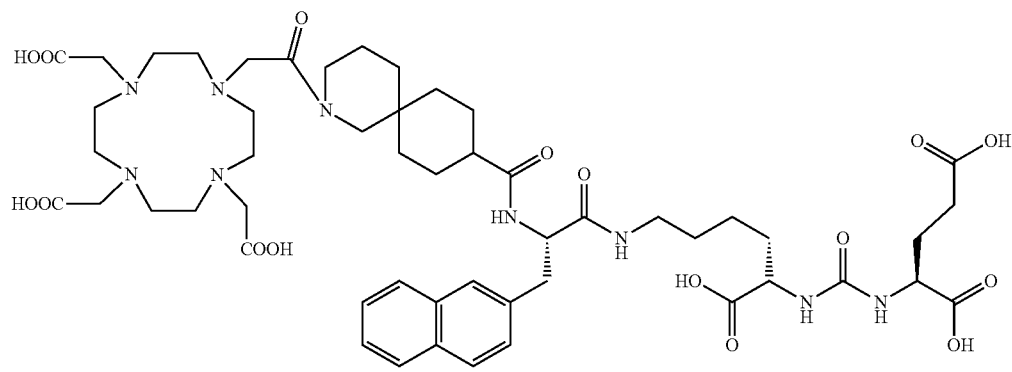
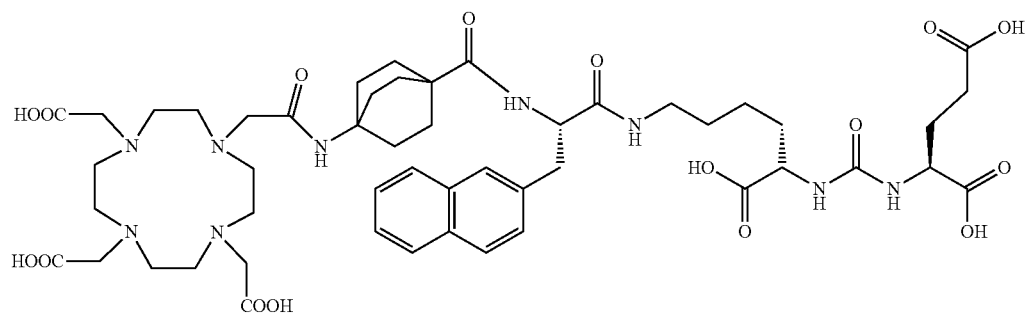
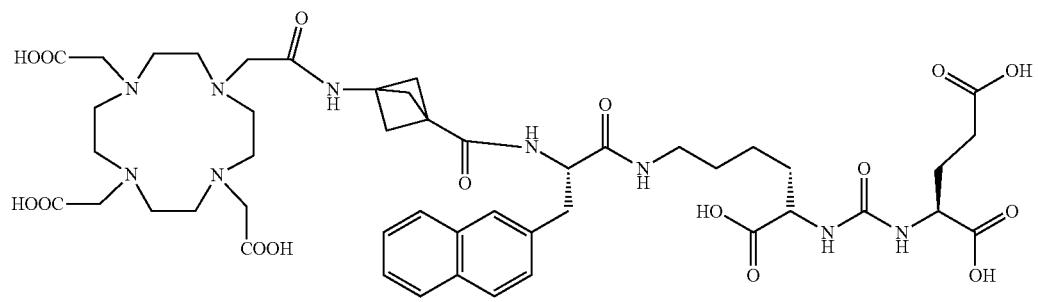
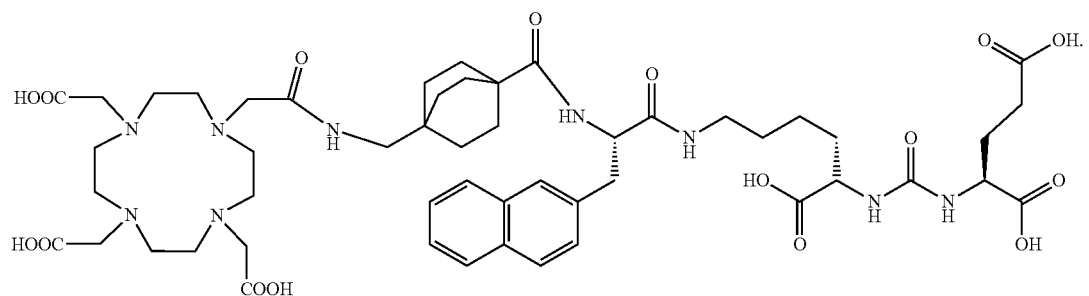

In a certain embodiment, the peptide-urea derivative of formula I is a compound formed by chelating compound A and $^{177}Lu^{3+}$, wherein the structure of compound A is as shown in any of the following structures:
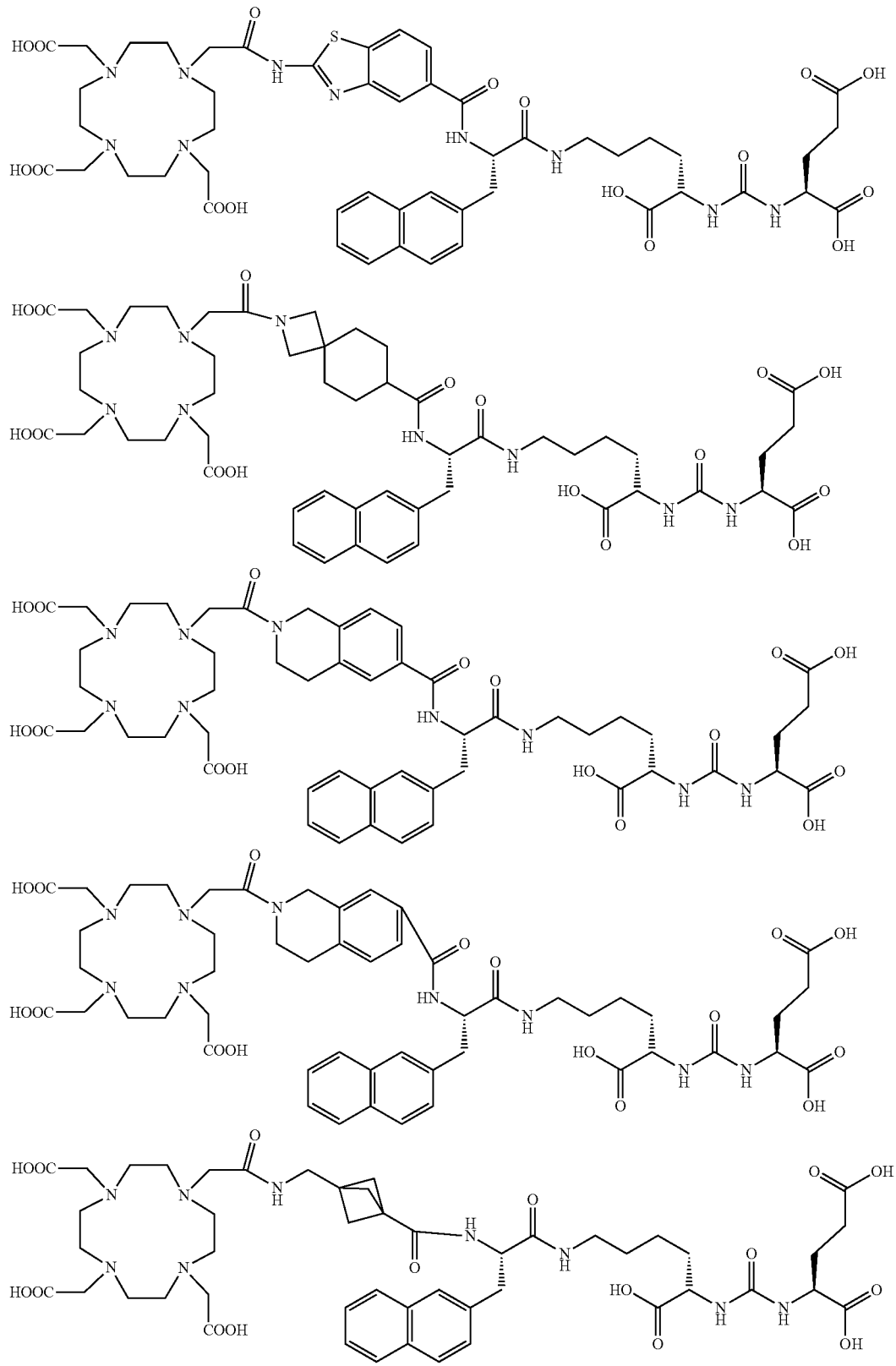

-continued
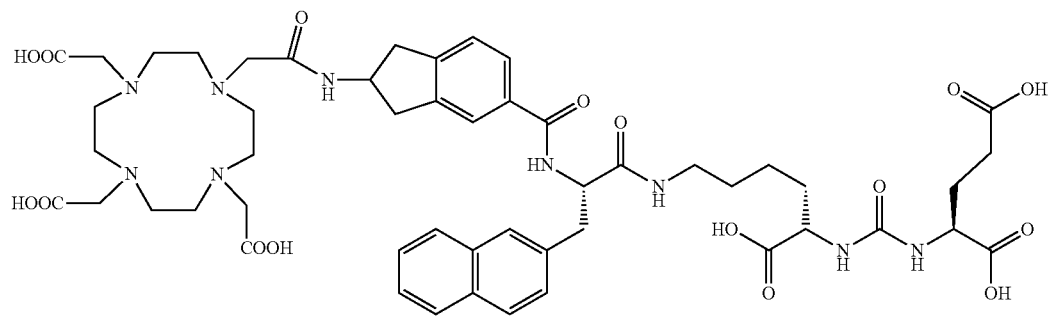
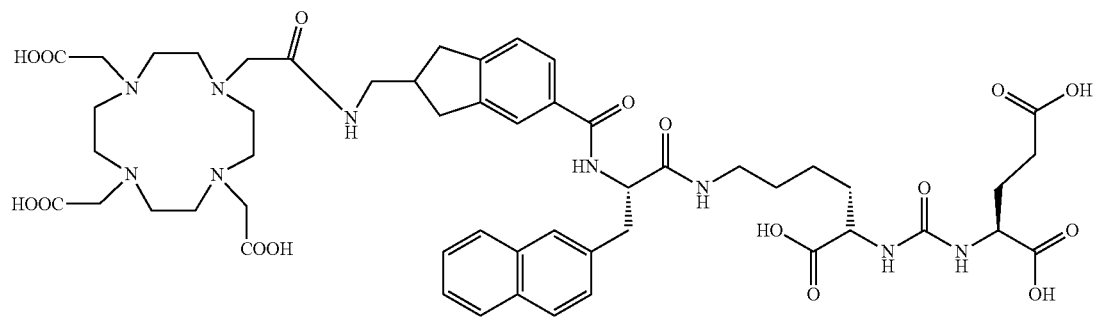
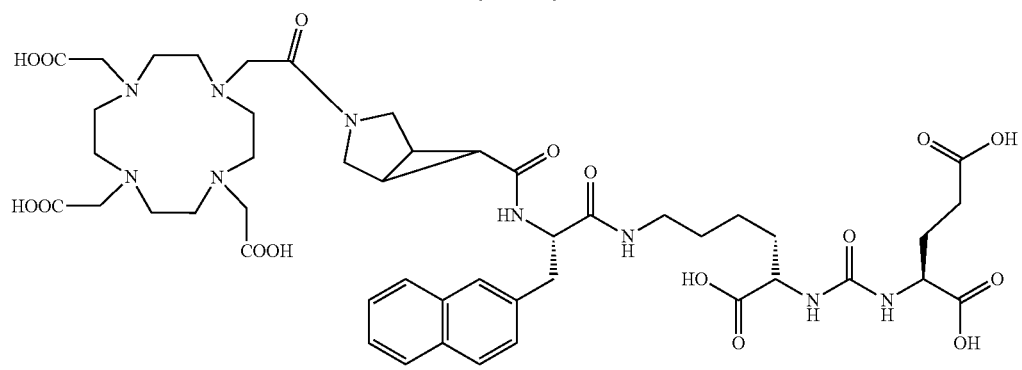
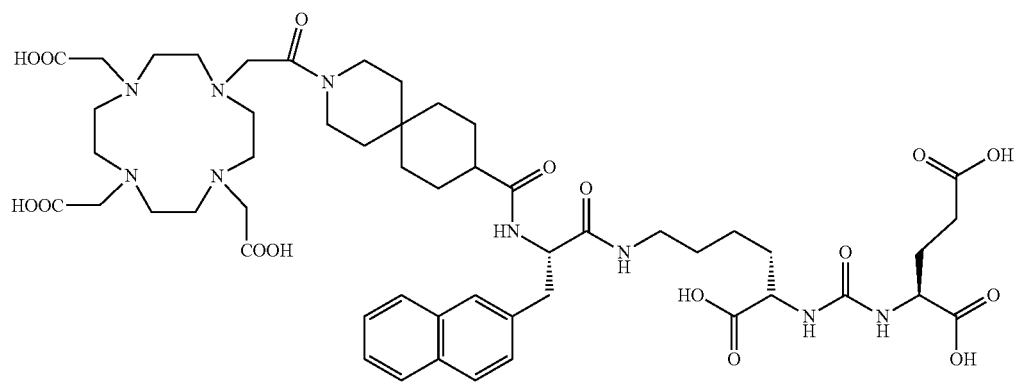
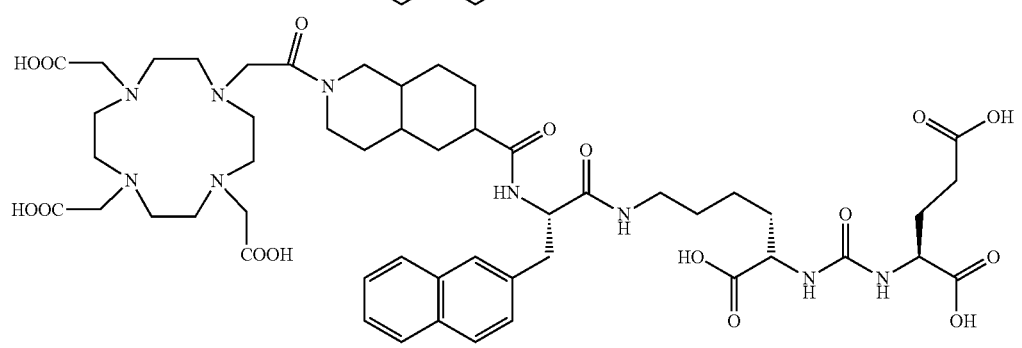

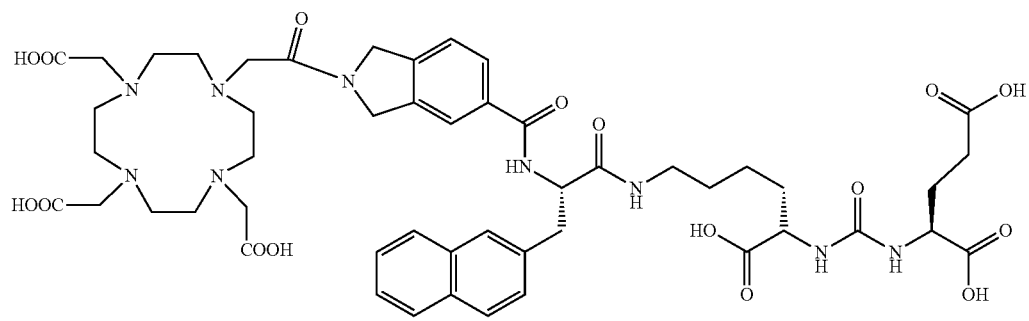
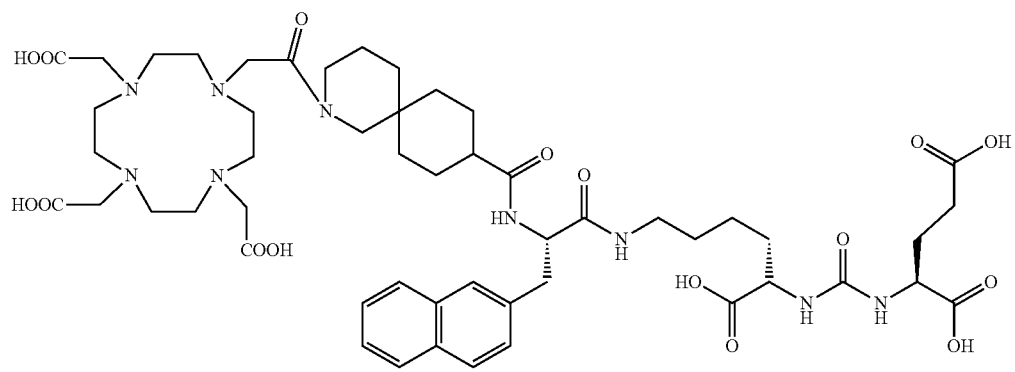
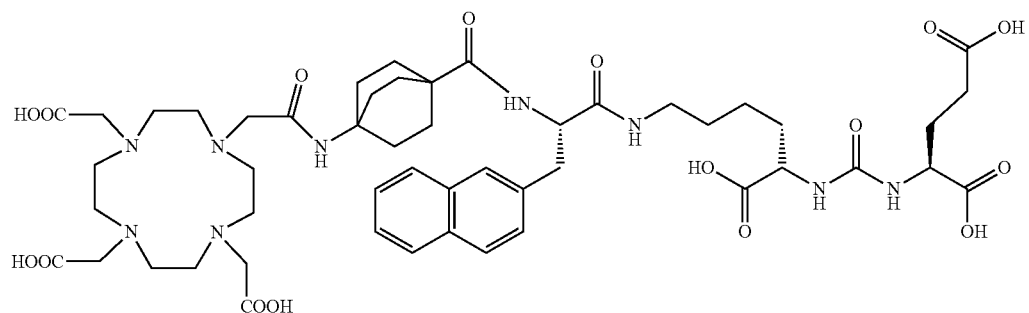
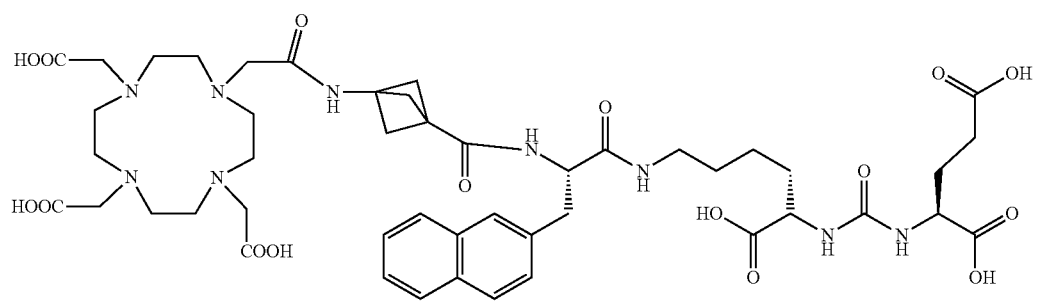
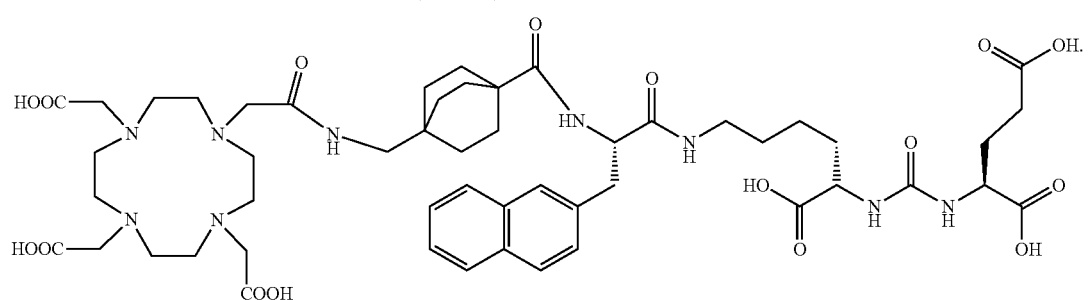

In a certain embodiment, the structure of the peptide-urea derivative of formula I is as follows:
177Lu-E1
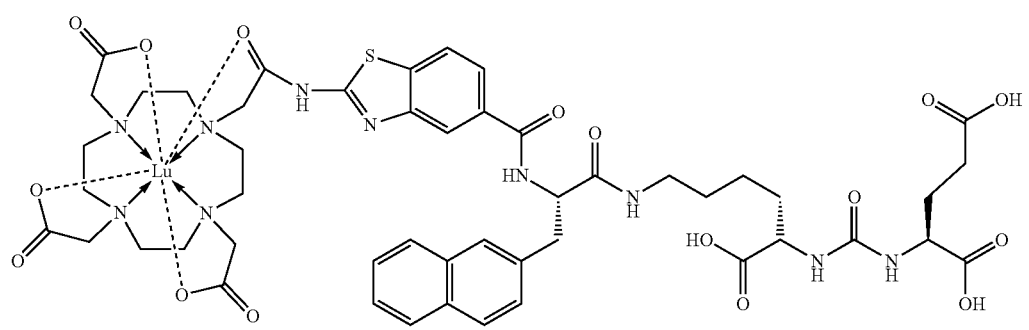
177Lu-E2
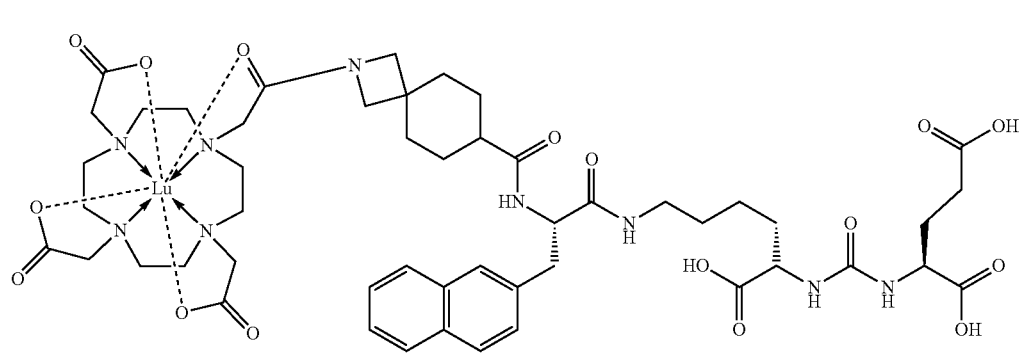
177Lu-E3
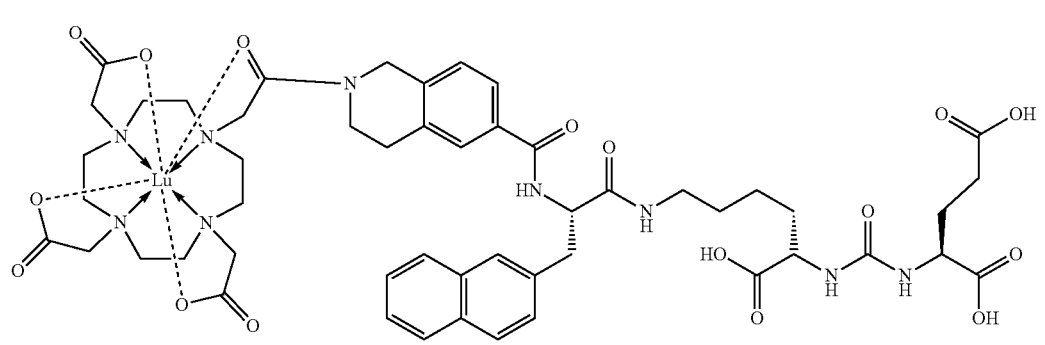
177Lu-E5
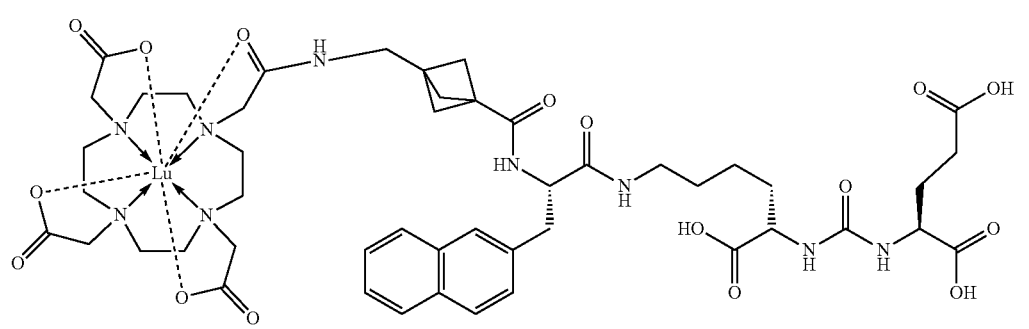

-continued

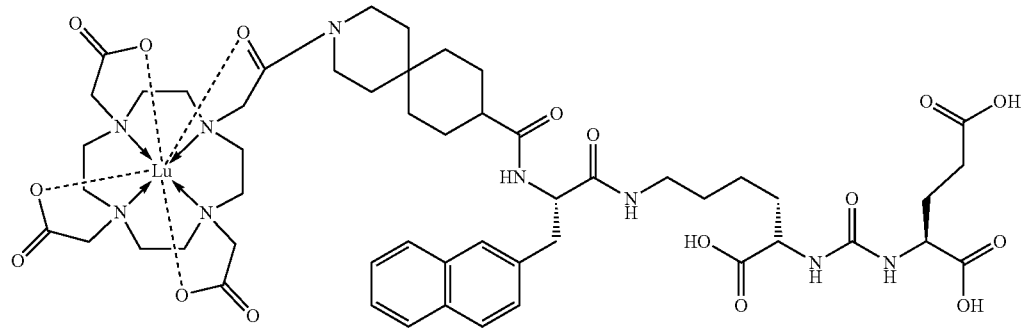

177Lu-E9

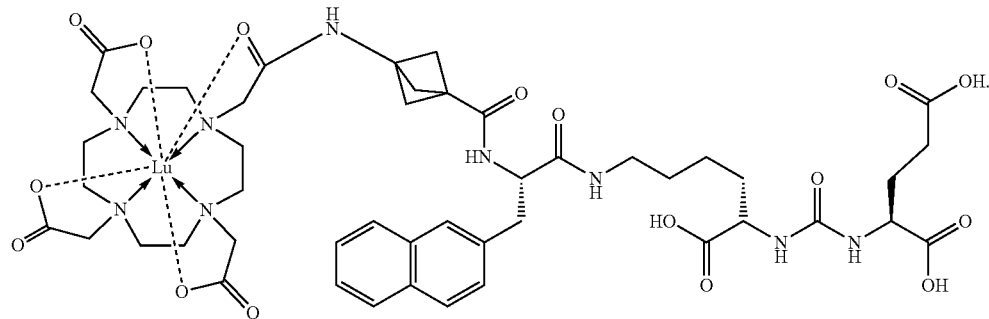

177Lu-E14

The present disclosure also provides a method for preparing the above-mentioned peptide-urea derivative of formula I, which includes the following steps: chelating a radioactive metal ion with the compound of formula II;

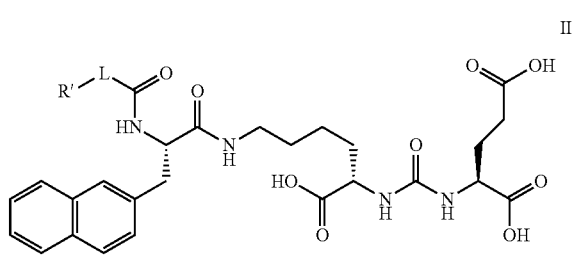

II wherein in the peptide-urea derivative of formula I, R is a group containing a radioactive metal ion; in the compound of formula II, R' is a group with the function of chelating a metal ion.

In a certain embodiment, the chelation conditions are conventional chelation conditions in the art.

The present disclosure also provides a compound of formula II, a compound of formula III or a compound of formula IV;

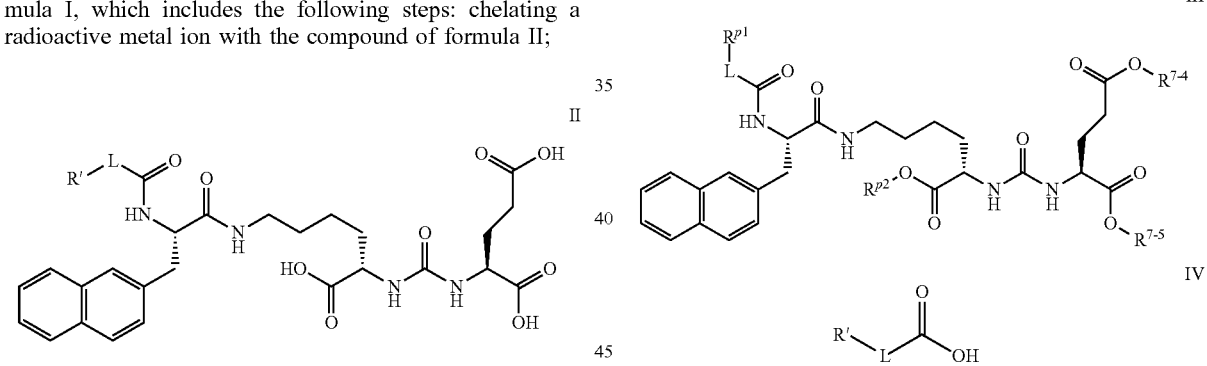

wherein R' is a group with the function of chelating a metal ion, the definition of L is as mentioned above; $R^{p1}$ is hydrogen or amino protecting group, $R^{p2}$ is hydrogen or resin, and $R^{7-4}$ and $R^{7-5}$ are independently hydrogen or $C_1$-$C_4$ alkyl.

In the compound of formula III, the amino protecting group is a conventional amino protecting group in the art, such as Fmoc.

In the compound of formula III, the resin is, but not limited to, Wang resin.

In the compound of formula III, $R^{7-4}$ is methyl, ethyl, n-propyl, isopropyl, n-butyl, sec-butyl, isobutyl or tert-butyl.

In the compound of formula III, $R^{7-5}$ is methyl, ethyl, n-propyl, isopropyl, n-butyl, sec-butyl, isobutyl or tert-butyl.

In the compound of formula IV, the definition of the group with the function of chelating a metal ion is as described above.

The compound of formula IV is
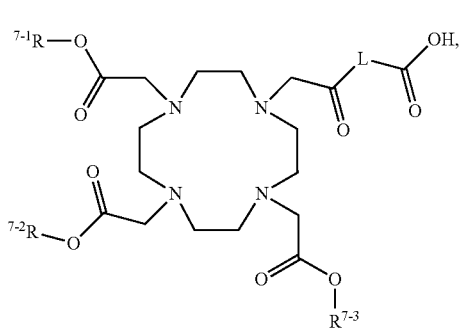
IV-1
and $R^{7-1}$, $R^{7-2}$ and $R^{7-3}$ are independently $C_1$-$C_4$ alkyl.
In the compound of formula IV, $R^{7-1}$, $R^{7-2}$ and $R^{7-3}$ are independently methyl, ethyl, n-propyl, isopropyl, n-butyl, sec-butyl, isobutyl or tert-butyl.
The compound of formula IV is
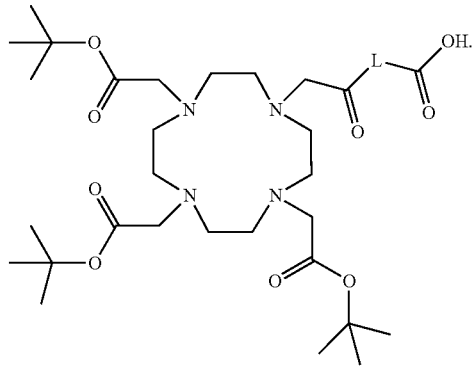
IV-2
The compound of formula IV is M2
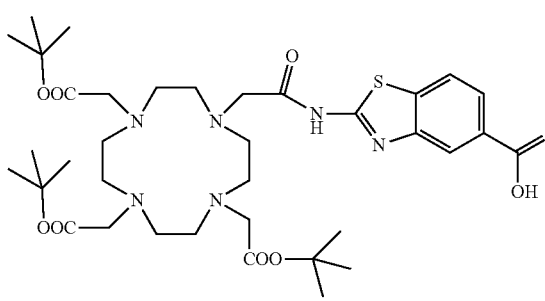
M2
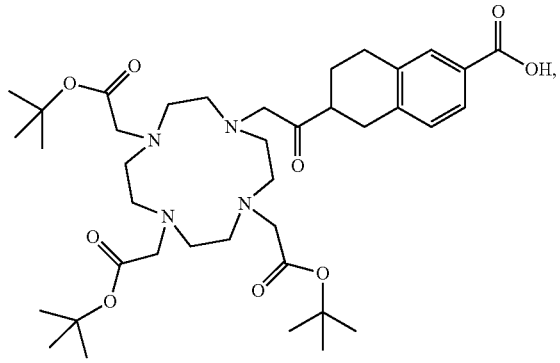
B3
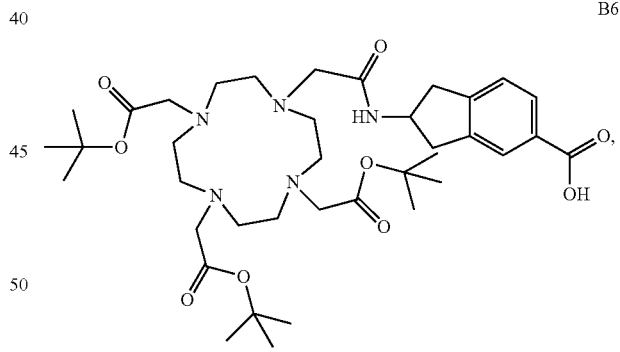
B4
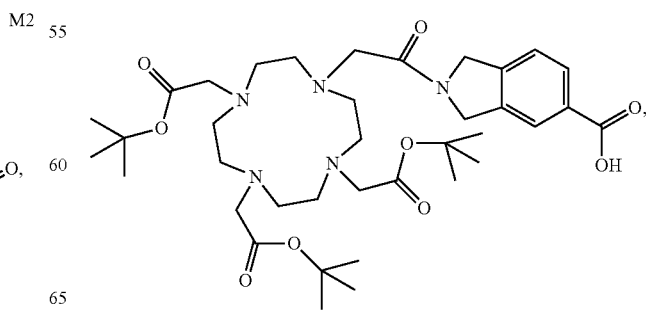
B6
B11

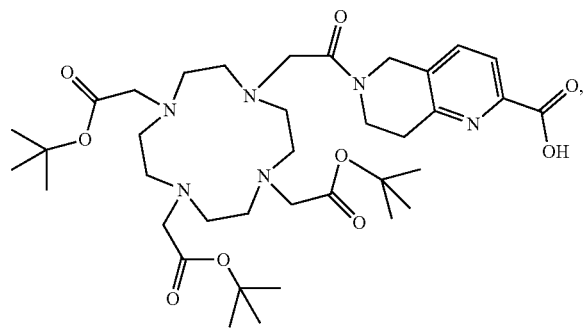
B17
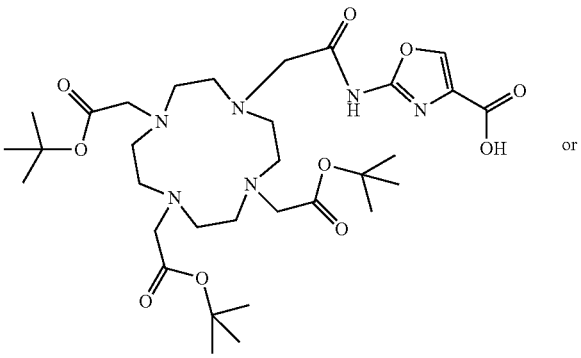
B23
or
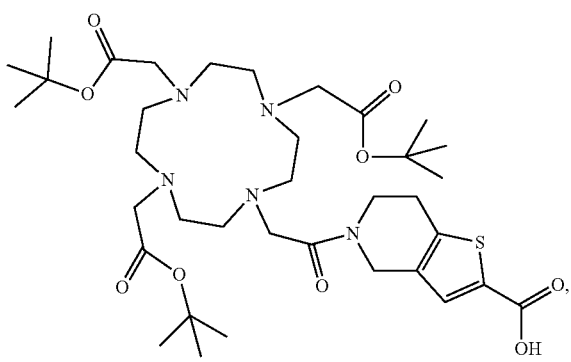
B18
B24
In the compound of formula II, the definition of the group with the function of chelating a metal ion is as described above.
In the compound of formula II, the group with the function of chelating a metal ion is not chelated with a metal ion.
The compound of formula II is a compound of formula II-1:
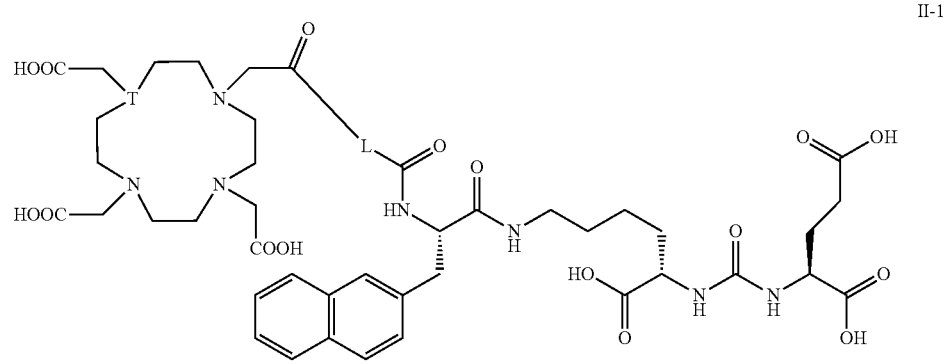
II-1
wherein T is N or CH.

The structure of the compound of formula II is as shown in any of the following:
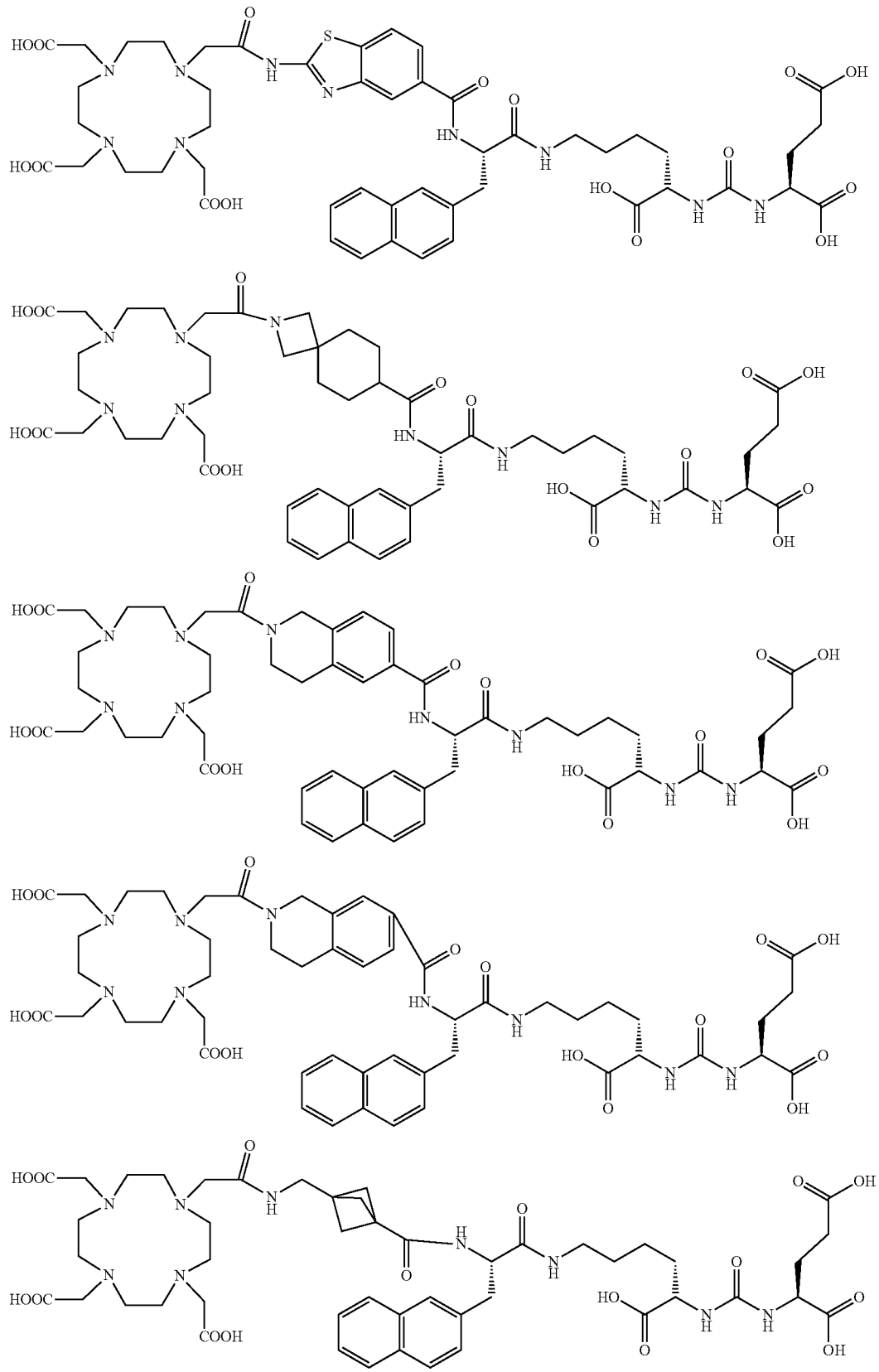

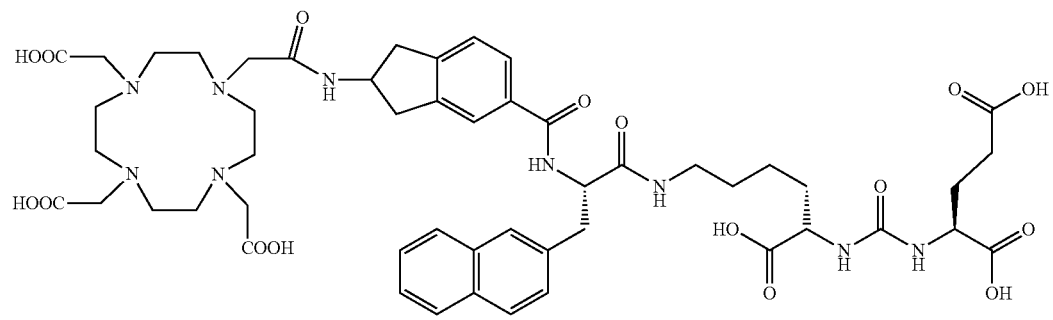
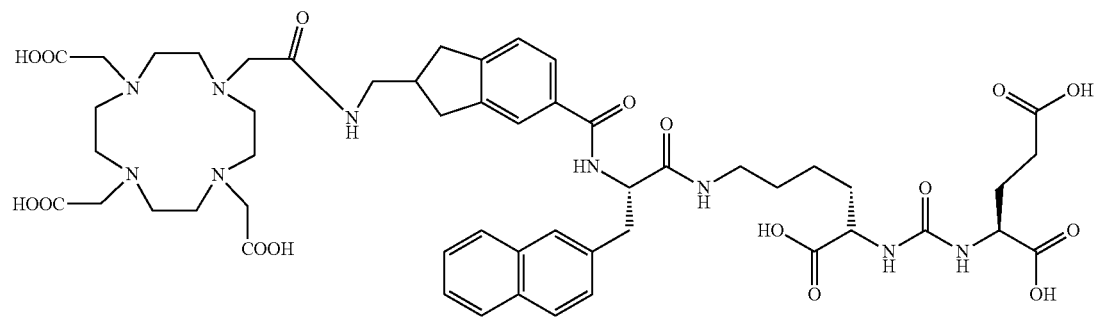
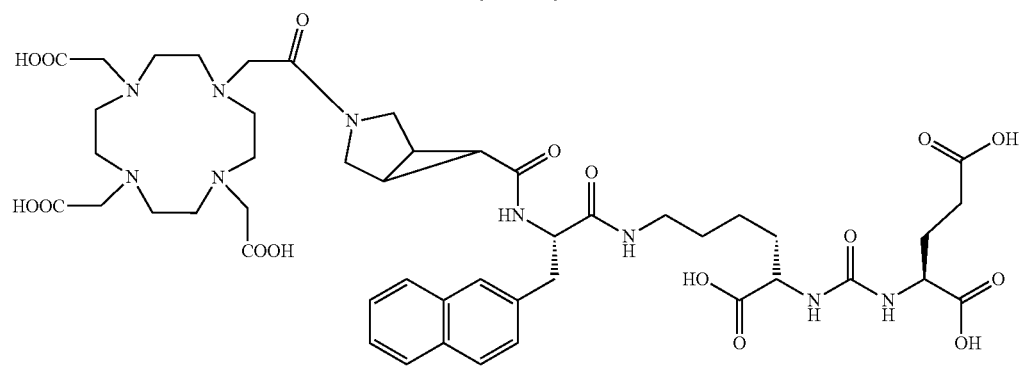
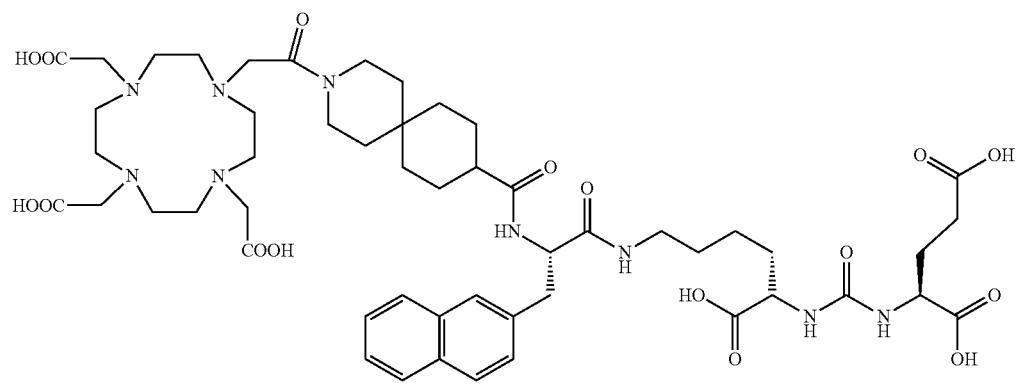
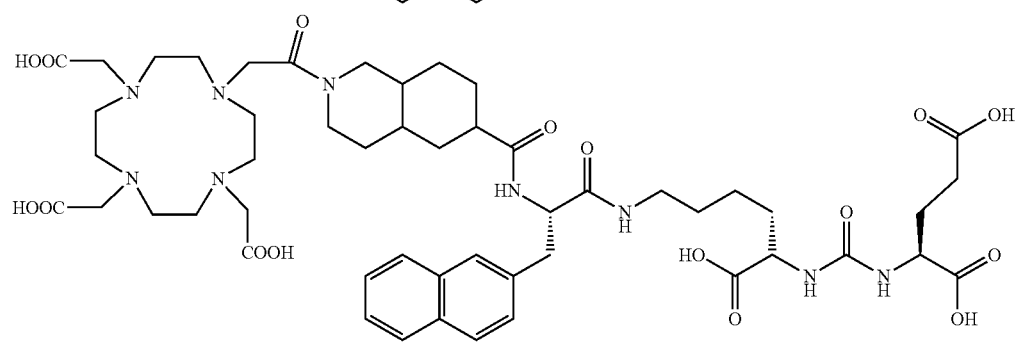

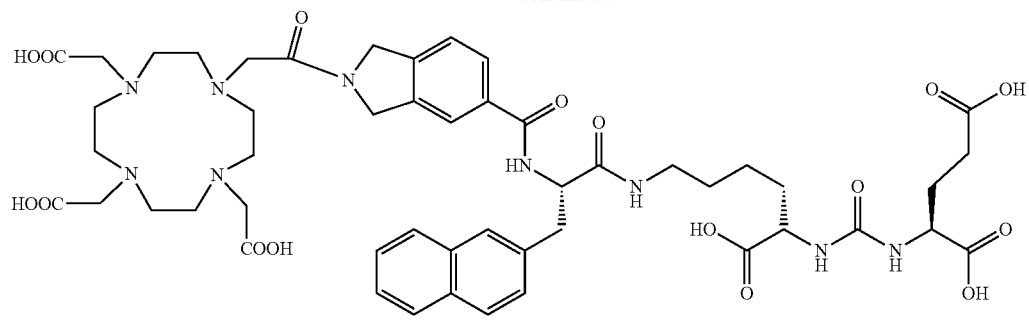
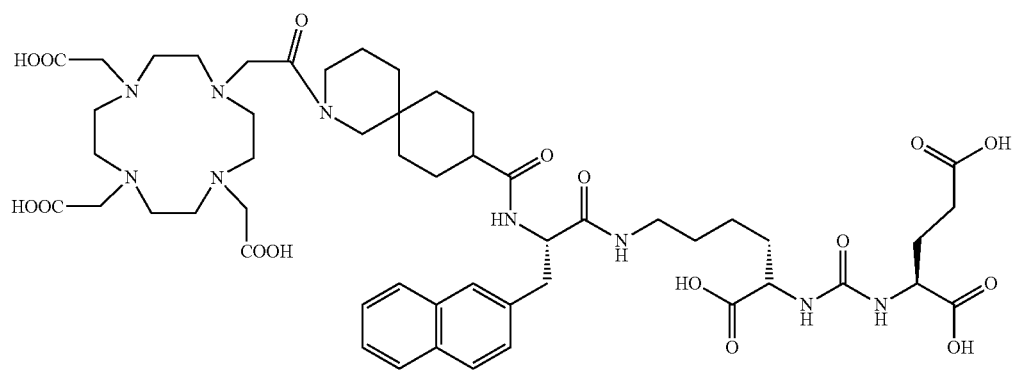
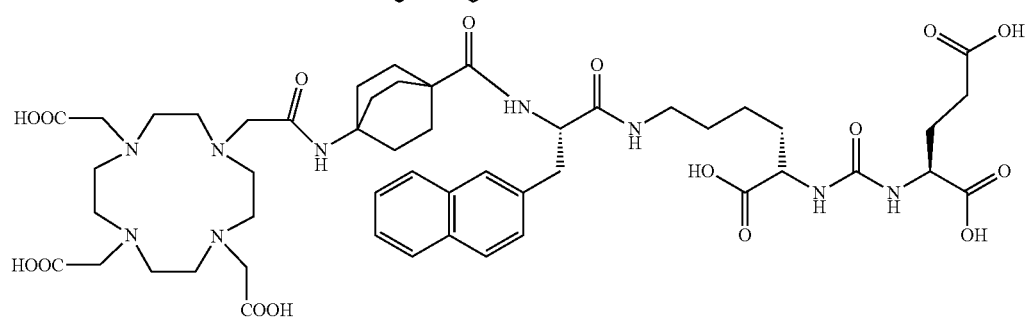
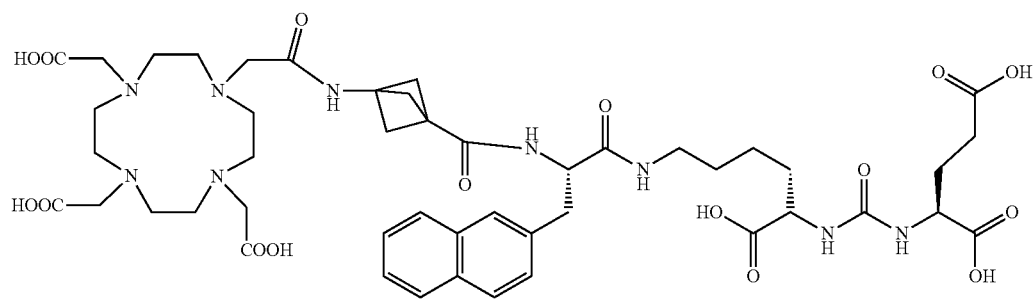
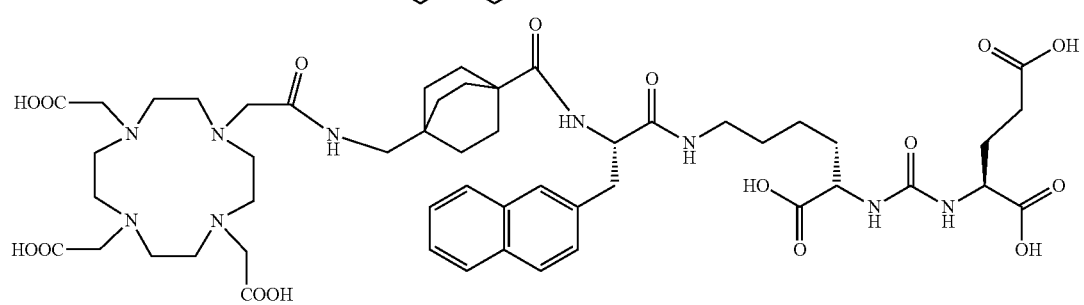

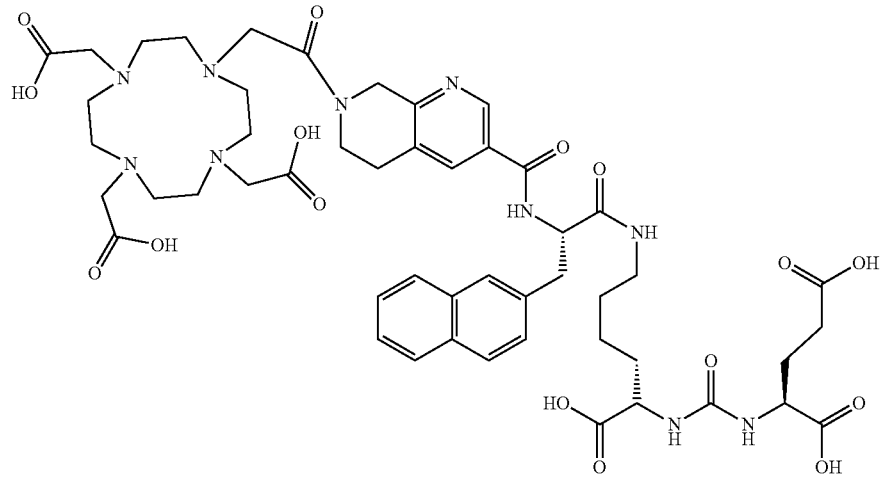
E16
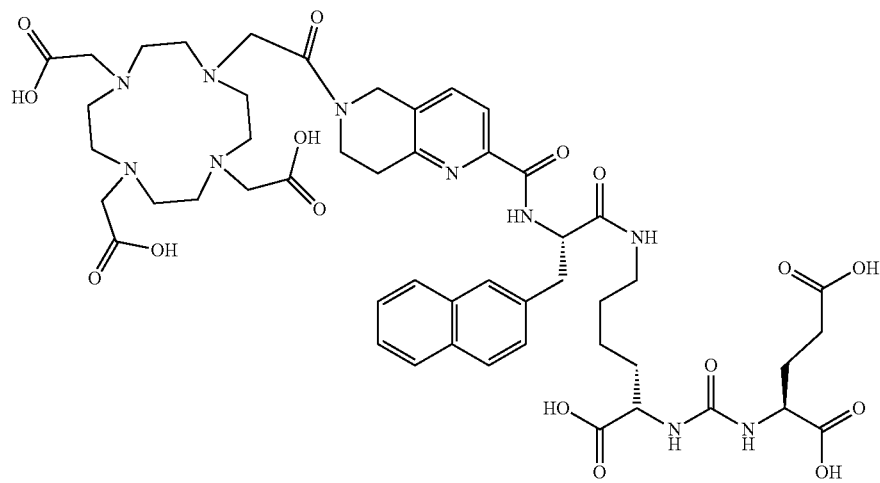
E17
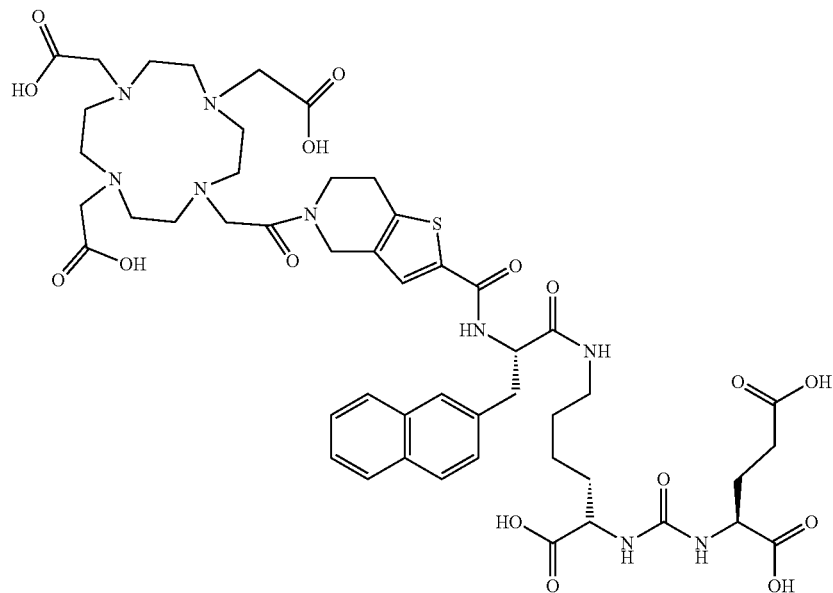
E18

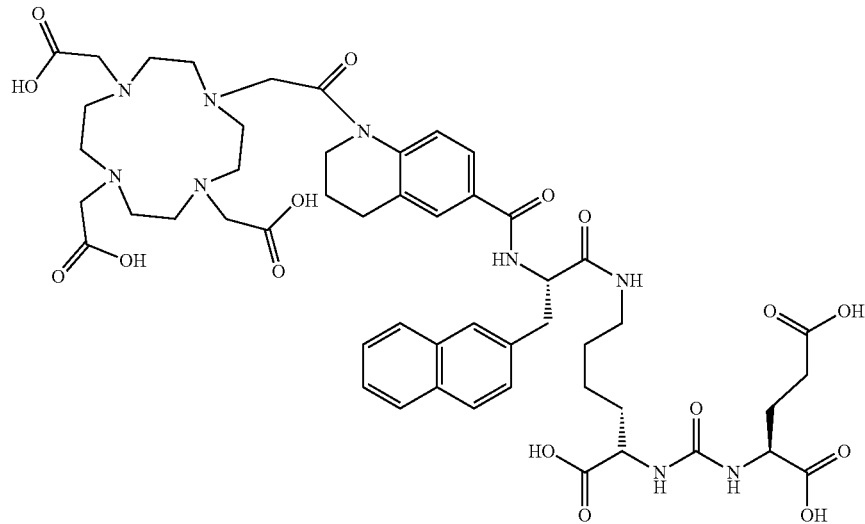
E19
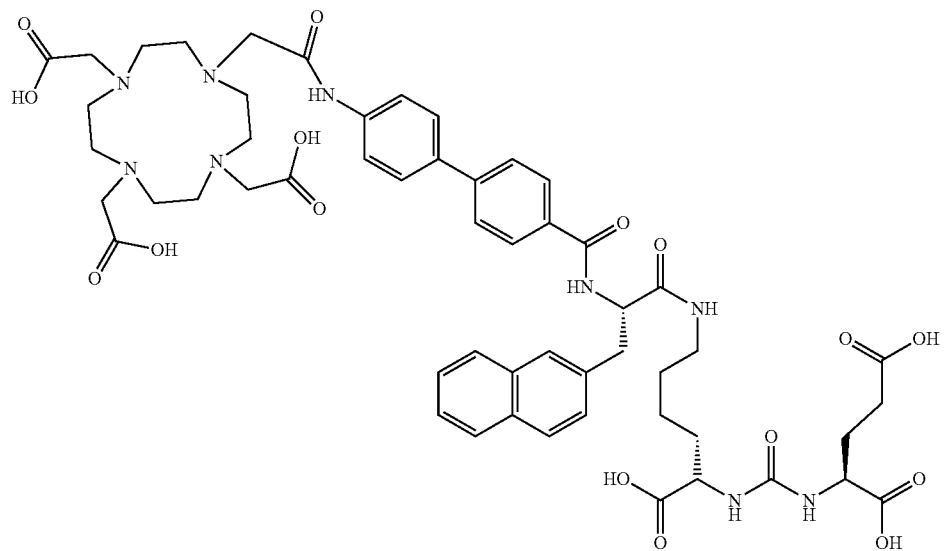
E20
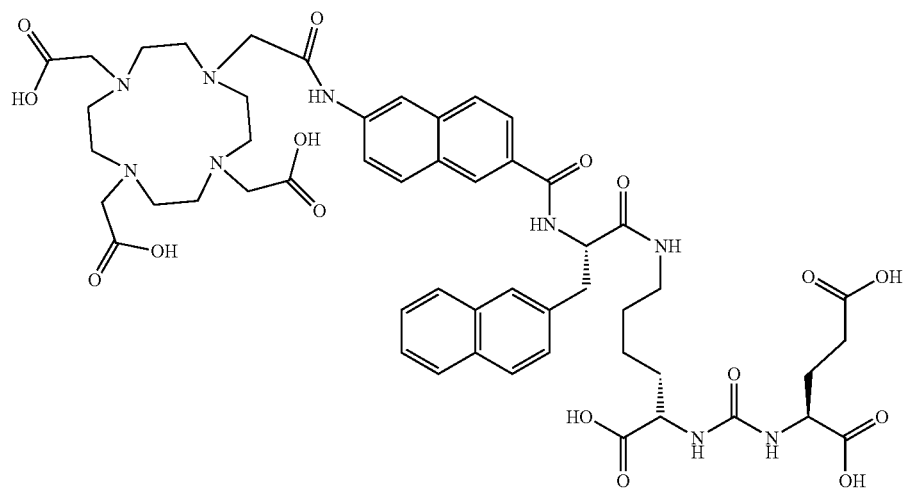
E21

-continued
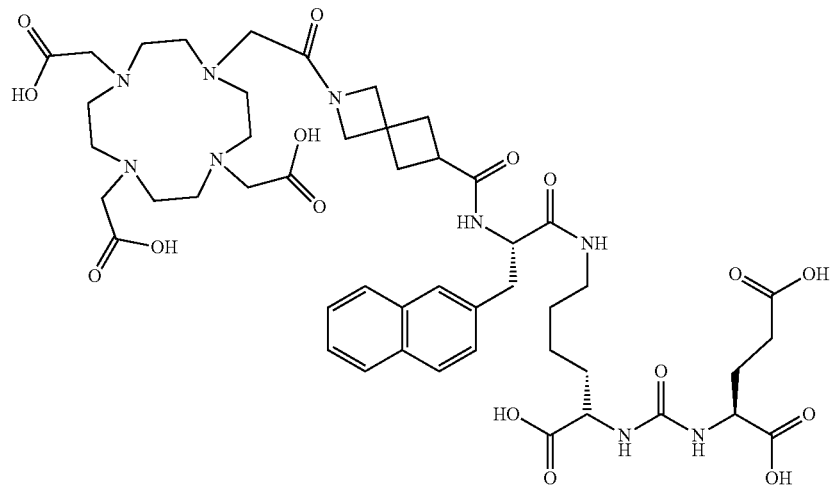
E22
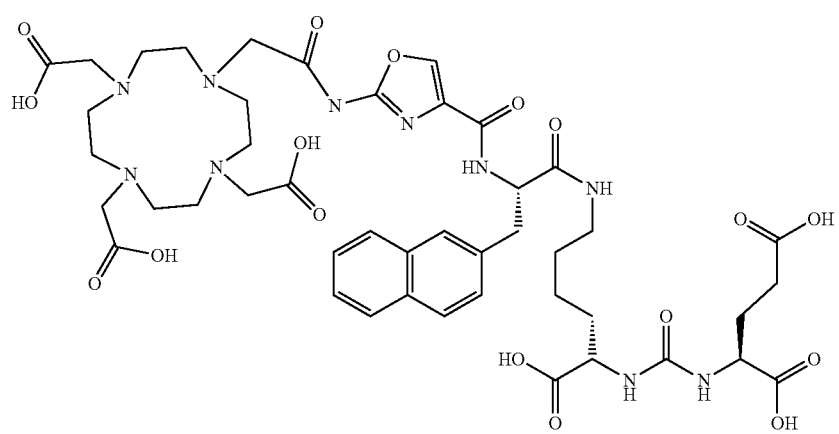
E23
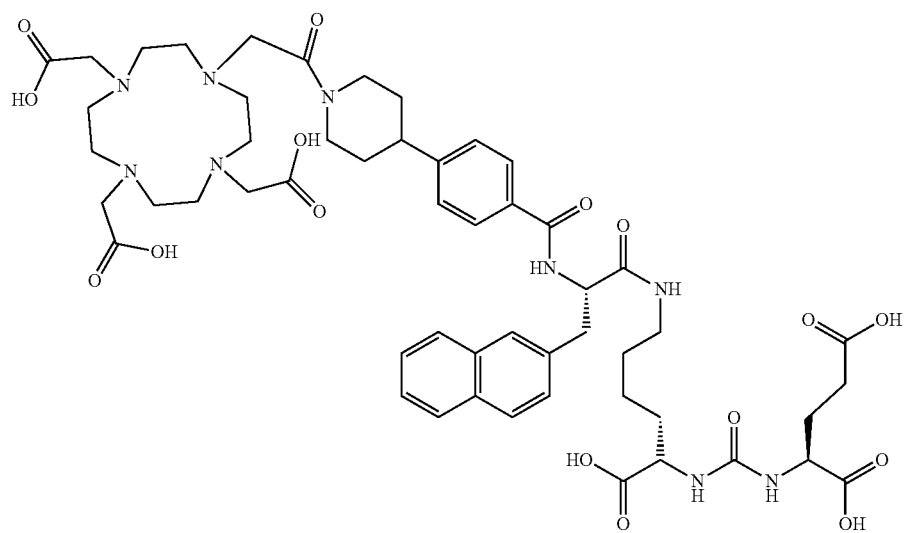
E24

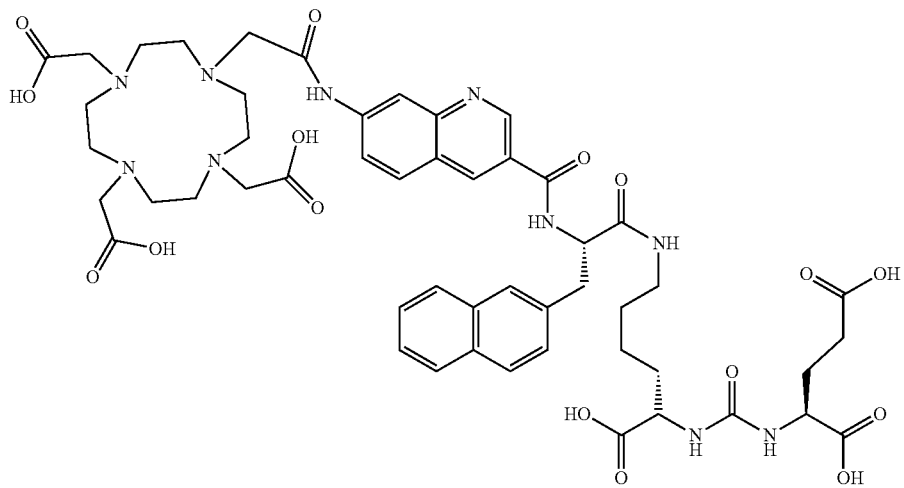

E25

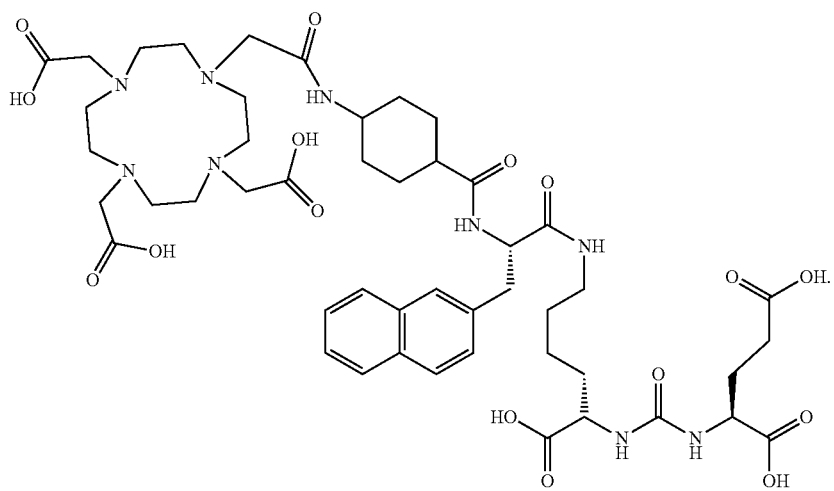

E26

The present disclosure also provides a pharmaceutical composition, which comprises substance X and a pharmaceutical adjuvant; wherein the substance X is the above-mentioned peptide-urea derivative of formula I, a pharmaceutically acceptable salt thereof, and a solvate thereof or a solvate of a pharmaceutically acceptable salt thereof.

In a certain embodiment, the pharmaceutical adjuvant is one or more of DTPA (diethylenetriaminepentaacetic acid), ascorbic acid, sodium ascorbate and water; more preferably, the pharmaceutical adjuvant is selected from DTPA, ascorbic acid, sodium ascorbate and water.

In a certain embodiment, the pharmaceutical composition is a pharmaceutical composition for treating or diagnosing prostate cancer.

In a certain embodiment, the pharmaceutical composition is a pharmaceutical composition for imaging prostate cancer.

In a certain embodiment, the prostate cancer is castration-resistant prostate cancer.

In a certain embodiment, the prostate cancer is metastatic castration-resistant prostate cancer.

In a certain embodiment, the prostate cancer is PSMA-positive prostate cancer.

In a certain embodiment, the substance X is a therapeutically effective amount of substance X.

The present disclosure also provides use of a substance X in the manufacture of a medicament; wherein the substance X is the above-mentioned peptide-urea derivative of formula I, a pharmaceutically acceptable salt thereof, and a solvate thereof or a solvate of a pharmaceutically acceptable salt thereof;

the medicament is a medicament for treating or diagnosing prostate cancer, or the medicament is a medicament for imaging prostate cancer.

In a certain embodiment, the medicament is a medicament for treating prostate cancer, and the radioactive metal ion is a radioactive metal ion that releases γ-rays.

In a certain embodiment, the medicament is a medicament for treating prostate cancer, and the radioactive metal ion is $^{177}Lu^{3+}$.

In a certain embodiment, the medicament is a medicament for diagnosing prostate cancer, and the radioactive metal ion is a radioactive metal ion that releases α or β rays.

In a certain embodiment, the medicament is a medicament for treating prostate cancer, and the radioactive metal ion is $^{225}Ac^{3+}$.

In a certain embodiment, the medicament is a medicament for diagnosing prostate cancer, and the radioactive metal ion is $^{68}Ga^{3+}$ or $Gd^{3+}$.

In a certain embodiment, the prostate cancer is castration-resistant prostate cancer.

In a certain embodiment, the prostate cancer is metastatic castration-resistant prostate cancer.

In a certain embodiment, the prostate cancer is PSMA-positive prostate cancer.

The term "pharmaceutically acceptable salt" refers to a salt obtained by reacting a compound with a pharmaceutically acceptable (relatively non-toxic, safe, and suitable for use by patients) acid or base. When a compound contains relatively acidic functional groups, base addition salts can be obtained by contacting the free form of the compound with a sufficient amount of a pharmaceutically acceptable base in a suitable inert solvent. Pharmaceutically acceptable base addition salts include, but not limited to, sodium salts, potassium salts, calcium salts, aluminum salts, magnesium salts, bismuth salts, ammonium salts, and the like. When a compound contains relatively basic functional groups, acid addition salts can be obtained by contacting the free form of the compound with a sufficient amount of a pharmaceutically acceptable acid in a suitable inert solvent. Pharmaceutically acceptable acid addition salts include, but not limited to, hydrochlorides, sulfates, methanesulfonates, acetates, trifluoroacetates, and the like. For details, see Handbook of Pharmaceutical Salts: Properties, Selection, and Use (P. Heinrich Stahl, 2002).

The term "solvate" refers to a substance formed after crystallization of a compound with a solvent (including but not limited to: water, methanol, ethanol, etc.). Solvates are divided into stoichiometric solvates and non-stoichiometric solvates.

The term "solvate of a pharmaceutically acceptable salt" refers to a substance formed by combining a compound with a pharmaceutically acceptable (relatively non-toxic, safe, and suitable for use by patients) acid or base, and solvent (including but not limited to: water, methanol, ethanol etc.), wherein the pharmaceutically acceptable salt has the same meaning as that of the term "pharmaceutically acceptable salt" above, and the solvent is stoichiometric or non-stoichiometric. Solvates of pharmaceutically acceptable salts include, but not limited to, hydrochloride monohydrate.

The term "alkyl" refers to straight-chain or branched-chain alkyl having a specified number of carbon atoms (e.g., $C_1$-$C_6$). Alkyls include but not limited to methyl, ethyl, n-propyl, isopropyl, n-butyl, tert-butyl, isobutyl, sec-butyl, n-pentyl, n-hexyl, n-heptyl, n-octyl, etc.

The term "cycloalkyl" or "carbocyclic ring" refers to a saturated cyclic group consisting only of carbon atoms with a specified number of carbon atoms (such as $C_3$-$C_6$), which is a monocyclic, bridged or spiro ring. Cycloalkyls include, but not limited to, cyclopropyl, cyclobutyl, cyclopentyl, cyclohexyl, and the like.

The term "heterocycloalkyl" or "carbon heterocyclic ring" refers to a cyclic group with a specified number of ring atoms (such as 5 to 10 members), a specified number of heteroatoms (such as 1, 2 or 3), and a specified type of heteroatoms (one or more of N, O and S), which is a monocyclic, bridged or spiro ring, and each ring is saturated. Heterocycloalkyls include, but not limited to, azetidinyl, tetrahydropyrrolyl, tetrahydrofuranyl, morpholinyl, piperidinyl, and the like.

The term "aryl" or "aromatic ring" refers to a cyclic group consisting only of carbon atoms with a specified number of carbon atoms (such as $C_6$-$C_{10}$), which is a monocyclic or fused ring, and at least one ring is aromatic (according to Huckel's rule). An aryl group is linked to other segments in the molecule through an aromatic ring or a non-aromatic ring. Aryl groups include, but not limited to, phenyl, naphthyl,

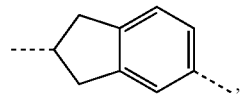

and the like.

The term "heteroaryl" or "heteroaromatic ring" refers to a cyclic group with a specified number of ring atoms (such as 5 to 10 members), a specified number of heteroatoms (such as 1, 2 or 3), and a specified type of heteroatoms (one or more of N, O and S), which is a monocyclic or fused ring, and at least one ring is aromatic (according to Huckel's rule). Heteroaryl groups are linked to other segments of the molecule through an aromatic ring or a non-aromatic ring in a fused ring. Heteroaryl groups include, but not limited to, furyl, pyrrolyl, thienyl, pyrazolyl, imidazolyl, oxazolyl, thiazolyl, pyridyl, pyrimidinyl, indolyl,

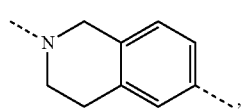

and the like.

The dashed line "⟶" in a structural fragment means that the structural fragment is linked to other fragments in the molecule through this site. For example

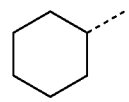

refers to cyclohexyl.

The term "pharmaceutical adjuvant" refers to excipients and additives used in the production of drugs and the preparation of prescriptions, and refers to all substances contained in pharmaceutical formulations except for active ingredients. For details, see Pharmacopoeia of the People's Republic of China (2020 Edition) or Handbook of Pharmaceutical adjuvants (Raymond C Rowe, 2009).

The term "therapeutically effective amount" refers to the amount of compound or the dose of radiation administered to a patient sufficient to effectively treat a disease. A therapeutically effective amount will vary according to the compound, the type of disease, the severity of disease, the age of patient, etc., but can be adjusted by those skilled in the art as appropriate.

The term "patient" refers to any animal, preferably a mammal, most preferably a human, who has been or is about to be treated. Mammals include, but not limited to, cows, horses, sheep, pigs, cats, dogs, mice, rats, rabbits, guinea pigs, monkeys, humans, and the like.

The term "treatment", "treating", or "treat" refers to any of the following: (1) amelioration of one or more biological manifestations of a disease; (2) interference with one or more points in the biological cascade leading to a disease; (3) slowing down of the development of one or more biological manifestations of a disease.

The term "prevention" or "prophylaxis" refers to reducing the risk of developing a disease.

The following abbreviations are used in the present disclosure:

DMF represents N,N-dimethylformamide.

DMAP represents 4-dimethylaminopyridine.

Fmoc represents a 9-fluorenylmethoxycarbonyl protecting group.

H-Glu(OtBu)-OH represents L-glutamic acid-5-tert-butyl ester.

Lys represents L-lysine.

Dde represents 1-(4,4-dimethyl-2,6-dioxocyclohexylene)ethyl.

DOTA represents 1,4,7,10-tetraazacyclododecane-1,4,7,10-tetraacetic acid.

HATU represents 2-(7-azabenzotriazole)-N,N,N',N'-tetramethyluronium hexafluorophosphate.

TCEP represents tris(2-hydroxyethyl)phosphine.

On the basis of not violating common knowledge in the field, the above-mentioned preferred conditions can be combined arbitrarily to obtain preferred examples of the present disclosure.

Reagents and raw materials commonly used in the present disclosure are commercially available or prepared by using commercially available raw materials through reactions well known to those skilled in the art.

The advantages of the present disclosure are as follow: the derivatives presented in this disclosure overcome the shortcomings of so far reported compounds of the same kind; after entering the animal body, the uptake and residence time of disclosed derivatives on non-target organs such as kidney are greatly reduced, while the uptake and residence time on targeted cancer cells are significantly increased. The derivatives included in the present disclosure can be used not only for the diagnosis and grading of PSMA-positive prostate cancer via imaging before surgery, but also for the treatment of prostate cancer of various types and stages, achieving the integration of diagnosis and treatment. The derivatives included in the present disclosure have a wide application prospect.

DETAILED DESCRIPTION OF THE EMBODIMENTS

Figure 1:
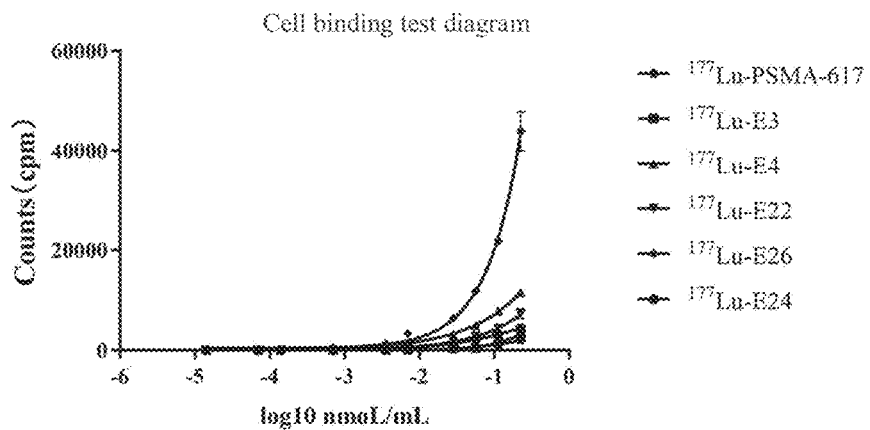
FIG. 1 shows the cell binding test of effect example 5.

The present disclosure is further illustrated below by means of examples, but the present disclosure is not limited to the scope of the examples. For the experimental methods that do not emphasize specific conditions in the following examples, the methods and conditions are selected based on conventional methods and conditions, or based on the instructions of commercial products.

Synthesis of Intermediate Compound M1

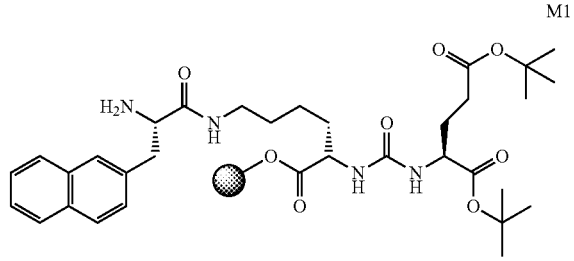

General synthetic method A: Fmoc-Lys(Dde)-Wang resin (0.3 mmol/g) was used as a raw material, and added into a reaction vessel. 25% piperidine/DMF (volume ratio) was then added, and the mixture was stirred for 30 min. Ninhydrin detection showed dark blue. The reaction solution was dried by suction, filtered, and washed 5 times with DMF. The N-terminal Fmoc protecting group was removed to make the N-terminal a free amino group; DMF was used as a solvent, and N,N-disuccinimidyl carbonate (1 equivalent), N,N-diisopropylethylamine DIPEA (2 equivalent) and 4-dimethylaminopyridine DMAP (2 equivalent) were added in a proportion (1:2:2). The mixture was reacted under the protection of nitrogen for 1 h. H-Glu(OtBu)-OH (1.1 equivalent) was then added, and the mixture was stirred for 24 hours. The Dde protecting group of the side chain of Lys was then removed with 2% hydrazine hydrate/DMF solution, and then Fmoc-2-Nal-OH/HOBt/DIC (3 equivalents) was added to graft the resin to introduce 2-Nal amino acid residue. Subsequently, 25% piperidine/DMF (volume ratio) was used to remove the Fmoc protecting group again so that the N-terminus of 2-Nal became a free amino group, and the product M1 was synthesized.

The Synthetic Method of Intermediate Compound M2:

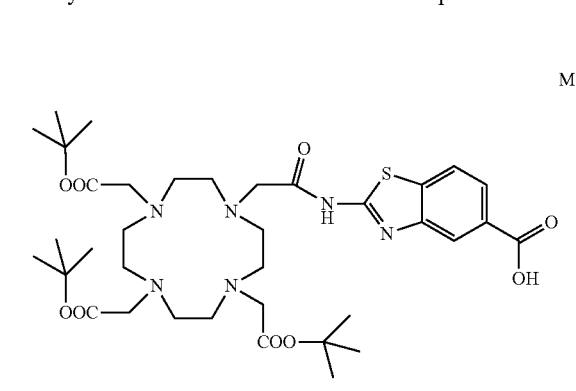

M2

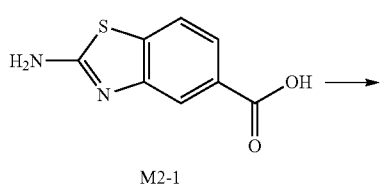

M2-1

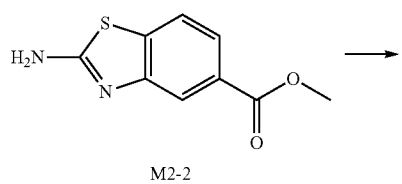

M2-2

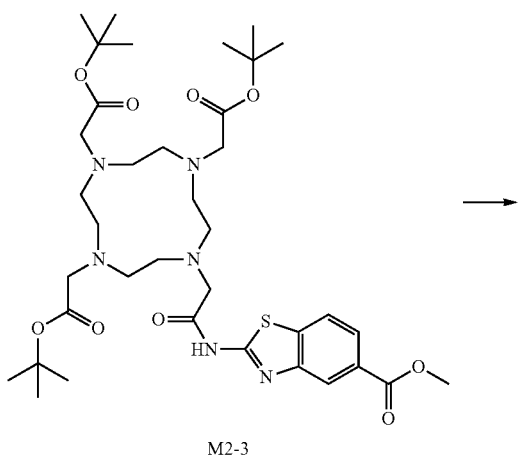

M2-3

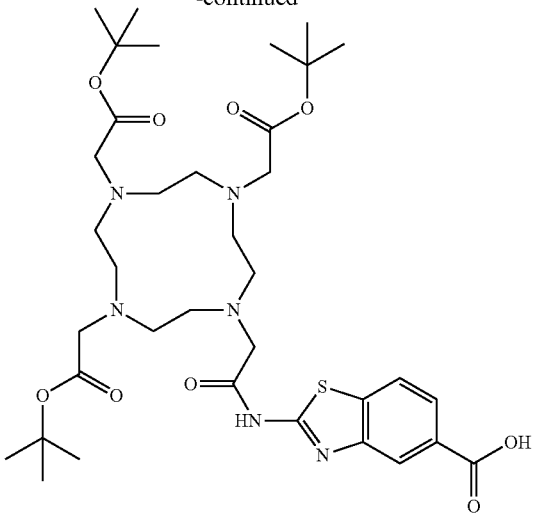

M2

Synthesis of Intermediate M2-2:

Compound M2-1 (250 mg, 1.29 mmol), and TMSCH$_2$N$_2$ (445 mg, 3.86 mmol) were added dropwise to MeOH (10 ml), and the reaction mixture was stirred at room temperature in a 100 mL round bottom flask for 2 hours. LCMS monitored the completion of the reaction. The reaction mixture was poured into water (50 mL) to quench the reaction, and the mixture was extracted with ethyl acetate (50 mL×3). The organic phases were combined. The combined organic phase was washed with saturated sodium chloride (50 mL×1), dried over sodium sulfate, and filtered. The filtrate was concentrated. The crude product was purified by a thick preparative plate to give the compound M2-2 (200 mg, 74.6%).

Synthesis of Intermediate M2-3:

Compound M2-2 (200 mg, 0.96 mmol), HATU (2-(7-azabenzotriazole)-N,N,N',N'-tetramethyluronium hexafluorophosphate) (437 mg, 1.15 mmol) and DIEA (N,N-diisopropylethylamine) (247 mg, 1.92 mmol) were added to DCM (5 mL), and the reaction was stirred at room temperature in a 100 mL round bottom flask for 5 min. Compound DOTA (549 mg, 0.96 mmol) was then added, and the reaction mixture was stirred at this temperature for another 1 h. LCMS monitored the completion of the reaction. The reaction mixture was poured into water (50 mL) to quench the reaction, and the mixture was extracted with DCM (50 mL×3). The organic phases were combined. The combined organic phase was washed with saturated sodium chloride (50 mL×1), dried over sodium sulfate, and filtered. The filtrate was concentrated. The crude product was purified by a thick preparative plate to give the compound M2-3 (500 mg, 68.23%).

Synthesis of Intermediate M2:

Compound M2-3 (500 mg, 0.655 mmol) and LiOH (32 mg, 1.31 mmol) were added to MeOH (8 ml)/H$_2$O (2 mL), and the reaction was stirred at room temperature in a 100 mL round bottom flask for 2 hrs. LCMS monitored the completion of the reaction. The reaction mixture was poured into water (50 mL) to quench the reaction, and the mixture was extracted with EtOAc (50 mL×3). The organic phases were combined. The combined organic phase was washed with saturated sodium chloride (50 mL×1), dried over sodium sulfate, and filtered.

The filtrate was concentrated. The crude product was purified by a thick preparative plate and then purified by pre-HPLC to give the compound M2 (60 mg, 12.2%); $^1$H NMR (400 MHz, DMSO-d$_6$) δ 13.13-12.51 (brs, 1.0H), δ 8.24 (d, J=1.2 Hz, 1H), 8.04 (d, J=8.3 Hz, 1H), 7.84 (dd, J=8.3, 1.5 Hz, 1H), 3.42 (d, J=16.5 Hz, 8H), 2.94-2.66 (m, 17H), 1.31 (s, 27H). LCMS: [M−1]$^+$=747.4.

The following intermediates were synthesized by the synthetic method of the above-mentioned intermediate M2:

B3

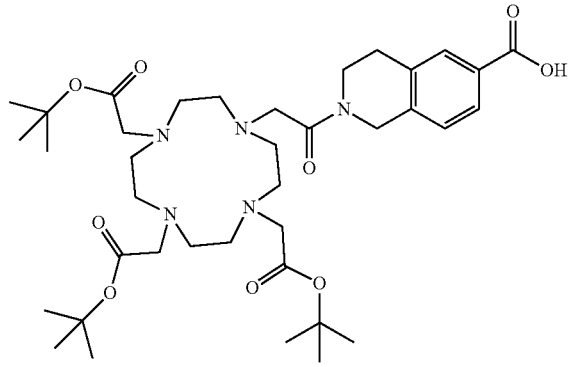

B3 (820 mg, 28.5%) was obtained by using the synthetic method of general intermediate M2, MS: [M+1]$^+$=683.5.

B4

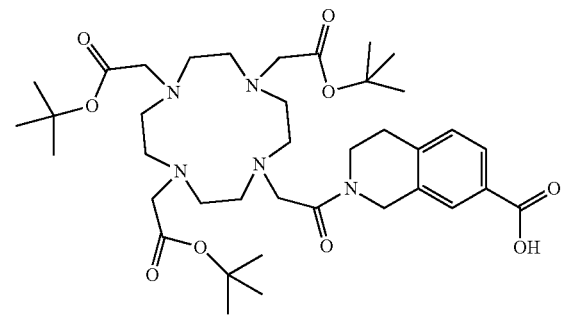

B4 (568 mg, 35.8%) was obtained by using the synthetic method of general intermediate M2, MS: [M+1]$^+$=683.5.

B6

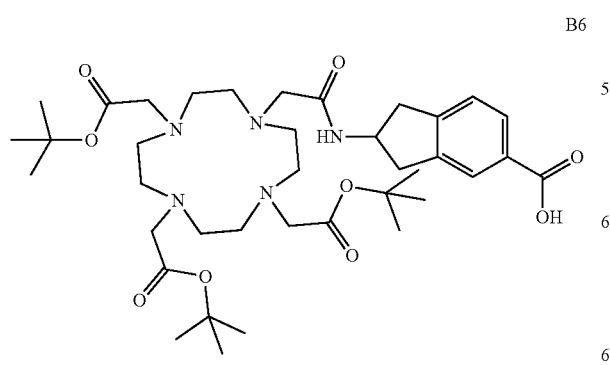

B6 (768 mg, 39%) was obtained by using the synthetic method of general intermediate M2, MS: [M+1]$^+$=683.5.

B11

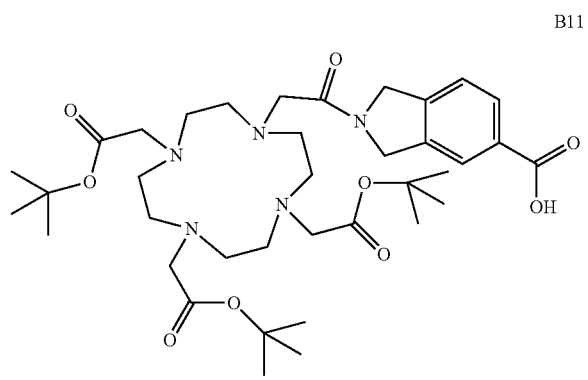 [SMILES: CC(C)(C)OC(=O)CN1CCN(CC(=O)OC(C)(C)C)CCN(CC(=O)N2Cc3ccc(C(=O)O)cc3C2)CCN(CC(=O)OC(C)(C)C)CC1]

B11 (368 mg, 26%) was obtained by using the synthetic method of general intermediate M2, MS: [M+1]$^+$=683.5.

B17

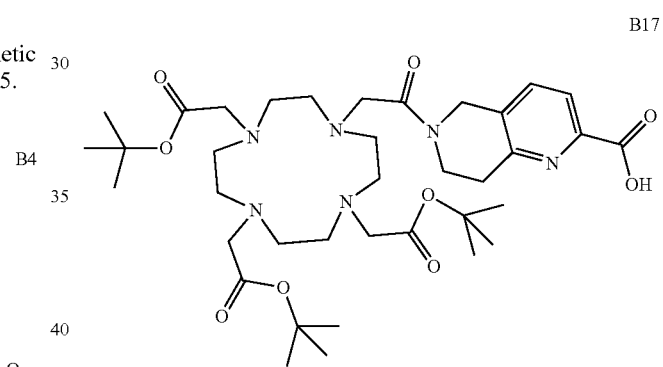

B17 (612 mg, 29.9%) was obtained by using the synthetic method of general intermediate M2, MS: [M+1]$^+$=683.5.

B18

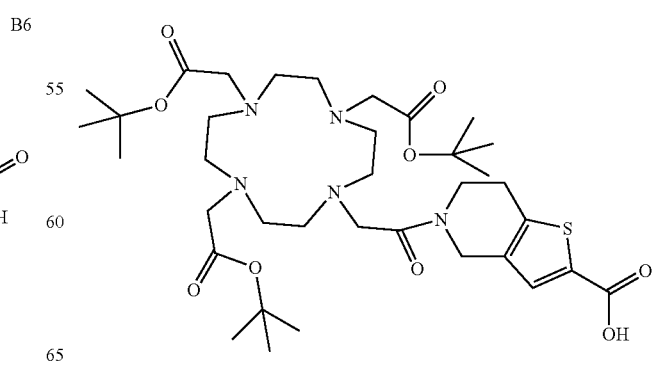

B18 (712 mg, 30.9%) was obtained by using the synthetic method of general intermediate M2, MS: [M+1]$^+$=683.5.

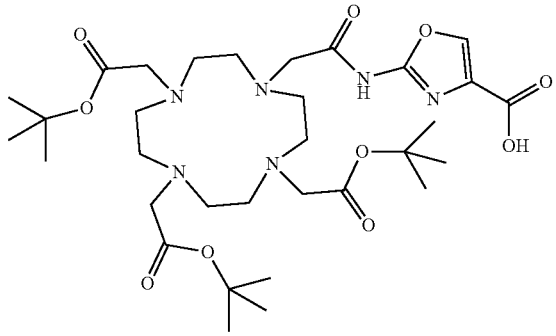

B23

B23 (568 mg, 37.9%) was obtained by using the synthetic method of general intermediate M2, MS: [M+1]$^+$=683.5

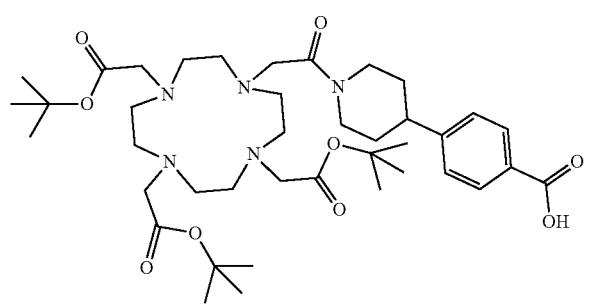

B24

B24 (658 mg, 45.9%) was obtained by using the synthetic method of general intermediate M2, MS: [M+1]$^+$=761.1

Synthesis of Intermediate Compounds Protected by Fmoc

General synthetic method B: Compound Fomc-Osu (1 equivalent) and amino-containing compound (1 equivalent) were dissolved in 1,4-dioxane (4 mL) and water (2 mL), and sodium carbonate (1.85 equivalent) was added. The mixture was stirred at room temperature for 10 h. TLC result showed that the raw materials were consumed completely. The solvent was removed by suction under reduced pressure. The pH was adjusted to 3-4 by adding 0.1 mol/L NH$_4$Cl solution, and the mixture was extracted twice with EtOAc. The organic phase was dried and concentrated, and the crude product was purified by pre-HPLC to give the corresponding Fmoc-protected compound.

M3

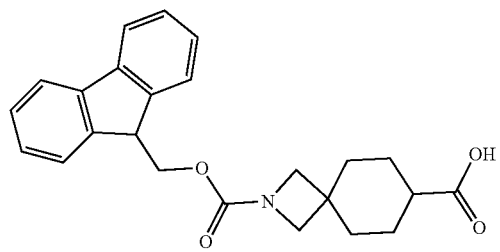

M3 was obtained by using general synthetic method B (168 mg, 57.9%); $^1$H NMR (400 MHz, DMSO-d$_6$) δ 12.08 (s, 1H), 7.89 (d, J=7.5 Hz, 2H), 7.63 (d, J=7.4 Hz, 2H), 7.42 (t, J=7.3 Hz, 2H), 7.34 (td, J=7.4, 0.9 Hz, 2H), 4.31 (d, J=6.7 Hz, 2H), 4.23 (t, J=6.7 Hz, 1H), 3.50 (d, J=17.9 Hz, 4H), 2.16 (s, 1H), 1.75 (t, J=10.3 Hz, 4H), 1.39 (ddd, J=28.9, 17.8, 6.8 Hz, 4H); LCMS: [M−1]$^+$=390.2.

M4

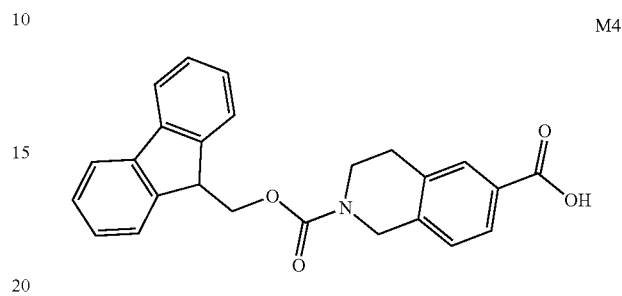

Compound M4 (107 mg, 97.7%) was obtained by using general synthetic method B; $^1$H NMR (400 MHz, DMSO-d$_6$) δ 13.18-12.22 (m, 1H), 7.78 (dd, J=76.9, 28.8 Hz, 6H), 7.46-7.16 (m, 5H), 4.54 (s, 2H), 4.42 (d, J=6.2 Hz, 2H), 4.31 (t, J=6.2 Hz, 1H), 3.52 (s, 2H), 2.75 (s, 2H); LCMS: [M−1]$^+$=398.1.

M5

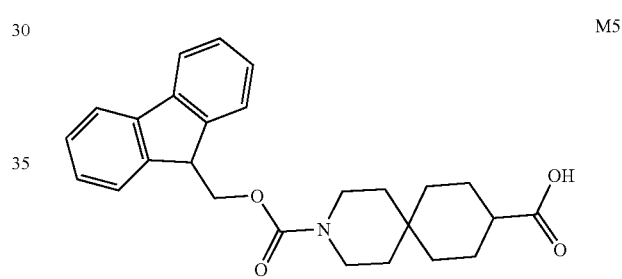

Compound M5 (150 mg, 98.2%) was obtained by using general synthetic method B; $^1$H NMR (400 MHz, DMSO-d$_6$) δ 12.45-11.54 (m, 1H), 7.90 (d, J=7.5 Hz, 2H), 7.63 (d, J=7.4 Hz, 2H), 7.41 (d, J=7.4 Hz, 2H), 7.35 (dd, J=7.4, 0.7 Hz, 2H), 4.39 (d, J=6.3 Hz, 2H), 4.27 (d, J=6.2 Hz, 1H), 3.28-3.19 (m, 4H), 2.16 (ddd, J=14.8, 7.5, 3.8 Hz, 1H), 1.63 (ddd, J=23.0, 12.6, 8.8 Hz, 4H), 1.513-1.421 (m, 2H), 1.28-1.05 (m, 6H); LCMS: [M−1]$^+$=418.2.

M6

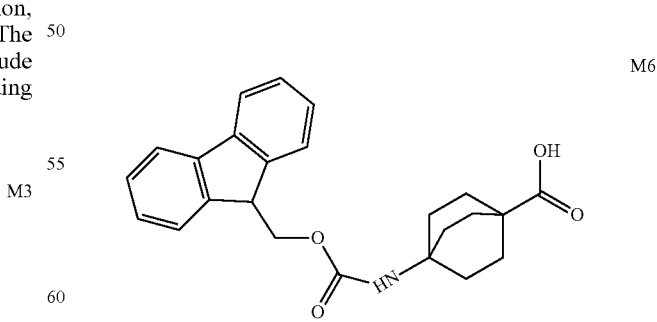

Compound M6 (168 mg, 57.91%) was obtained by using general synthetic method B; $^1$H NMR (400 MHz, DMSO-d$_6$) δ 11.99 (s, 1H), 7.88 (d, J=7.5 Hz, 2H), 7.69 (d, J=7.3 Hz, 2H), 7.41 (t, J=7.2 Hz, 2H), 7.32 (t, J=7.0 Hz, 2H), 7.02 (s, 1H), 4.19 (s, 3H), 1.75 (s, 12H); LCMS: [M−1]$^+$=390.1.

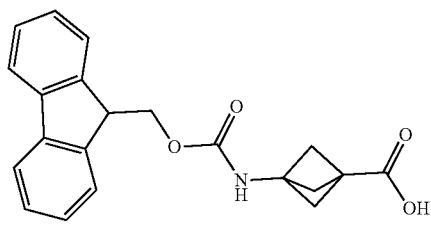

M7

Compound M7 (121 mg, 98.7%) was obtained by using general synthetic method B; ¹H NMR (400 MHz, DMSO-$d_6$) δ 8.08 (s, 1H), 7.88 (d, J=7.5 Hz, 2H), 7.67 (d, J=7.1 Hz, 2H), 7.41 (t, J=7.4 Hz, 2H), 7.33 (td, J=7.4, 1.0 Hz, 2H), 4.24 (d, J=27.0 Hz, 3H), 2.08 (t, J=18.1 Hz, 5H), 1.58 (s, 1H), 1.23 (s, 1H); LCMS: [M−1]⁺=348.2.

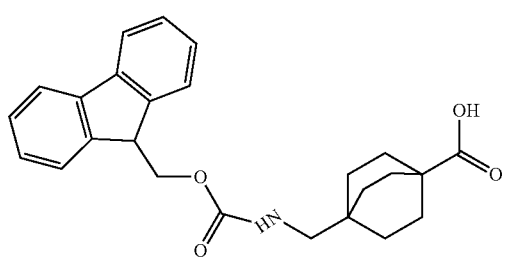

M8

Compound M8 (151 mg, 89.9%) was obtained by using general synthetic method B; ¹H NMR (400 MHz, DMSO-$d_6$) δ 11.99 (s, 1H), 7.88 (d, J=7.5 Hz, 2H), 7.69 (d, J=7.3 Hz, 2H), 7.41 (t, J=7.2 Hz, 2H), 7.32 (t, J=7.0 Hz, 2H), 7.02 (s, 1H), 4.19 (s, 3H), 2.89 (d, J=2.7 Hz, 2H), 1.75 (s, 12H); LCMS: [M−1]⁺=404.2.

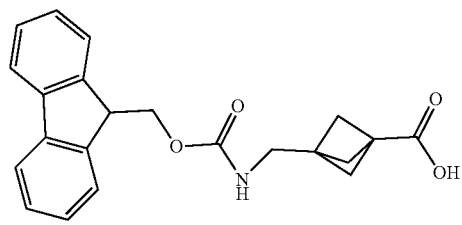

M9

Compound M9 (110 mg, 56.7%) was obtained by using general synthetic method B; ¹H NMR (400 MHz, DMSO-$d_6$) δ 8.08 (s, 1H), 7.88 (d, J=7.5 Hz, 2H), 7.67 (d, J=7.1 Hz, 2H), 7.41 (t, J=7.4 Hz, 2H), 7.33 (td, J=7.4, 1.0 Hz, 2H), 4.24 (d, J=27.0 Hz, 3H), 2.99 (d, J=2.7 Hz, 2H) 2.08 (t, J=18.1 Hz, 5H), 1.58 (s, 1H), 1.23 (s, 1H); LCMS: [M−1]⁺= 362.2.

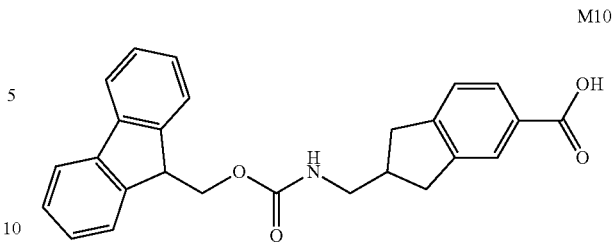

M10

Compound M10 (1155 mg, 63.3%) was obtained by using general synthetic method B; ¹H NMR (400 MHz, DMSO-$d_6$) δ 13.18-12.22 (m, 1H), 7.78 (dd, J=76.9, 28.8 Hz, 6H), 7.46-7.16 (m, 5H), 4.54 (s, 2H), 3.17 (d, J=1.37 Hz, 2H), 2.75 (d, J=6.2 Hz, 2H), 2.73 (t, J=6.2 Hz, 2H), 1.99 (m, 1H).

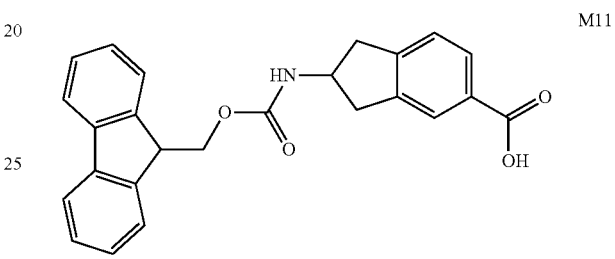

M11

Compound M11 (165 mg, 86.7%) was obtained by using general synthetic method B; MS: [M−1]⁺=398.2.

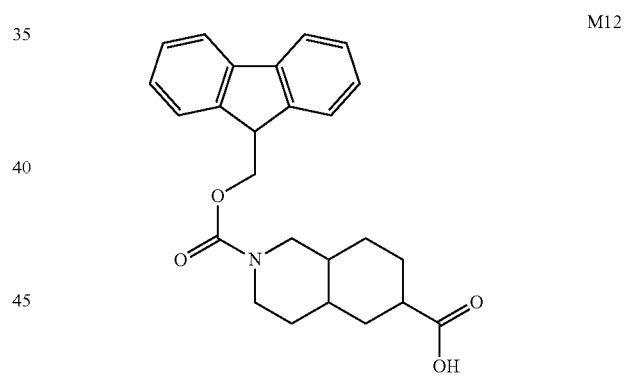

M12

Compound M12 (210 mg, 76.5%) was obtained by using general synthetic method B; MS: [M−1]⁺=404.2.

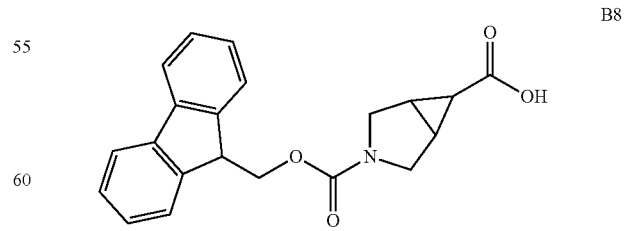

B8

Compound B8 (820 mg, 65%) was obtained by using general synthetic method B; 1H NMR (400 MHz, CDCl³) δ 7.77 (d, J=7.6 Hz, 2H), 7.61 (d, J=7.6 Hz, 2H), 7.37 (t, J 7.6 Hz, 2H), 7.28 (t, J=7.6 Hz, 2H), 4.31-4.45 (m, 2H), 4.18-

4.22 (m, 1H), 3.68-3.75 (m, 1H), 3.61-3.71 (m, 1H), 3.48-3.58 (m, 2H), 2.16-2.21 (m, 2H), 1.45-1.48 (m, 1H). MS: [M+1]⁺=350.1.

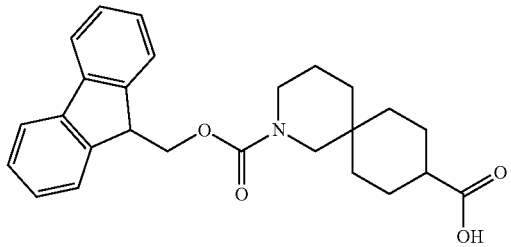
B12

Compound B12 (210 mg, 76.5%) was obtained by using general synthetic method B; ¹HNMR (400 MHZ, DMSO-d₆) δ 12.02 (s, 1H), 7.89 (d, J=7.6 Hz, 2H), 7.62 (d, J=7.6 Hz, 2H), 7.41 (d, J=7.6 Hz, 2H), 7.33 (d, J=7.6 Hz, 2H), 4.33-4.52 (m, 2H), 4.22-4.31 (m, 1H), 3.18-3.25 (m, 4H), 2.02-2.21 (m, 1H), 1.16-1.68 (m, 12H). MS: [M+1]⁺=420.

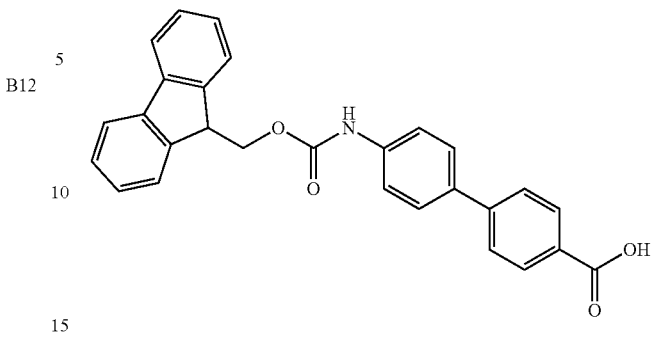
B20

Compound B20 (450 mg, 79%) was obtained by using general synthetic method B, 1H NMR (400 MHz, DMSO-d₆) δ 12.99 (s, 1H), 9.88 (s, 1H), 7.21-8.02 (m, 16H), 4.30-4.61 (m, 2H), 4.25-4.30 (m, 1H); MS: [M+1]⁺=436.2.

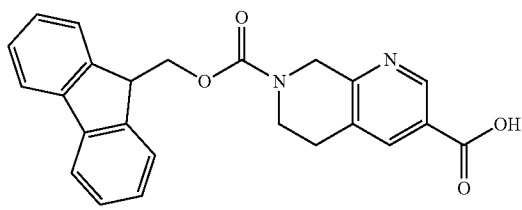
B16

Compound B16 (300 mg, 79%) was obtained by using general synthetic method B, MS: [M+1]⁺=401.1.

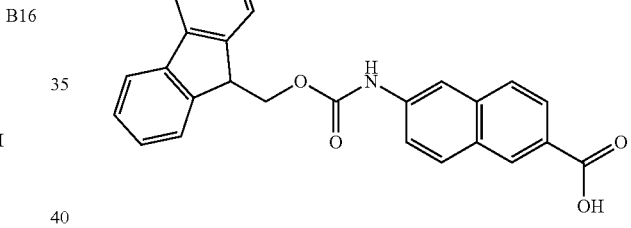
B21

Compound B21 (500 mg, 87%) was obtained by using general synthetic method B. 1H NMR (400 MHz, DMSO-d₆) δ 12.92 (s, 1H), 10.12 (s, 1H), 8.5 (s, 1H), 8.13 (s, 1H), 7.71-8.12 (m, 4H), 7.50-7.69 (m, 1H), 7.30-7.49 (m, 4H), 4.45-4.58 (m, 2H), 4.31-4.40 (m, 1H); MS: [M+1]⁺=410.2.

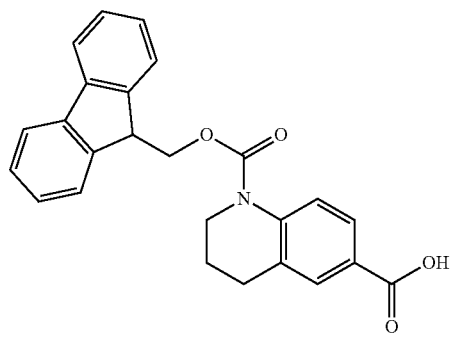
B19

Compound B19 (300 mg, 80%) was obtained by using general synthetic method B, ¹H NMR (400 MHz, DMSO-d₆) δ 12.71 (s, 1H), 7.91 (d, J=8.0 Hz, 2H), 7.65 (d, J=8.0 Hz, 2H), 7.42 (t, J=12 Hz, 2H), 7.33 (t, J=8.0 Hz, 2H), 7.21 (br s, 1H), 4.69 (d J=8.0 Hz, 2H), 4.35 (s, 1H), 3.49-3.56 (m, 2H), 2.52-2.77 (m, 2H), 1.65-1.79 (m, 2H), MS: [M+1]⁺=400.1.

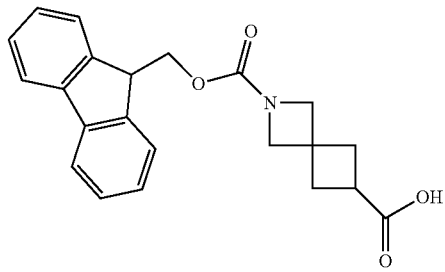
B22

Compound B22 (300 mg, 75%) was obtained by using general synthetic method B. ¹H NMR (400 MHZ, DMSO-d₆) δ 12.11 (br s, 1H), 7.89 (d, J=7.5 Hz, 2H), 7.68 (d, J=7.3 Hz, 2H), 7.42 (t, J=7.2 Hz, 2H), 7.33 (t, J=7.0 Hz, 2H), 4.22-4.33 (m, 3H), 3.90 (s, 2H), 3.80 (s, 2H), 2.82-2.95 (m, 1H), 2.25-2.41 (m, 4H). MS: [M+1]⁺=364.3.

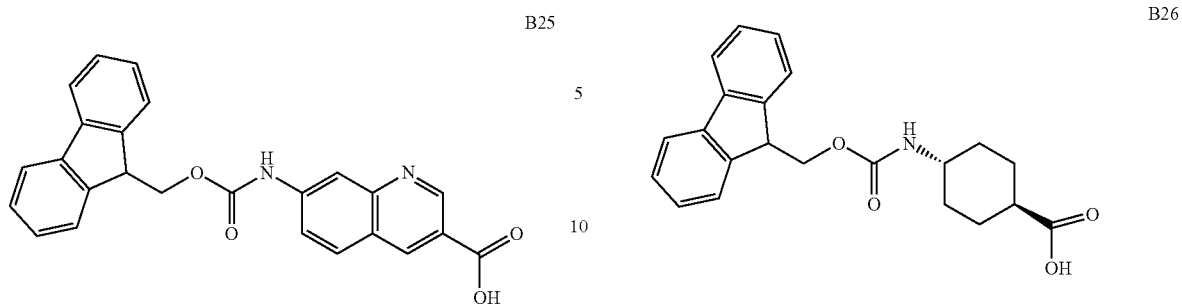

Compound B25 (620 mg, 67%) was obtained by using general synthetic method B, ¹H NMR (400 MHZ, DMSO-d₆) δ 12.32 (br s, 1H), 10.28 (s, 1H), 9.22 (s, 1H), 8.82 (s, 1H), 8.29 (s, 1H), 8.08 (d, J=9.2 Hz, 1H), 7.92 (d, J=7.6 Hz, 2H), 7.78 (d, J=7.2 Hz, 2H), 7.75-7.76 (m, 1H), 7.44 (t, J=7.2 Hz, 2H), 7.37 (t, J=7.2 Hz, 2H), 4.58 (d, J=6.4 Hz, 2H), 4.36 (t, J=6.8 Hz, 1H). MS: [M+1]⁺=411.1.

Compound B26 (700 mg, 81%) was obtained by using general synthetic method B, MS: [M+1]⁺=366.2.

General deprotection step for Fmoc protecting group: A solution of 5% piperidine, 1.25% DBU and 1% HOBt in DMF (v/v/w/v) (approximately 6 mL solution/g resin) was mixed with a resin and stirred at room temperature for 10 minutes. The mixture was filtered, and then the same solution was added and stirred at room temperature for 20 minutes. The mixture was filtered. The resin was then washed in the following order: 2×DMF, 2×MTBE, 2×DMF, and the resin was ready for use after washing.

Example 1. Synthesis of Compound E1

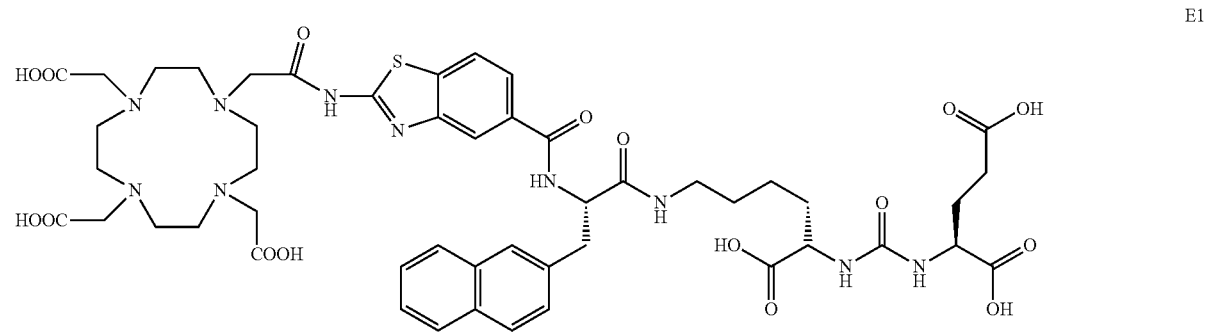

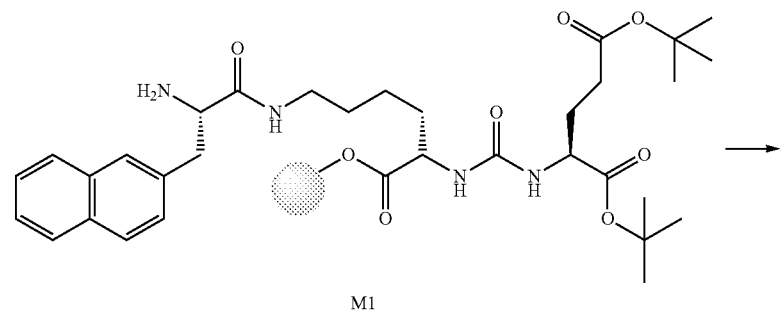

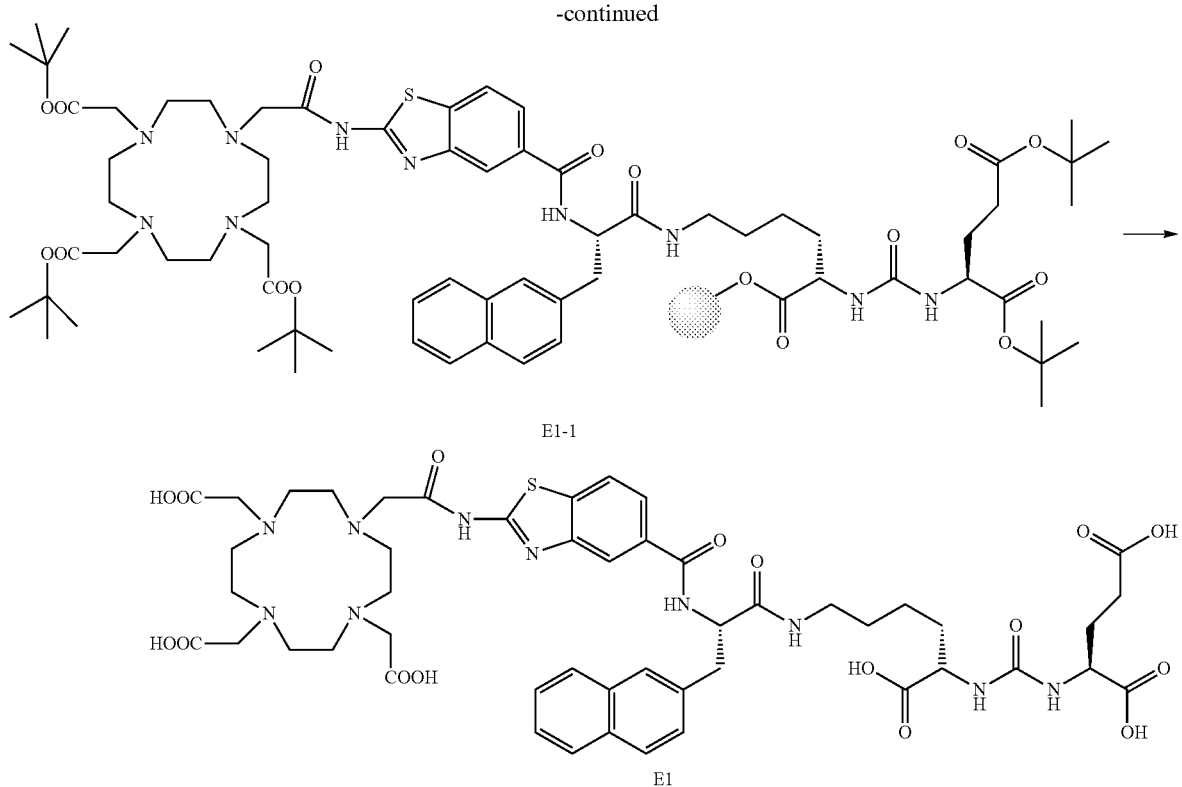

E1-1

E1

General synthetic method C:
1) Synthesis of intermediate E1-1:

The resin-loaded compound M1 and compound M2 were added to a reaction flask in an equal equivalent ratio. DMF was used as a solvent, and an equal equivalent of HOBt and DIC were respectively added for resin condensation coupling. The mixture was stirred at room temperature for 2.5 hours. The detection method was ninhydrin detection showing dark blue. After the completion of the reaction by monitoring, the reaction solution was filtered and washed 3-5 times with DMF to give intermediate E1-1, which was directly used in the next step.

2) Synthesis of Compound E1:

A cleavage reagent (trifluoroacetic acid:H₂O:triisopropylsilane=90:5:5, v/v) was used to cleave the target polypeptide from the compound E1-1 resin and remove the side chain protecting group (cleaving at 30° C. for 3 hours). The filtrate was added to a large amount of cold anhydrous diethyl ether to precipitate the polypeptide, and the mixture was centrifuged. The polypeptide was washed several times with diethyl ether and then dried to give the crude polypeptide. The crude product was purified by reverse-phase high-performance liquid chromatography to give compound E1. Column model: Agela C18 (10 m, 100 Å, 50×250 mm). Chromatographic operating conditions: mobile phase A was an aqueous solution containing 0.05% trifluoroacetic acid and 2% acetonitrile, mobile phase B was 90% acetonitrile aqueous solution, the flow rate was 25 milliliters per minute, and the ultraviolet detection wavelength was 220 nanometers. After freeze-drying the solvent, the pure peptide in a fluffy state was obtained. The chemical structure was characterized by MALDI-TOF mass spectrometry, and the purity was determined by analytical high-performance liquid chromatography (Agela C18-10×250 mm, flow rate: 1 ml per minute). MS: [M+2]⁺=1080.3, [M+Na]⁺=1102.4.

Example 2. Synthesis of Compound E2

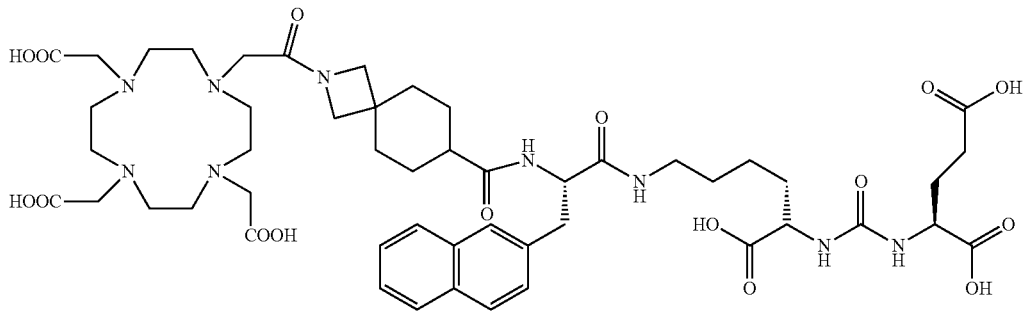

E2

-continued
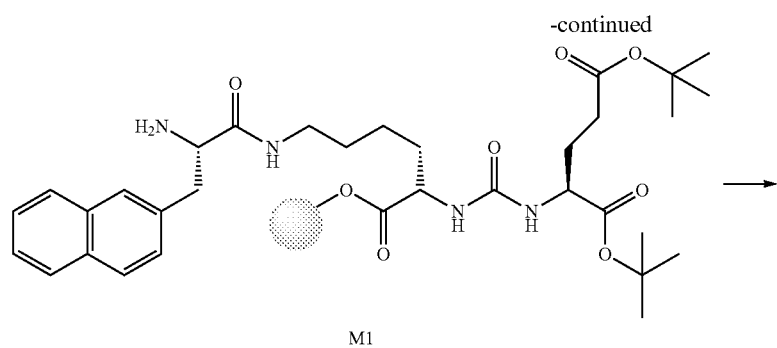
M1
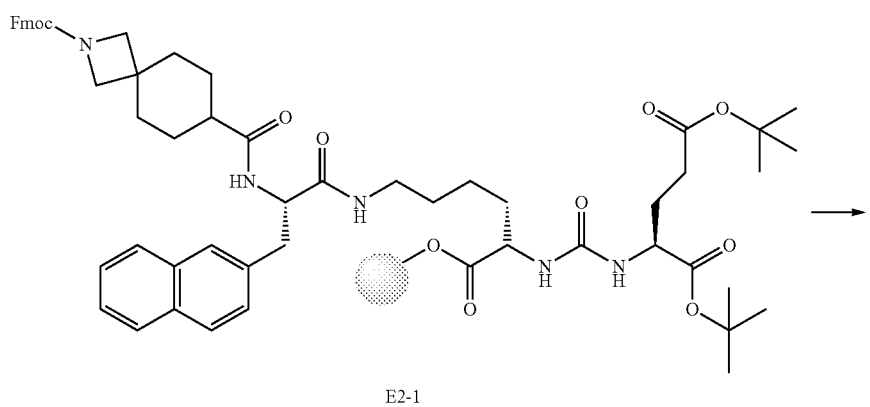
E2-1
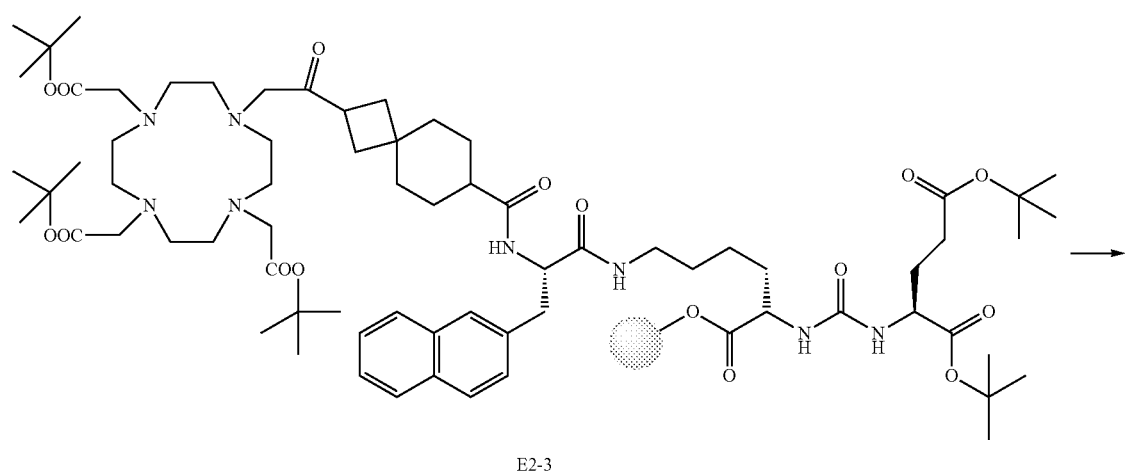
E2-3
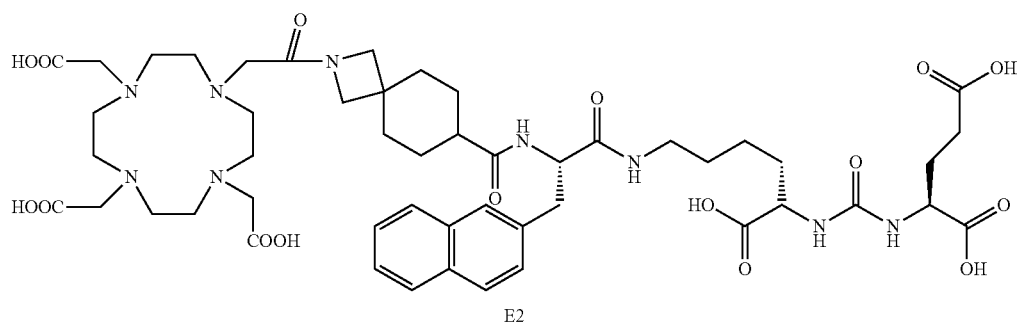
E2

General Synthetic Method D:

1) Synthesis of Intermediate E2-1:

The resin-loaded compound M1 and compound M3 (1.5 times the equivalent) were respectively added into a reaction flask. DMF was used as a solvent, and then 1.5 equivalents of HOBt and 1.5 equivalents of DIC were added for resin condensation coupling. The mixture was stirred at room temperature for 2.5 hours. The detection method was ninhydrin detection showing dark blue. After the completion of the reaction by monitoring, the reaction solution was filtered and washed 3-5 times with DMF to give compound E2-1;

2) Synthesis of Intermediate E2-2:

The intermediate E2-1 was added to a reaction flask, and the Fmoc protecting group was removed with 25% piperidine/DMF (volume ratio). The mixture was then filtered and washed 3-5 times with DMF. The washed and dried compound was added to a reaction bottle containing DMF. 2 times the equivalent of DOTA-Tris (t-Bu) ester, 2 times the equivalent of HOBt and 2 times the equivalent of DIC were added respectively, and stirred at room temperature for 2.0 hours. The detection method was ninhydrin detection showing dark blue. After the completion of the reaction, the reaction solution was filtered and washed 3-5 times with DMF to give intermediate compound E2-3;

3) Synthesis of Compound E2:

A cleavage reagent (trifluoroacetic acid:$H_2O$:triisopropylsilane=90:5:5, v/v) was added into a reaction vial containing intermediate E2-3 to cleave the target polypeptide from the resin and remove the side chain protecting group (cleaving at 30° C. for 3 hours). The filtrate was added to a large amount of cold anhydrous diethyl ether to precipitate the polypeptide and the mixture was centrifuged. The polypeptide was washed several times with diethyl ether and then dried to give the crude polypeptide. The crude product was purified by reverse-phase high-performance liquid chromatography to give compound E2. Column model: Agela C18 (10 m, 100 Å, 50×250 mm). Chromatographic operating conditions: mobile phase A was an aqueous solution containing 0.05% trifluoroacetic acid and 2% acetonitrile; mobile phase B was 90% acetonitrile in water; from 0% B to 100% B within 25 minutes. The flow rate was 25 ml per minute and the UV detection wavelength was 220 nm. After freeze-drying the solvent, the pure peptide in a fluffy state was obtained. The chemical structure was characterized by MALDI-TOF mass spectrometry, and the purity was determined by analytical high-performance liquid chromatography (Agela C18-10×250 mm, flow rate: 1 ml per minute), wherein mobile phase A was an aqueous solution containing 0.05% trifluoroacetic acid and 2% acetonitrile, and mobile phase B was 90% acetonitrile in water (from 0% B to 100% B within 10 minutes). MS: $[M+1]^+$=1054.6, $[M+Na]^+$=1075.8.

Example 3: Synthesis of Compound E3

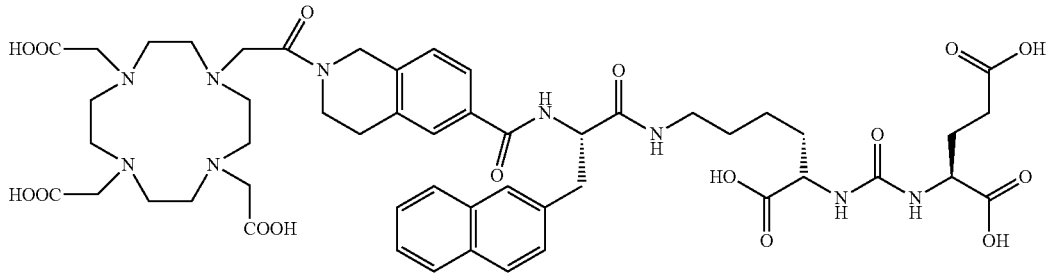

Both of general synthetic method C, D can obtain compound E3; MS: $[M+1]^+$=1062.1, $[M+Na]^+$=1084.7

Example 4: Synthesis of Compound E4

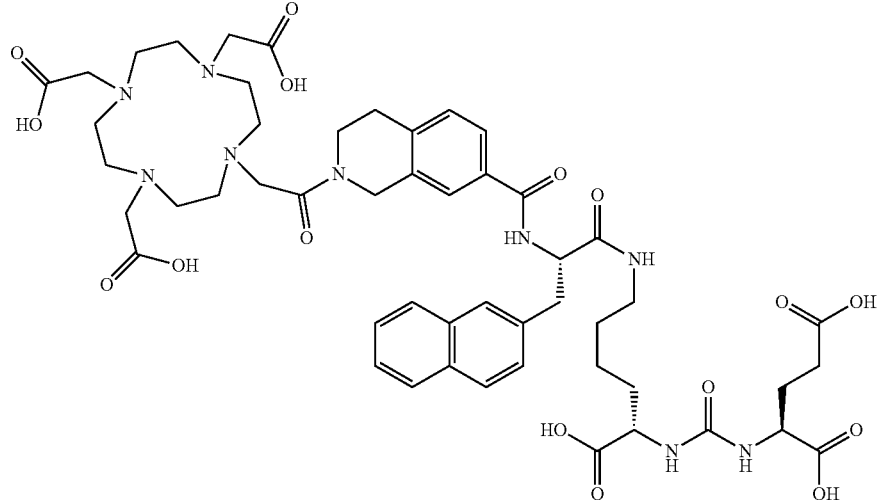 [SMILES: O=C(O)CC[C@H](NC(=O)N[C@@H](CCCCNC(=O)[C@H](Cc1ccc2ccccc2c1)NC(=O)c1ccc2c(c1)CN(C(=O)CN1CCN(CC(=O)O)CCN(CC(=O)O)CCN(CC(=O)O)CC1)CC2)C(=O)O)C(=O)O]

Compound E4 was obtained by using general synthetic method C.
Example 5: Synthesis of Compound E5
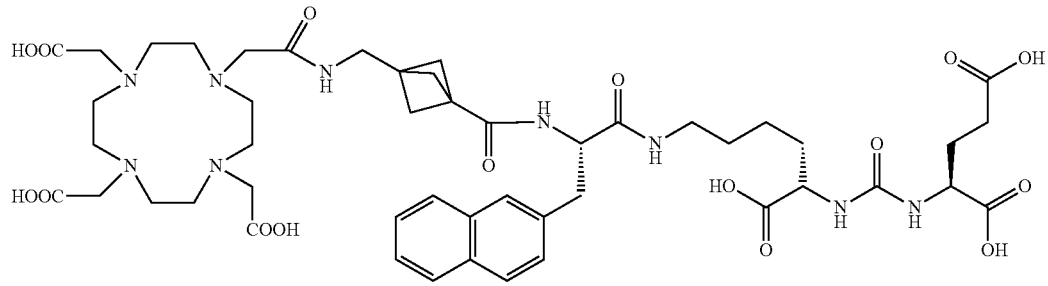
Compound E5 was obtained by using general synthetic method D; MS: [M+1]$^+$=1027.6, [M+Na]$^+$=1049.8
Example 6: Synthesis of Compound E6
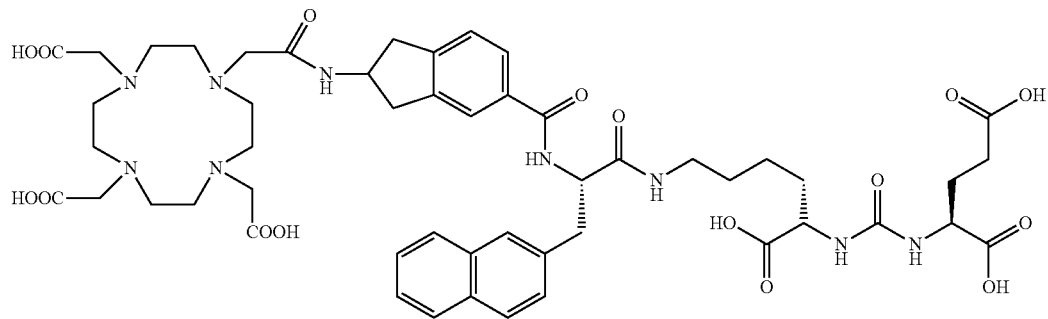
Both of general synthetic method C, D can obtain compound E6; MS: [M+1]$^+$=1063.5, [M+Na]$^+$=1085.4
Example 7: Synthesis of Compound E7
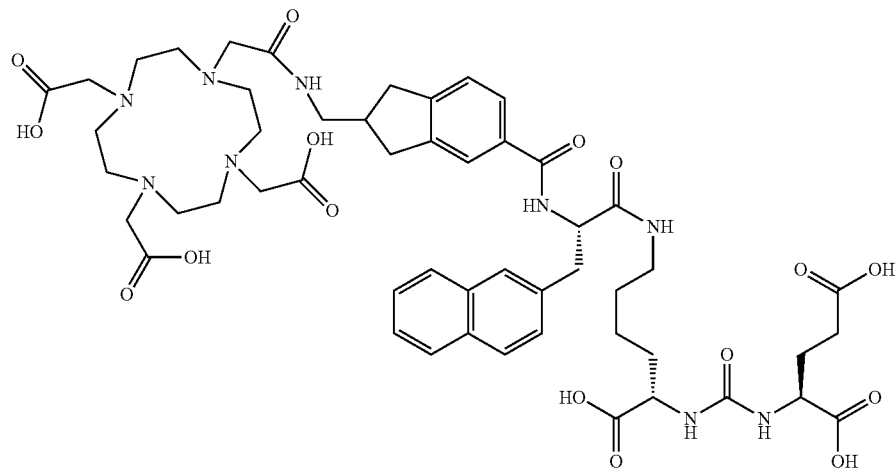 [SMILES: O=C(O)CC[C@H](NC(=O)N[C@@H](CCCCNC(=O)[C@H](Cc1ccc2ccccc2c1)NC(=O)c1ccc2c(c1)CC(CNC(=O)CN1CCN(CC(=O)O)CCN(CC(=O)O)CCN(CC(=O)O)CC1)C2)C(=O)O)C(=O)O]

Compound E7 was obtained by using general synthetic method D; MS: [M+1]$^+$=1077.2
Example 8: Synthesis of Compound E8
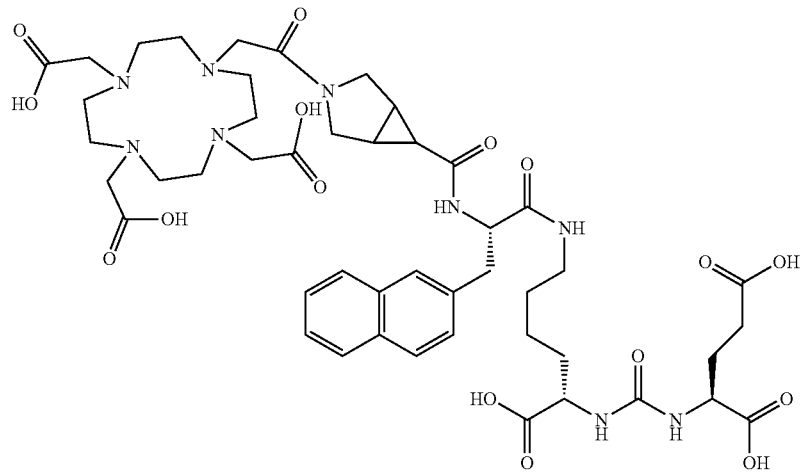 [SMILES: O=C(O)CC[C@H](NC(=O)N[C@@H](CCCCNC(=O)[C@H](Cc1ccc2ccccc2c1)NC(=O)C1C2CN(C(=O)CN3CCN(CC(=O)O)CCN(CC(=O)O)CCN(CC(=O)O)CC3)CC21)C(=O)O)C(=O)O]
Compound E8 was obtained by using general synthetic method D; MS: [M+1]$^+$=1013.07
Example 9: Synthesis of Compound E9
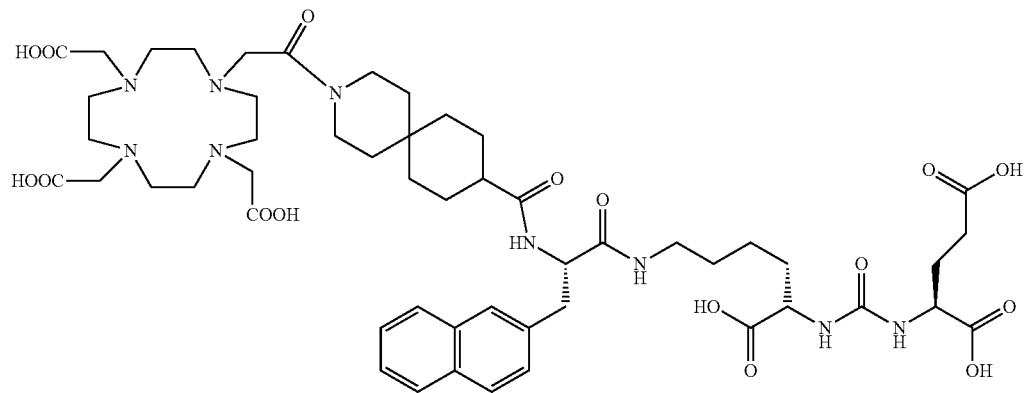
Compound E9 was obtained by using general synthetic method D; MS: [M+1]$^+$=1084.2, [M+Na]$^+$=1105.3
Example 10: Synthesis of Compound E10
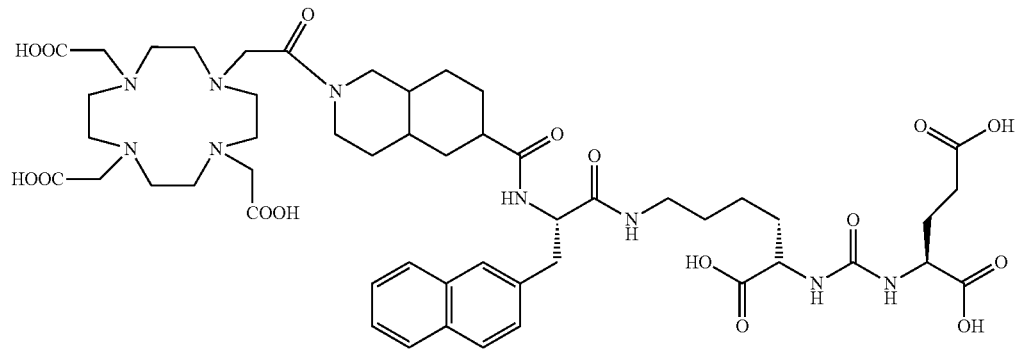

Compound E10 was obtained by using general synthetic method D: MS: [M+1]$^+$=1069.5, [M+Na]$^+$=1090.5
Example 11: Synthesis of Compound E11
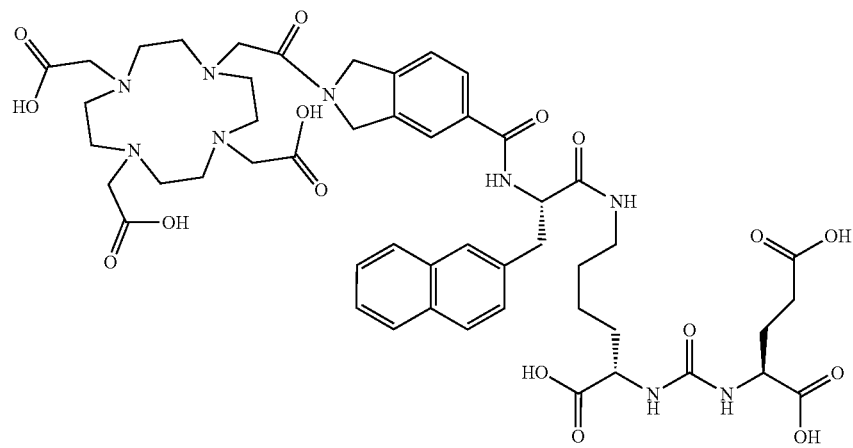 [SMILES: O=C(O)CC[C@H](NC(=O)N[C@@H](CCCCNC(=O)[C@H](Cc1ccc2ccccc2c1)NC(=O)c1ccc2c(c1)CN(C(=O)CN1CCN(CC(=O)O)CCN(CC(=O)O)CCN(CC(=O)O)CC1)C2)C(=O)O)C(=O)O]
Compound E11 was obtained by using general synthetic method C; MS: [M+1]$^+$=1048.4
Example E12: Synthesis of Compound E12
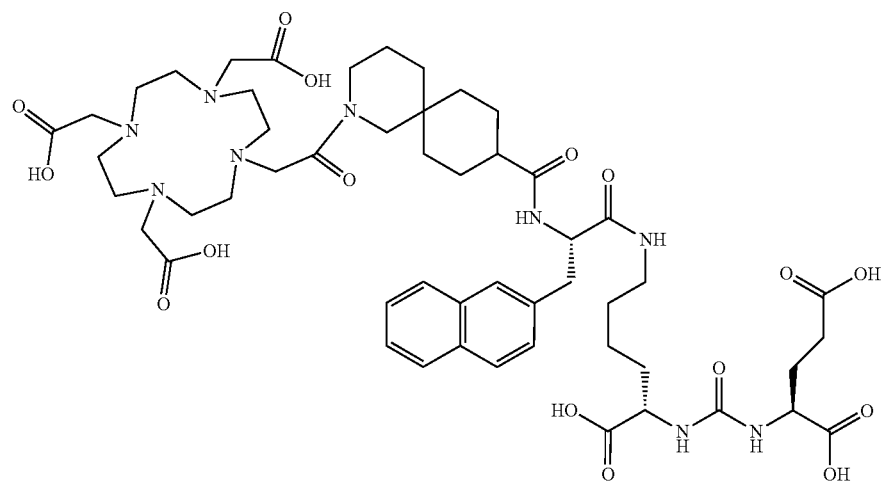 [SMILES: O=C(O)CC[C@H](NC(=O)N[C@@H](CCCCNC(=O)[C@H](Cc1ccc2ccccc2c1)NC(=O)C1CCC2(CCCN(C(=O)CN3CCN(CC(=O)O)CCN(CC(=O)O)CCN(CC(=O)O)CC3)C2)CC1)C(=O)O)C(=O)O]

Compound E12 was obtained by using general synthetic method D; MS: [M+1]$^+$=1082.5
Example 13: Synthesis of Compound E13
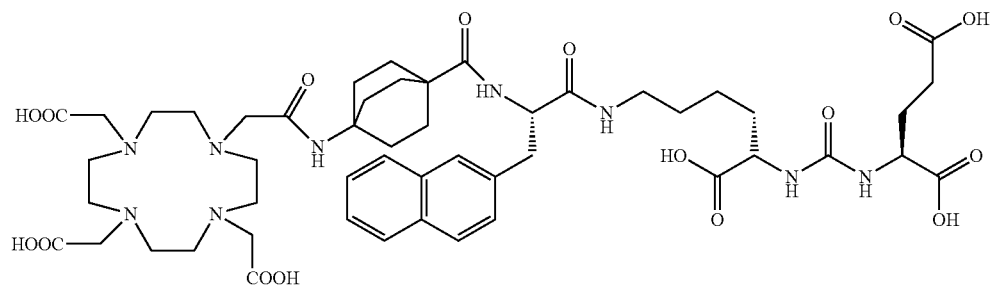
Compound E13 was obtained by using general synthetic method D; MS: [M+1]$^+$=1055.2, [M+Na]$^+$=1076.5
Example 14: Synthesis of Compound E14
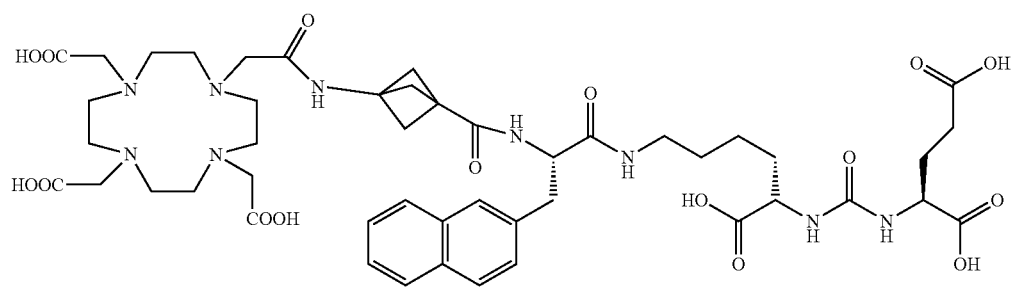
Compound E14 was obtained by using general synthetic method D; MS: [M+1]$^+$=1013.1, [M+Na]$^+$=1034.4
Example 15: Synthesis of Compound E15
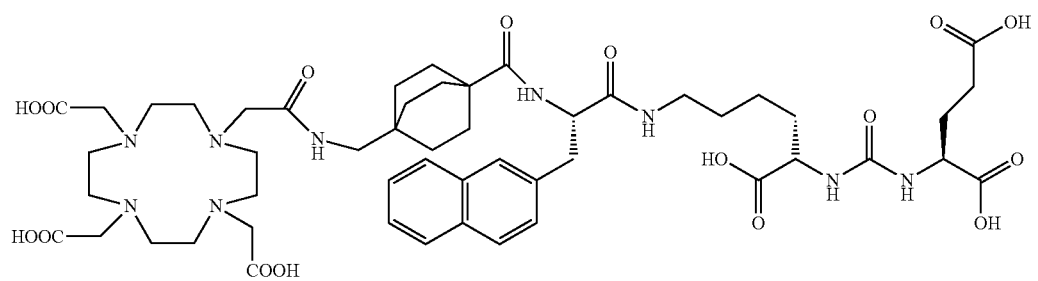

Compound E15 was obtained by using general synthetic method D; MS: [M+1]$^+$=1069.1, [M+Na]$^+$=1090.5
Example 16: Synthesis of Compound E16
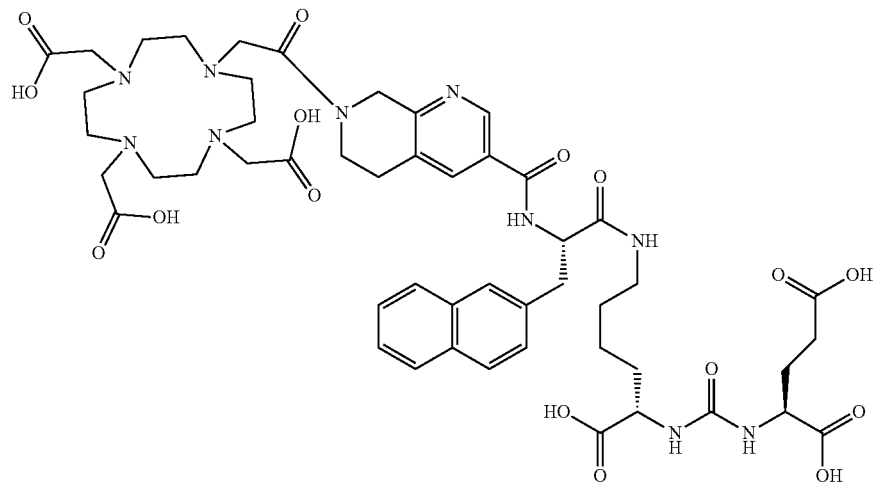 [SMILES: O=C(O)CC[C@H](NC(=O)N[C@@H](CCCCNC(=O)[C@H](Cc1ccc2ccccc2c1)NC(=O)c1cnc2c(c1)CCN(C(=O)CN1CCN(CC(=O)O)CCN(CC(=O)O)CCN(CC(=O)O)CC1)C2)C(=O)O)C(=O)O]
Compound E16 was obtained by using general synthetic method D; MS: [M+1]$^+$=1063.4
Example 17: Synthesis of Compound E17
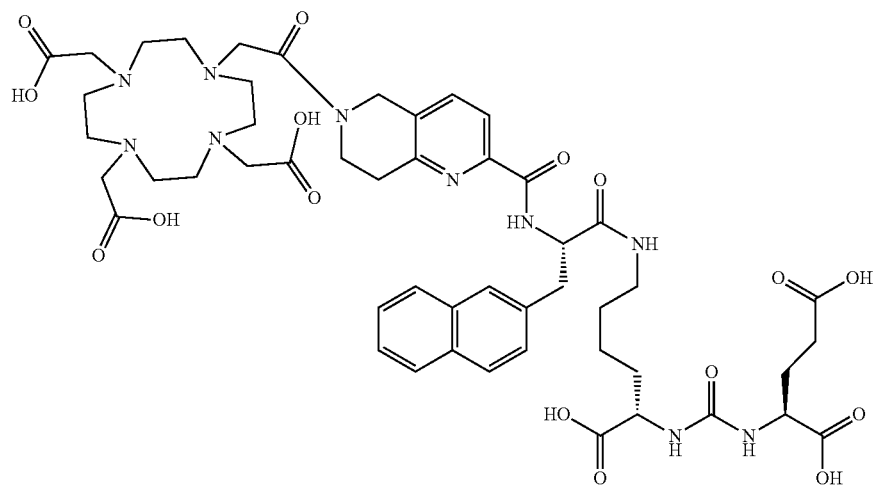 [SMILES: O=C(O)CC[C@H](NC(=O)N[C@@H](CCCCNC(=O)[C@H](Cc1ccc2ccccc2c1)NC(=O)c1ccc2c(n1)CCN(C(=O)CN1CCN(CC(=O)O)CCN(CC(=O)O)CCN(CC(=O)O)CC1)C2)C(=O)O)C(=O)O]

Compound E17 was obtained by using general synthetic method C; MS: $[M+1]^+=1063.5$
Example 18: Synthesis of Compound E18
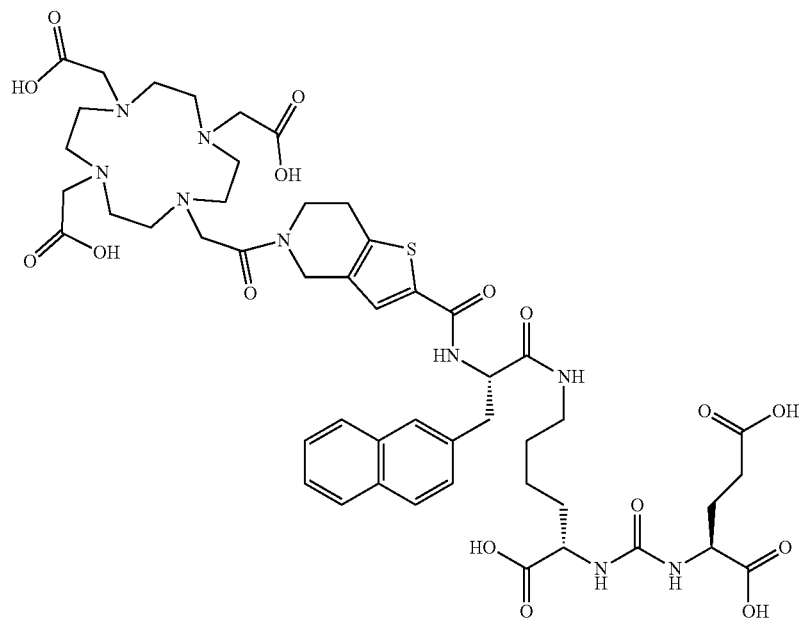 [SMILES: O=C(O)CC[C@H](NC(=O)N[C@@H](CCCCNC(=O)[C@H](Cc1ccc2ccccc2c1)NC(=O)c1cc2c(s1)CCN(C(=O)CN1CCN(CC(=O)O)CCN(CC(=O)O)CCN(CC(=O)O)CC1)C2)C(=O)O)C(=O)O]
Compound E18 was obtained by using general synthetic method C; MS: $[M+1]^+=1068.6$
Example 19: Synthesis of Compound E19
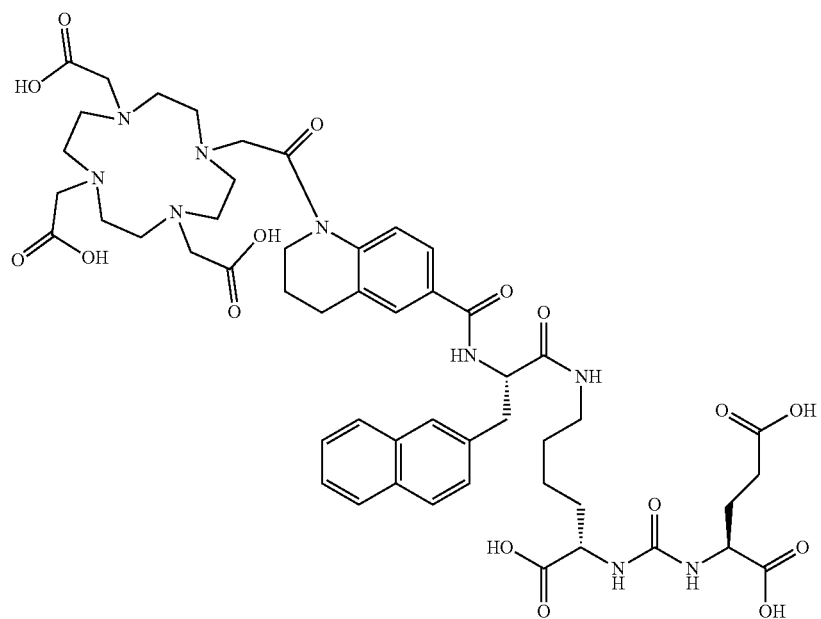 [SMILES: O=C(O)CC[C@H](NC(=O)N[C@@H](CCCCNC(=O)[C@H](Cc1ccc2ccccc2c1)NC(=O)c1ccc2c(c1)CCCN2C(=O)CN1CCN(CC(=O)O)CCN(CC(=O)O)CCN(CC(=O)O)CC1)C(=O)O)C(=O)O]

Compound E19 was obtained by using general synthetic method D; MS: [M+1]$^+$=1063.2
Example 20: Synthesis of Compound E20
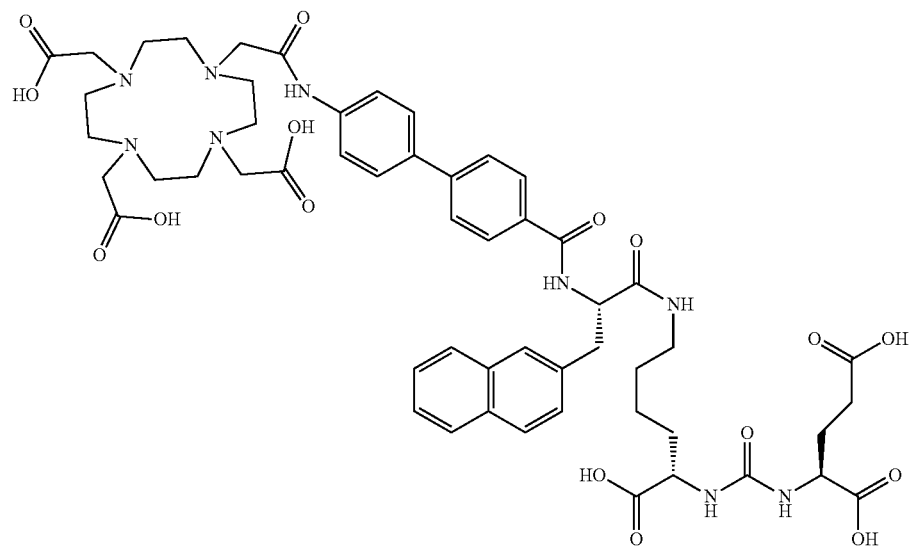 [SMILES: O=C(O)CC[C@H](NC(=O)N[C@@H](CCCCNC(=O)[C@H](Cc1ccc2ccccc2c1)NC(=O)c1ccc(-c2ccc(NC(=O)CN3CCN(CC(=O)O)CCN(CC(=O)O)CCN(CC(=O)O)CC3)cc2)cc1)C(=O)O)C(=O)O]
Compound E20 was obtained by using general synthetic method D; MS: [M+1]$^+$=1099.4
Example 21: Synthesis of Compound E 21
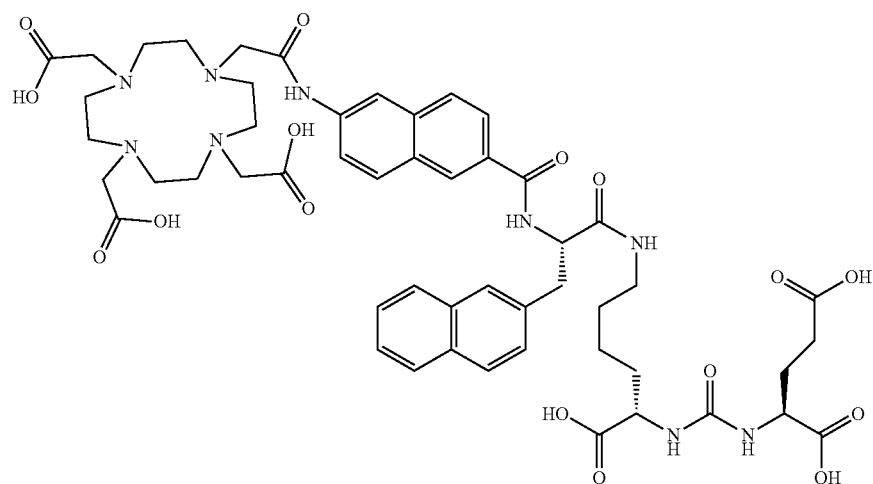 [SMILES: O=C(O)CC[C@H](NC(=O)N[C@@H](CCCCNC(=O)[C@H](Cc1ccc2ccccc2c1)NC(=O)c1ccc2cc(NC(=O)CN3CCN(CC(=O)O)CCN(CC(=O)O)CCN(CC(=O)O)CC3)ccc2c1)C(=O)O)C(=O)O]

Compound E21 was obtained by using general synthetic method D; MS: $[M+1]^+=1073.5$
Example 22: Synthesis of Compound E22
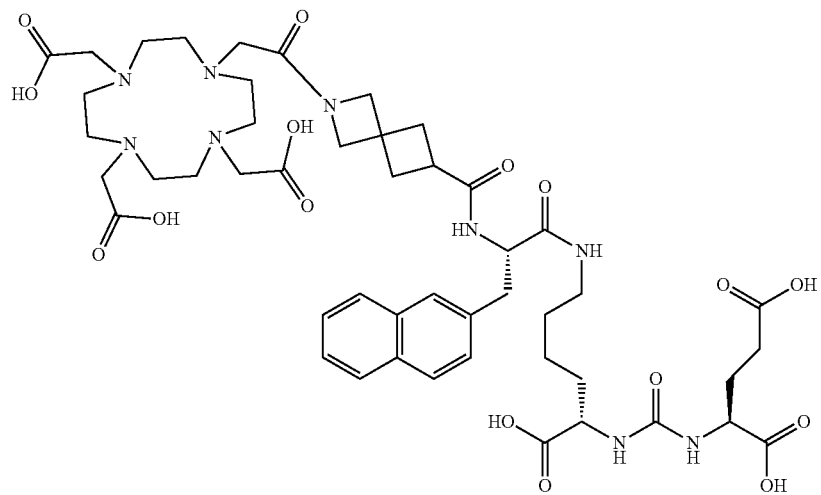 [SMILES: O=C(O)CC[C@H](NC(=O)N[C@@H](CCCCNC(=O)[C@H](Cc1ccc2ccccc2c1)NC(=O)C1CC2(C1)CN(C(=O)CN1CCN(CC(=O)O)CCN(CC(=O)O)CCN(CC(=O)O)CC1)C2)C(=O)O)C(=O)O]
Compound E22 was obtained by using general synthetic method D; MS: $[M+1]^+=1026.5$
Example 23: Synthesis of Compound E23
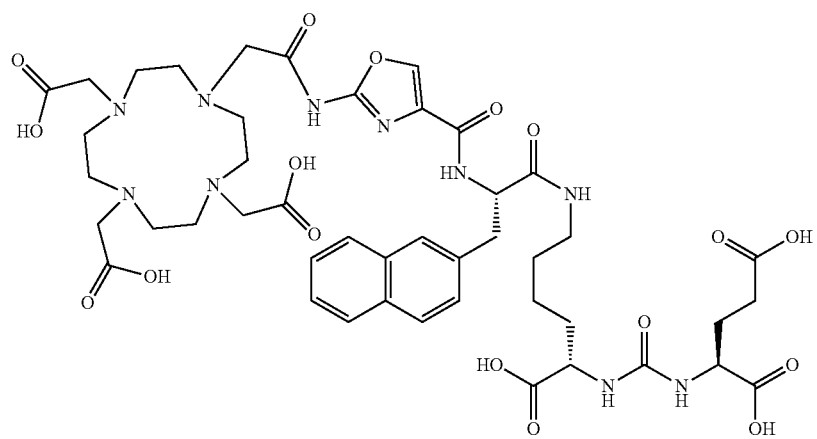 [SMILES: O=C(O)CC[C@H](NC(=O)N[C@@H](CCCCNC(=O)[C@H](Cc1ccc2ccccc2c1)NC(=O)c1coc(NC(=O)CN2CCN(CC(=O)O)CCN(CC(=O)O)CCN(CC(=O)O)CC2)n1)C(=O)O)C(=O)O]

Compound E23 was obtained by using general synthetic method C; MS: [M+1]$^+$=1014.1
Example 24: Synthesis of Compound E24
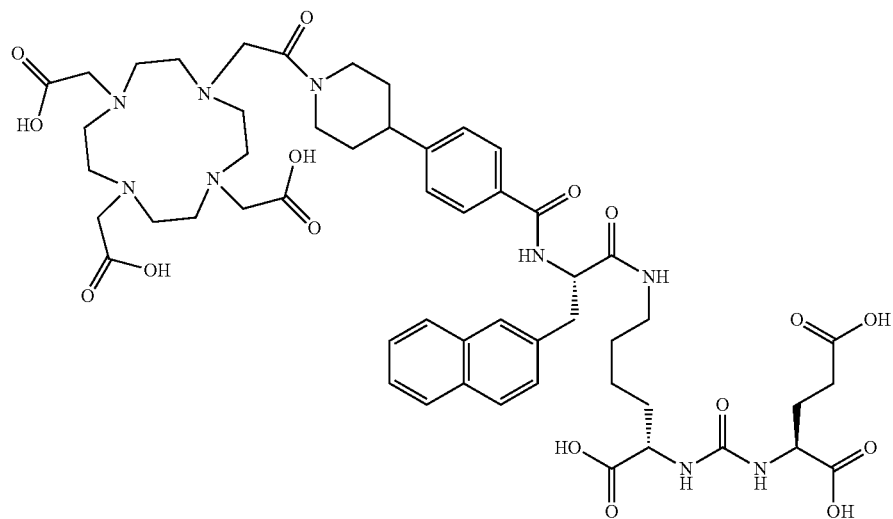 [SMILES: O=C(O)CC[C@H](NC(=O)N[C@@H](CCCCNC(=O)[C@H](Cc1ccc2ccccc2c1)NC(=O)c1ccc(C2CCN(C(=O)CN3CCN(CC(=O)O)CCN(CC(=O)O)CCN(CC(=O)O)CC3)CC2)cc1)C(=O)O)C(=O)O]
Compound E24 was obtained by using general synthetic method C; MS: [M+1]$^+$=1090.5
Example 25: Synthesis of Compound E25
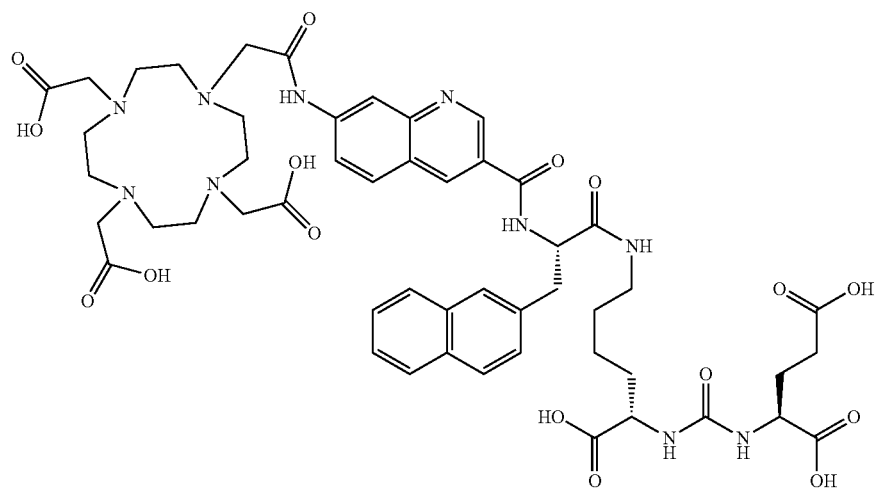 [SMILES: O=C(O)CC[C@H](NC(=O)N[C@@H](CCCCNC(=O)[C@H](Cc1ccc2ccccc2c1)NC(=O)c1cnc2cc(NC(=O)CN3CCN(CC(=O)O)CCN(CC(=O)O)CCN(CC(=O)O)CC3)ccc2c1)C(=O)O)C(=O)O]

Compound E25 was obtained by using general synthetic method D; MS: [M+1]$^+$=1073.5
Example E26: Synthesis of Compound E26
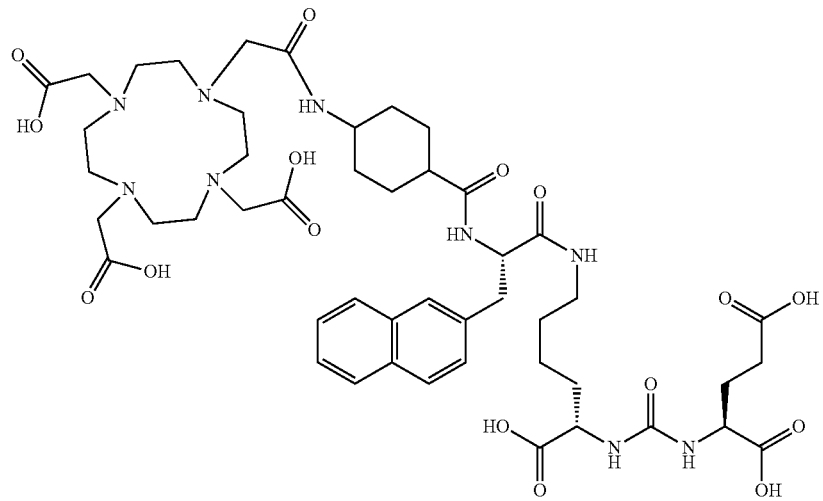 [SMILES: O=C(O)CC[C@H](NC(=O)N[C@@H](CCCCNC(=O)[C@H](Cc1ccc2ccccc2c1)NC(=O)C1CCC(NC(=O)CN2CCN(CC(=O)O)CCN(CC(=O)O)CCN(CC(=O)O)CC2)CC1)C(=O)O)C(=O)O]
Compound E26 was obtained by using general synthetic method D; MS: [M+1]$^+$=1029.1
Example 27: Synthesis of Reference Compound PSMA-617
PSMA-617
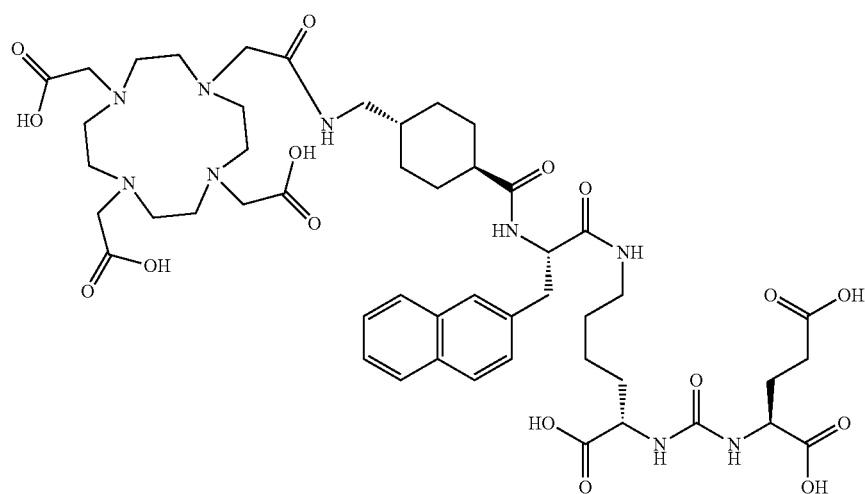

Compound PSMA-617 was obtained by using general synthetic method D; MS: [M+1]⁺=1043.1

The preparation methods and characterizations of all compounds were summarized in Table 1.

TABLE 1

Synthetic methods and characterizations of compounds

| Compound | Synthetic methods | HPLC t$_r$ (min) | MS [M + 1]⁺ |
|---|---|---|---|
| E1 | C | 25.90³ | 1080.1 |
| E2 | D | 12.83² | 1055.1 |
| E3 | C, D | 11.82² | 1062.5 |
| E4 | C | 12.45² | 1062.5 |
| E5 | D | 13.89² | 1013.2 |
| E6 | C, D | 12.16² | 1049.2 |
| E7 | D | 7.34¹ | 1077.2 |
| E8 | D | 6.17¹ | 1013.07 |
| E9 | D | 14.71² | 1083.2 |
| E10 | D | 13.62² | 1069.2 |
| E11 | C | 11.47² | 1048.4 |
| E12 | D | 12.42² | 1082.5 |
| E13 | D | 11.67² | 1055.2 |
| E14 | D | 13.89² | 1013.1 |
| E15 | D | 12.85² | 1069.2 |
| E16 | D | 10.14² | 1064.1 |
| E17 | C | 11.36² | 1064.1 |
| E18 | C | 11.39² | 1068.6 |
| E19 | D | 12.05² | 1063.2 |
| E20 | D | 7.63¹ | 1099.4 |
| E21 | D | 12.27² | 1073.5 |
| E22 | D | 9.66² | 1026.5 |
| E23 | C | 12.11² | 1014.1 |
| E24 | C | 13.65² | 1090.5 |
| E25 | D | 9.96² | 1073.5 |
| E26 | D | 9.78² | 1029.1 |
| PSMA-617 | D | 12.08² | 1043.1 |

¹means using LCMS detection method 1

LCMS detection method 1: the characterization of the compound was carried out by MS, and the purity was determined by an analytical high-performance liquid chromatograph (Agela C18-10×250 mm, flow rate: 1 ml per minute), wherein the mobile phase A was an aqueous solution containing 0.05% trifluoroacetic acid and 2% acetonitrile, mobile phase B was 90% acetonitrile in water, the detection wavelength was 220 nm (from 0% B to 100% B in 10 minutes).

² means using LCMS detection method 2

LCMS detection method 2: the characterization of the compound was carried out by MS, and the purity was determined by an analytical high-performance liquid chromatograph (Agela C18-10×250 mm, flow rate: 1 ml per minute), wherein the mobile phase A was an aqueous solution containing 0.05% trifluoroacetic acid and 2% acetonitrile, mobile phase B was 90% acetonitrile in water, (from 0% B to 100% B in 25 minutes).

³ means using LCMS detection method 3

LCMS detection method 3: the characterization of the compound was carried out by MS, and the purity was determined by an analytical high-performance liquid chromatograph (Agela C18-10×250 mm, flow rate: 1 ml per minute), wherein the mobile phase A was an aqueous solution containing 0.05% trifluoroacetic acid and 2% acetonitrile, the mobile phase B was 90% acetonitrile in water, (from 8% B to 43% B within 35 minutes), and the detector wavelength was 220 nm.

Example 28: Synthesis of Metal Complex ¹⁷⁷Lu-E1

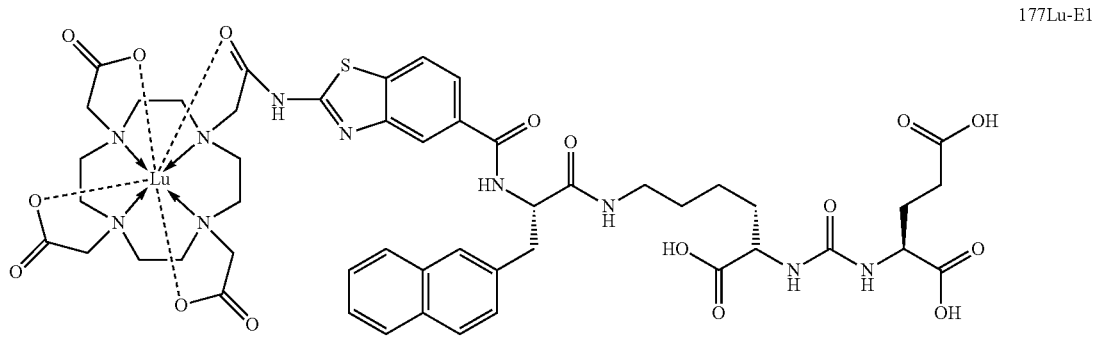

¹⁷⁷Lu-E1

General Synthetic Method E:
1) 4.1 g of sodium acetate was weighed, and 45 mL of ultrapure water was added. After the sodium acetate was completely dissolved, the pH was adjusted to 4.0 with glacial acetic acid. Additional ultrapure water was added until the total volume was 50 mL to obtain a 1M sodium acetate solution. The metal heating block was turned on and pre-heated to 95° C.
2) The precursor compound E1 (1 mg) was weighed respectively, and 1000 μL of sodium acetate solution was added respectively. After fully dissolved, a 1 μg/μL precursor solution was obtained. 10 μL (10 μg) of the precursor solution was weighed, and then diluted by adding 240 μL of sodium acetate solution. Then 250 μCi of $^{177}LuCl_3$ solution was added respectively. The mixture was mixed evenly, and then placed in the heating block and reacted at 95° C. for 30 min. Purification was performed using a $C_{18}$ Sep-Pak.
3) 0.5 g of EDTA sodium salt was weighed, and 50 mL of normal saline was added. The mixture was fully dissolved to obtain a 1% aqueous solution of EDTA sodium salt. 2 μL of $^{177}LuCl_3$ solution was weighed and spotted on a silica gel plate of instant thin-layer chromatography at a distance of 1 cm from the bottom, and blown dry. 2 μL of the reacted solution was weighed and spotted on a silica gel plate of instant thin-layer chromatography at a distance of 1 cm from the bottom, and blown dry. 0.5 mL of 1% EDTA sodium salt solution was used as the developing agent. The bottom of the silica gel plate was placed in the developing agent of the glass test tube, and the bottom of the silica gel plate extended into the liquid level of the developing agent no more than 5 mm. The rubber stopper was covered. When the developing agent was developed to 9-10 cm high on the plate, the silica gel plate was taken out and blown dry. The gamma scanner was used to scan the silica gel plate to compare the $^{177}LuCl_3$ solution and the reaction mixture solution. Radiochemical purity and labeling yield were calculated from peak areas.

As shown in Table 2, the $^{177}LuCl_3$ solution was developed to the top of the silica gel plate in the developing agent.

TABLE 2

| | Region: $^{177}$Lu Detector: PMT | | | | | |
|---|---|---|---|---|---|---|
| Name | Start (mm) | Finish (mm) | Rate of flow (RF) | Area (Counts) | % ROI (%) | % Total proportion (%) |
| Region 1 | 79.6 | 97.8 | 0.988 | 2284 | 100.00 | 95.17 |
| 1 peak | | | | 2284 | 100.00 | 95.17 |

Total area: 2400 Counts
Average background: 0 Counts

As shown in Table 3, the labeled compound $^{177}$Lu-E1 can only be developed to the bottom of the silica gel plate in the developing agent. The radiochemical purity was 96.0%, and the labeling rate was also 100%.

TABLE 3

| | Region: $^{177}$Lu Detector: PMT | | | | | |
|---|---|---|---|---|---|---|
| Name | Start (mm) | Finish (mm) | Rate of flow (RF) | Area (Counts) | % ROI (%) | % total proportion (%) |
| Region 1 | 10.6 | 30.8 | 0.163 | 2386 | 100.00 | 96.91 |
| 1 peak | | | | 2386 | 100.00 | 96.91 |

Total area: 2462 Counts
Average background: 0 Counts

Example 29: Synthesis of Metal Complex $^{177}$Lu-E2

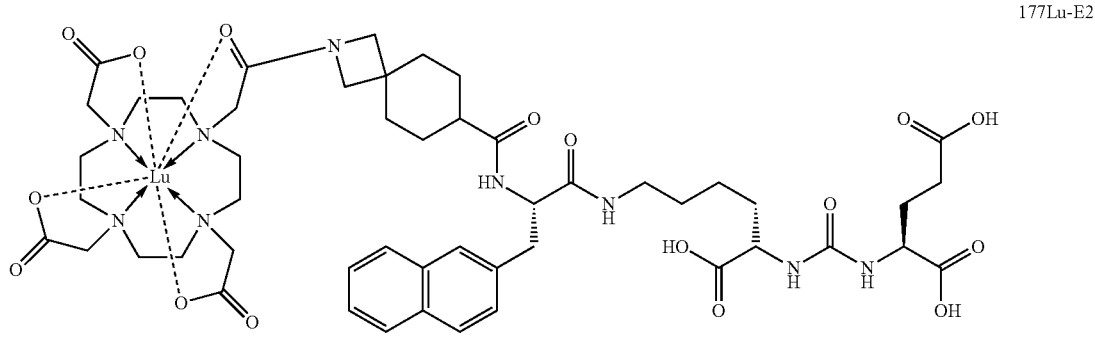

177Lu-E2

Using general synthetic method E, $^{177}$Lu-E2 with a radiochemical purity of 97.4% was obtained as shown in Table 4, and the labeling rate was 100%.

TABLE 4

| | Region: $^{177}$Lu Detector: PMT | | | | | |
|---|---|---|---|---|---|---|
| Name | Start (mm) | Finish (mm) | Rate of flow (RF) | Area (Counts) | % ROI (%) | % Total proportion (%) |
| Region 1 | 5.2 | 21.8 | 0.040 | 3367 | 100.00 | 97.42 |
| 1 peak | | | | 3367 | 100.00 | 97.42 |

Total Area: 3456 Counts
Average background: 0 Counts

Example 30: Synthesis of Metal Complex $^{177}$Lu-E3

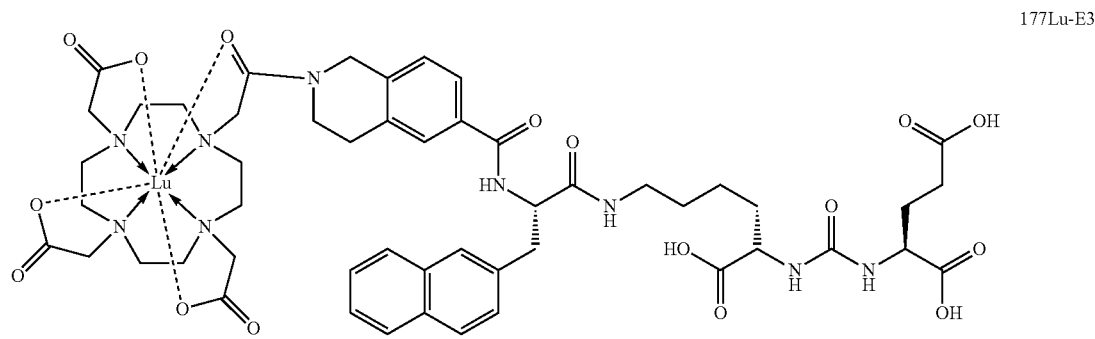

177Lu-E3

Using general synthetic method E, $^{177}$Lu-E3 with a radiochemical purity of 98.2% was obtained as shown in Table 5, and the labeling yield was 100%.

TABLE 5

| | Region: $^{177}$Lu Detector: PMT | | | | | |
|---|---|---|---|---|---|---|
| Name | Start (mm) | Finish (mm) | Rate of flow (RF) | area (Counts) | % ROI (%) | % Total proportion (%) |
| Region 1 | 4.8 | 20.8 | 0.033 | 4420 | 100.00 | 98.20 |
| 1 peak | | | | 4420 | 100.00 | 98.20 |

Total Area: 4501 Counts
Average background: 0 Counts

Example 31: Synthesis of Metal Complex $^{177}$Lu-E9

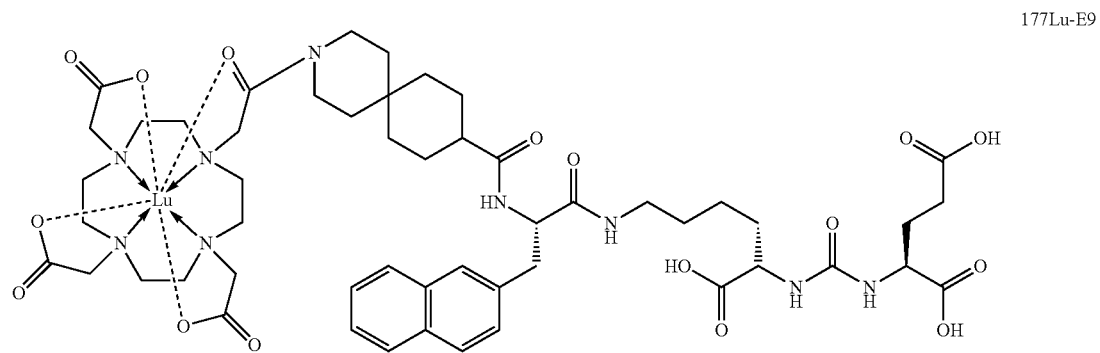

177Lu-E9

Using general synthetic method E, $^{177}$Lu-E9 with a radiochemical purity of 98.4% was obtained as shown in Table 6, and the labeling yield was 100%.

TABLE 6

| | | | Region: $^{177}$Lu Detector: PMT | | | |
|---|---|---|---|---|---|---|
| Name | Start (mm) | Finish (mm) | Rate of flow (RF) | Area (Counts) | % ROI (%) | % Total proportion (%) |
| Region 1 | 7.2 | 23.6 | 0.078 | 5019 | 100.00 | 98.35 |
| 1 peak | | | | 5019 | 100.00 | 98.35 |

Total area: 5103 Counts
Average background: 0 Counts

Example 32: Synthesis of Metal Complex $^{177}$Lu-E14

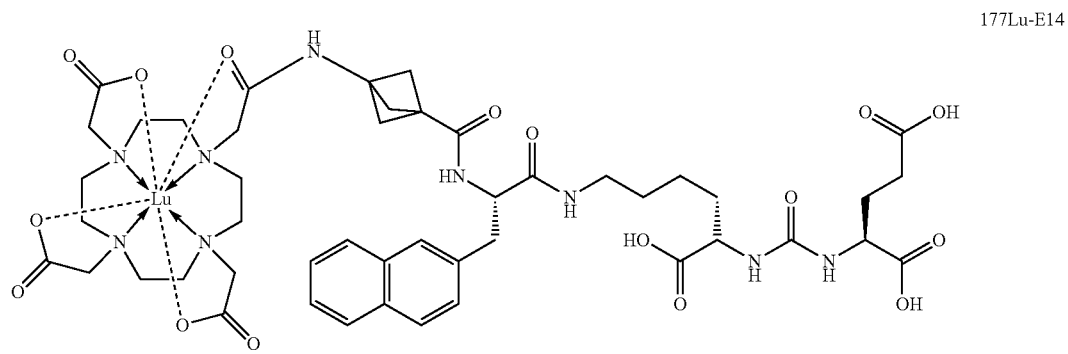

177Lu-E14

Using general synthetic method E, $^{177}$Lu-E14 with a radiochemical purity of 98.5% was obtained as shown in Table 7, and the labeling yield was 100%.

TABLE 7

| | | | Region: $^{177}$Lu Detector: PMT | | | |
|---|---|---|---|---|---|---|
| Name | Start (mm) | Finish (mm) | Rate of flow (RF) | Area (Counts) | % ROI (%) | % Total proportion (%) |
| Region 1 | 6.8 | 25.2 | 0.080 | 5697 | 100.00 | 98.53 |
| 1 peak | | | | 5697 | 100.00 | 98.53 |

Total area: 5782 Counts
Average background: 0 Counts

Example 33: Synthesis of Metal Complex $^{177}$Lu-E5

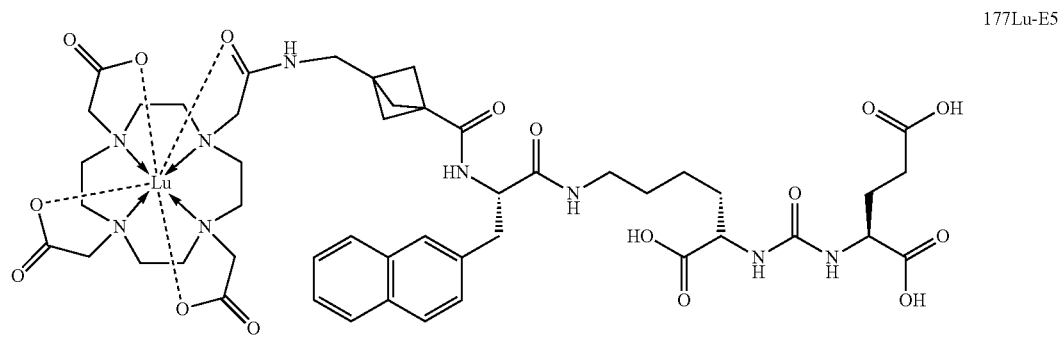

177Lu-E5

Using general synthetic method E, $^{177}$Lu-E5 with a radiochemical purity of 96.8% was obtained as shown in Table 8, and the labeling yield was 100%.

TABLE 8

| | | | Region: $^{177}$Lu Detector: PMT | | | |
|---|---|---|---|---|---|---|
| Name | Start (mm) | Finish (mm) | Rate of flow (RF) | Area (Counts) | % ROI (%) | % Total proportion (%) |
| Region 1 | 0.2 | 30.4 | −0.013 | 22956 | 100.00 | 96.76 |
| 1 peak | | | | 22956 | 100.00 | 96.76 |

Total area: 23725 Counts
Average background: 0 Counts

Example 34: Synthesis of Metal Complex $^{177}$Lu-PSMA-617

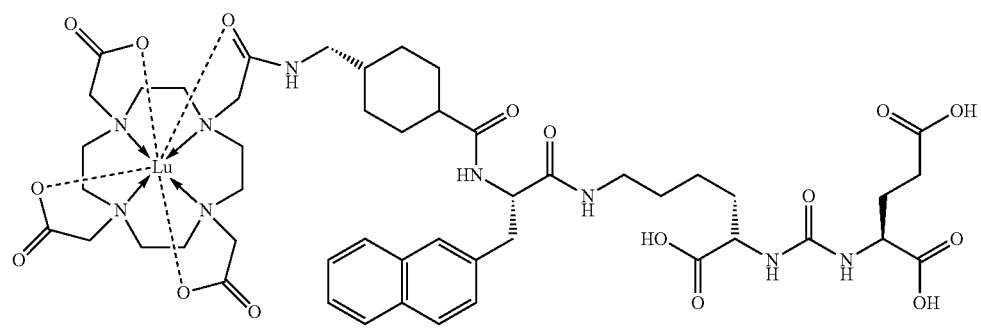

177Lu-PSMA 617

Using general synthetic method E, $^{177}$Lu-PSMA-617 with a radiochemical purity of 98.9% was obtained as shown in Table 9, and the labeling yield was 100%.

TABLE 9

Region: $^{177}$Lu Detector: PMT

| Name | Start (mm) | Finish (mm) | Rate of flow (RF) | Area (Counts) | % ROI (%) | % Total proportion (%) |
|---|---|---|---|---|---|---|
| Region 1 | 0.0 | 30.8 | 0.003 | 12598 | 99.14 | 98.00 |
| Region 2 | 82.0 | 94.0 | 0.970 | 110 | 0.86 | 0.85 |
| 2 peaks | | | | 12708 | 100.00 | 98.85 |

Total area: 12855 Counts
Average background: 0 Counts

Example 35: Labeling Test of Compound $^{68}$Ga

The selected E series compounds were dissolved in DMSO to make a 1 mg/mL solution, and a portion was taken out and diluted with PBS to a 0.1 mg/mL solution for later use. A germanium-gallium generator was rinsed with 5 mL of 0.1 M HCl in stages. The part with the highest activity (0.5 mL) was taken, and 0.5 mL of metal-free sodium acetate buffer (pH=4.5) was added. A 1.5 mL centrifuge tube was used as the reactor, and a certain amount of the precursor (0.1 mg/mL) was added, vortexed to mix for 10 s, heated at 95° C. and 800 rpm for 15 min, and then cooled to room temperature. The reaction solution was passed through a C18 column activated with absolute ethanol and water, and the labeled components were collected for later use. The radiochemical purity of the labeled compound was determined by TLC method.

Effect Example 1: Assay of the Uptake of Labeled Compounds by PSMA-Positive Cells LNCap LNCap cells (Shangcheng Beina Chuanglian Biotechnology Co., Ltd., Industrial Park, Chengguan Town, Shangcheng County, Xinyang City, Henan Province) were revived and passaged for expansion. After the cells were expanded to a sufficient amount, cells were seeded in a 24-well plate at a density of $1 \times 10^4$ cells/well. Uptake tests were performed when cells grew to 80%-90% confluence.

The above labeled compounds $^{177}$Lu-E1, $^{177}$Lu-E2, $^{177}$Lu-E3, $^{177}$Lu-E5, $^{177}$Lu-E9, $^{177}$Lu-E14 and $^{177}$Lu-PSMA-617 were diluted with serum-free medium into 10000, 1000, 100, 10, 1, 0.1 and 0 nM. 1 mL of the diluted solution was added to a 24-well plate, and incubated at 37° C. for 0.5 h. The supernatant was discarded and the cells were washed 3 times with PBS. 250 μL of 1M NaOH solution was added to each well. The cells were pipetted until they were completely dissolved, and transferred to a scintillation vial. 250 μL of NaOH solution was added to each well again to wash the bottom of the well and transferred to a scintillation vial. 2 mL of scintillation fluid was added to each scintillation vial and shaken well. A liquid scintillation counter was used to detect radioactive counts in each vial. The uptake of different concentrations of precursor compounds by LNCap cells is shown in the table below:

| | 0 nM (cpm) | 0.1 nM (cpm) | 1 nM (cpm) | 10 nM (cpm) | 100 nM (cpm) | 1000 nM (cpm) | 10000 nM (cpm) |
|---|---|---|---|---|---|---|---|
| $^{177}$Lu-E1 | 47 | 39 | 169 | 77 | 121 | 331 | 1595 |
| $^{177}$Lu-E2 | 47 | 29 | 91 | 344 | 596 | 775 | 1328 |
| $^{177}$Lu-E3 | 47 | 48 | 95 | 346 | 555 | 903 | 3150 |
| $^{177}$Lu-E5 | 47 | 52 | 70 | 271 | 420 | 520 | 880 |
| $^{177}$Lu-E9 | 47 | 56 | 55 | 84 | 140 | 405 | 1194 |

-continued

|  | 0 nM (cpm) | 0.1 nM (cpm) | 1 nM (cpm) | 10 nM (cpm) | 100 nM (cpm) | 1000 nM (cpm) | 10000 nM (cpm) |
|---|---|---|---|---|---|---|---|
| $^{177}$Lu-E14 | 47 | 28 | 82 | 220 | 345 | 479 | 362 |
| $^{177}$LuPSMA-617 | 47 | 49 | 67 | 225 | 389 | 599 | 1625 |

Effect Example 2: In Vivo Metabolism Test of $^{177}$Lu-Labeled Complex in SD Rats Eighteen SD rats (Hangzhou Ziyuan Experimental Animal Technology Co., Ltd.), male, weighing 180-200 g, were randomly divided into 6 groups, 3 rats in each group. 10 Ci of the labeled precursor compound was injected into the tail vein of each mouse. 250 μL of orbital blood was collected into anticoagulant tubes at 5 min, 0.5 h, 1 h, 2 h, 4 h, 8 h and 24 h after administration. Blood was centrifuged at 3000 rpm for 10 min, and 100 μL of plasma was taken into scintillation vials. 2 mL of scintillation fluid was added to each scintillation vial and shaken well. A liquid scintillation counter was used to detect radioactive counts in each vial.

The metabolism of the labeled compound in SD rats is shown in the table below:

| Compound | Rat ID | 0.083333333 h (cpm) | 0.5 h (cpm) | 1 h (cpm) | 2 h (cpm) | 4 h (cpm) | 8 h (cpm) | 24 h (cpm) |
|---|---|---|---|---|---|---|---|---|
| $^{177}$Lu-E1 | 1 | 28305 | 9829 | 3505 | 615 | 163 | 174 | 151 |
|  | 2 | 17143 | 8252 | 3389 | 1288 | 315 | 179 | 169 |
|  | 3 |  |  |  |  |  |  |  |
|  | MEAN | 22724 | 9041 | 3447 | 952 | 239 | 177 | 160 |
| $^{177}$Lu-E2 | 4 | 37703 | 18427 | 7473 | 1863 | 296 | 178 | 167 |
|  | 5 | 41406 | 15030 | 5428 | 1189 | 219 | 190 | 170 |
|  | 6 |  |  |  |  |  |  |  |
|  | MEAN | 39555 | 16729 | 6451 | 1526 | 258 | 184 | 169 |
| $^{177}$Lu-E3 | 13 | 26791 | 10681 | 3448 | 539 | 178 | 154 | 191 |
|  | 14 | 31372 | 8675 | 3676 | 559 | 135 | 191 | 175 |
|  | 15 | 27797 | 8026 | 2916 | 458 | 181 | 184 | 179 |
|  | MEAN | 28653 | 9127 | 3347 | 519 | 165 | 176 | 182 |
| $^{177}$Lu-E9 | 19 | 30764 | 10391 | 4483 | 892 | 210 | 171 | 164 |
|  | 20 | 38134 | 12249 | 4139 | 652 | 196 | 184 | 162 |
|  | 21 | 30001 | 8575 | 2519 | 346 | 197 | 161 | 183 |
|  | MEAN | 32966 | 10405 | 3714 | 630 | 201 | 172 | 170 |
| $^{177}$Lu-E14 | 7 | 42150 | 18047 | 7200 | 1415 | 203 | 201 | 196 |
|  | 8 | 41058 | 18268 | 6304 | 1686 | 198 | 206 | 175 |
|  | 9 | 45756 | 18614 | 6154 | 1863 | 259 | 203 | 159 |
|  | MEAN | 42988 | 18310 | 6553 | 1655 | 220 | 203 | 177 |
| $^{177}$Lu-PSMA-617 | 10 | 24449 | 9783 | 3865 | 679 | 207 | 188 | 173 |
|  | 11 | 23276 | 13738 | 6988 | 1346 | 219 | 187 | 176 |
|  | 12 | 22010 | 14589 | 7736 | 1544 | 225 | 170 | 178 |
|  | MEAN | 23245 | 12703 | 6196 | 1190 | 217 | 182 | 176 |

Effect Example 3: SPECT Imaging

100 μCi of $^{177}$Lu-labeled $^{177}$Lu-E3 and $^{177}$Lu-PSMA-617 were injected into mice carrying LNCaP PSMA-positive tumors (Jiangsu Huajing Molecular Imaging and Drug Research Institute Co., Ltd.) through the tail vein respectively. Mice were anesthetized with 2% isoflurane/98% oxygen for SPECT image contrast study. The results are shown in Table 10 and Table 11. It can be seen from Table 10 and Table 11 that compared with $^{177}$Lu-PSMA-617, $^{177}$Lu-E3 can be rapidly distributed to various organs after entering the animal body; the metabolism of $^{177}$Lu-E3 is mainly excreted through the kidney; and the accumulation of $^{177}$Lu-E3 in PSMA-positive tumors is significantly higher than that of reference animals injected with $^{177}$Lu-PSMA-617.

TABLE 10

| $^{177}$Lu-E3 | 1 h Averaged (% ID/cc) | 4 h Averaged (% ID/cc) | 8 h Averaged (% ID/cc) | 1 d Averaged (% ID/cc) | 3 d Averaged (% ID/cc) |
|---|---|---|---|---|---|
| Tumor | 23.56 | 28.79 | 31.79 | 34.01 | 32.84 |
| Heart | 6.44 | 2.41 | 1.39 | 3.23 | 2.03 |
| Liver | 3.08 | 2.03 | 2.54 | 1.94 | 1.80 |
| Kidney | 165.36 | 129.55 | 87.74 | 8.03 | 3.74 |
| Lung | 5.52 | 3.26 | 1.82 | 2.71 | 2.68 |

TABLE 11

| $^{177}$Lu-PSMA-617 | 1 h Averaged (% ID/cc) | 4 h Averaged (% ID/cc) | 8 h Averaged (% ID/cc) | 1 d Averaged (% ID/cc) | 3 d Averaged (% ID/cc) |
|---|---|---|---|---|---|
| Tumor | 19.42 | 10.68 | 9.4 | 2.19 | 4.76 |
| Heart | 1.59 | 1.47 | 0.53 | 1.45 | 0.46 |
| Liver | 1.61 | 1.27 | 1.04 | 1.43 | 0.96 |
| Kidney | 58.17 | 8.37 | 4.35 | 1.16 | 1.55 |
| Lung | 3.30 | 1.54 | 0.86 | 0.85 | 3.74 |

Effect Example 4: In Vitro Binding Test of Compound and PSMA Protein

A Biacore 8K (Cytiva) instrument was used to determine the binding affinity of disclosed compounds to the PSMA protein (Sinobiological). The PSMA protein was captured on SA chips. Before immobilizing the disclosed compounds (flow path 1 and 2, flow rate 10 μL/min), the PSMA protein was immobilized on flow path 2 by using flow buffer (10 μg/ml, flow rate 5 μL/min, injection time 600 s), and 1M NaCl was injected three times consecutively into 50 mM NaOH to condition the sensor surface. After each disclosed compounds injection, isopropanol in 1M NaCl and 50 mM NaOH was used for additional washing (flow path 1, 2, flow rate 10 μL/min, injection time 60 s).

All compounds were dissolved in 100% DMSO and diluted to 10 mM, and then diluted in test buffer (PBS, pH 7.4, 1 mM TCEP (tris-(2-hydroxyethyl)phosphine), 0.05% P20, 2% dimethyl sulfoxide) at an appropriate highest concentration. Analytes were run using the following conditions: 15° C. analysis temperature, analysis steps=all set to LMW kinetics; cycle type=single cycle (90 s contact time, 1800 s separation time, 30 ul/min flow rate, channels 1, 2); channel detection=2-1). Data were evaluated using Biacore Insight evaluation software, and data were fit to a 1:1 binding model.

Biacore results are shown in Table 12: $pK_D$=−Log $K_D$, where $K_D$ is the binding affinity of the compounds to PSMA protein measured by Biacore. $K_D$ is expressed by $K_D$ (M)=$K_d$ (1/s)/$K_a$ (1/Ms).

TABLE 12

Binding affinity of the disclosed compounds to PSMA protein

| Compound | $pk_D$ |
|---|---|
| E1 | — |
| E2 | 9.64 |
| E3 | 9.26 |
| E4 | 9.57 |
| E5 | — |
| E6 | — |
| E7 | — |
| E8 | 9.49 |
| E9 | 9.55 |
| E10 | — |
| E11 | — |
| E12 | — |
| E13 | 12.46 |
| E14 | — |
| E15 | — |
| E16 | — |
| E17 | — |
| E18 | 12.28 |
| E19 | — |
| E20 | 12.46 |
| E21 | 9.82 |
| E22 | 10.00 |
| E23 | — |
| E24 | 15.53 |
| E25 | 10.15 |
| E26 | 9.44 |
| PSMA-617 | 11.69 |

The results of the above tests show that the PSMA inhibitors obtained with fused aromatic rings, bridged carbocyclic rings, and secondary amine compounds as linkers not only have a good biological activity against PSMA proteins, but also several compounds show better in vitro biological activity comparing to the reference PSMA-617.

Effect Example 5: Determination of the Ability of Cell Binding and Cell Endocytosis LNCAP cells in the logarithmic growth phase (Obio Technology (Shanghai) Corp., Ltd.) were made into a cell suspension. The cell suspension was adjusted to a cell density of $2\times10^5$/ml and inoculated 1 mL into a 24-well cell culture plate. Cells were incubated in an incubator at 37° C. for 48 hours. Three hours before the test, the medium was replaced with serum-free RPMI1640 medium (NEWZERUM), the cell culture medium was aspirated, and the cells were washed once with PBS. Serum-free RPMI1640 medium was used to prepare $^{177}$Lu-E series compounds at concentrations of 32, 16, 8, 4, 1, 0.5, 0.1, 0.02, 0.01, 0.002 uCi/mL. The original medium was discarded, and then 1 mL of the prepared solution containing $^{177}$Lu-E series compounds was added to each well. The plate was placed on ice for 2 hours, and then the cells were washed three times with 0.5 mL of ice-cold PBS. The washing solution was aspirated, and the cells were lysed with 0.5 mL of 1M NaOH and washed twice with 0.5 mL of PBS, and the sodium hydroxide (0.5 mL) and PBS (0.5 mL×2) solutions were collected. The uptake counts were determined.

The results of the cell binding tests are shown in FIG. 1. It can be seen from FIG. 1 that the cell binding test shows that the tested compounds have a good ability to bind to PSMA cells, especially compound E26 has an excellent cell binding ability.

Endocytosis tests: LNCAP cells in logarithmic growth phase (Mall Beina Chuanglian Biotechnology Co., Ltd.) were made into a cell suspension. The cell suspension was adjusted to a cell density of $1\times10^5$/ml and seeded 1 mL into a 12-well cell culture plate. Cells were incubated in an incubator at 37° C. for 48 hours. The medium was replaced with serum-free RPMI1640 medium 3 hours before the test. The cell culture medium was aspirated, and the cells were washed once with PBS.

Both the E series compounds and the reference compound PSMA-617 were labeled with $^{177}$Lu and formulated with physiological saline (containing 0.05% of BSA) to a solution of 47.36 MBq (~1280 uci)/mL. The above solution was diluted with serum-free medium, and added into the plate, so that the concentration of the labeled compound in each well was (5 uci/well); The cells were incubated in an incubator at 37° C. for 2 hours, and then washed three times with ice-cold PBS. The washing solution was aspirated, and 0.5M glycine buffer (100 mM NaCl, pH2.8, adjusted with hydrochloric acid) was added. The cells were incubated for 10 minutes and washed three times with 0.5M glycine buffer. The washing solution was aspirated, and collected. The cells were lysed with 0.5 mL of 1M sodium hydroxide, and washed twice with 0.5 mL of PBS. The sodium hydroxide (0.5 mL) and PBS (0.5 mL×2) solutions were collected, and the uptake counts were determined.

Figure 2:
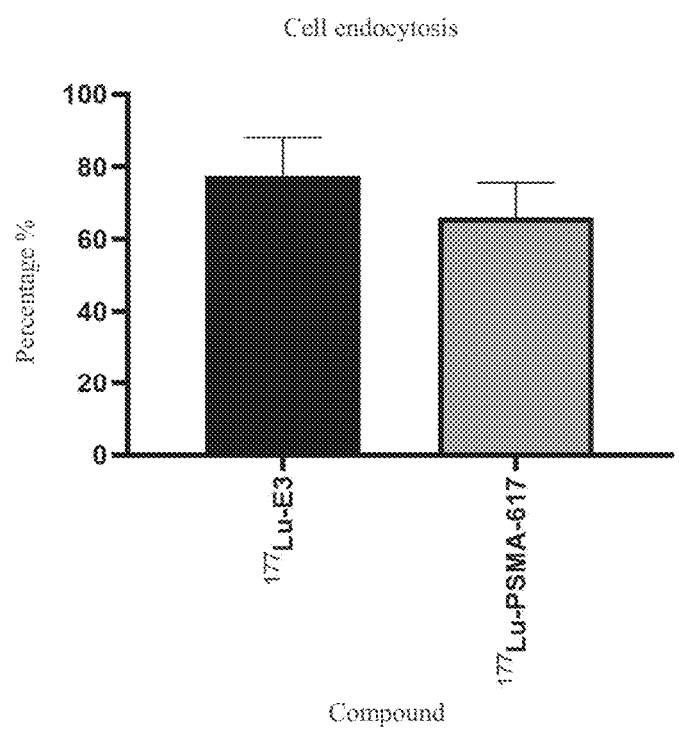
FIG. 2 shows the cell endocytosis test of effect example 5.

FIG. 2 shows the results of the endocytosis test. Combined with the results of the above examples, the E series compounds not only have higher cell affinity, but also show the property of being more easily endocytosed by cells than the reference compound PSMA-617 in the endocytosis test at 37° C. Endocytosis is of great significance for the absorption and retention of radiolabeled compounds in tumor cells, because it directly affects the application of compounds containing radioactive substances in tumor treatment.

Effect Example 6: Specificity Test of E Series Compounds

Figure 3:
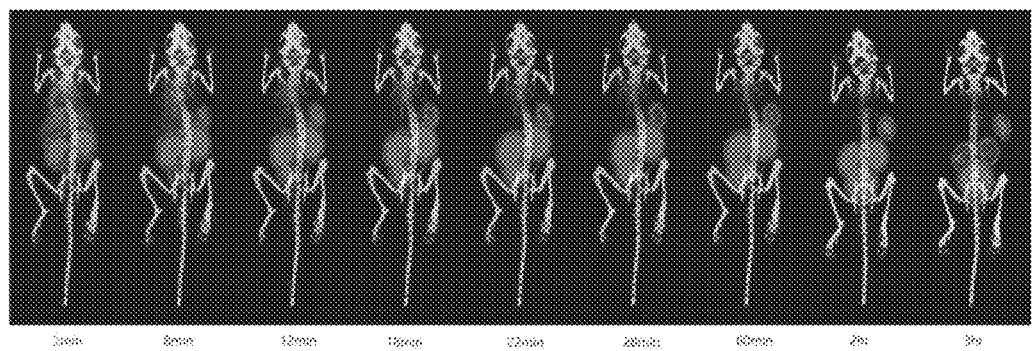
FIG. 3 shows the PET/CT scanning after administration of effect example 6.

The $^{68}$Ga-E3 radiolabeled compound was injected into the tail vein of PSMA-positive (22RV1) tumor-bearing mice (Jiangsu Huajing Molecular Imaging and Drug Research Institute Co., Ltd.) (about 7.4 MBq/mouse, specific activity: 22423.82 KBq/μg) (50 uCi). After administration, PET/CT was used for 1 h dynamic scanning, medium resolution whole body CT, and 10 min static scanning at 2 h and 3 h. It can be clearly seen from FIG. 3 that the drug is rapidly distributed into the animal body after administration, and the drug is rapidly metabolized by the kidneys and excreted from the body over time. The enrichment of the drug on PSMA expressing tumors reaches the highest level at about 30 minutes after administration, and then it is gradually washed out of the body, but there is still a relatively high $^{68}$Ga-E3 enrichment on the tumor at 180 minutes.

Figure 4:
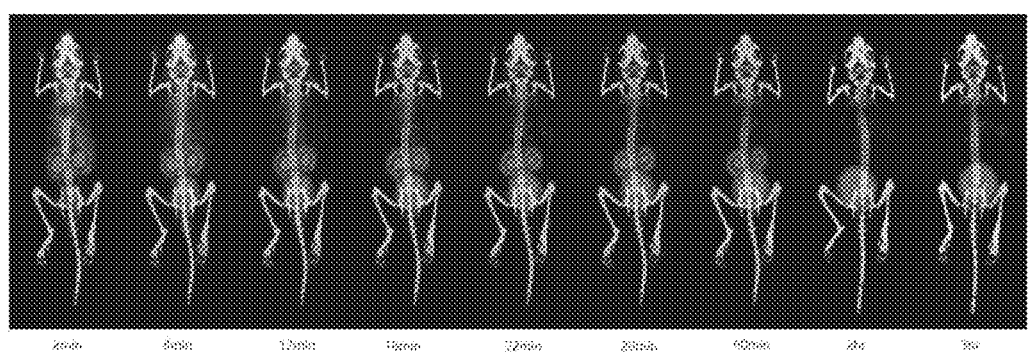
FIG. 4 shows the specificity test of the E series compounds of effect example 6.

The next day, the mixture of $^{68}$Ga-E3 and PSMA standard PMPA (2 mg/Kg) was injected into the tail vein of PSMA-positive tumor-bearing mice (about 7.4 MBq/mouse, specific activity: 22423.82 KBq/μg) (50 uCi). After administration, PET/CT was used for 1 h dynamic scanning, medium resolution whole body CT, and 10 min static scanning at 2 h and 3 h. The results are depicted in detailed in FIG. 4.

PMPA is a specific inhibitor of PSMA. When PMPA is administered together with $^{68}$Ga-E3, $^{68}$Ga-E3 and PMPA are rapidly distributed to various organs in the animal body. However, PMPA occupies the PSMA target on the tumor, thus preventing the binding of $^{68}$Ga-E3 to PSMA on the tumor. This result reflects that E3 has high specificity against PSMA.

Effect Example 7: Determination of c Log P

Three EP tubes were taken, and 0.5 mL of saturated n-octanol and 480 μL of ultrapure water were added into each EP tube. 20 μL (about 1 MBq) solution of E series compounds and reference compound were then added respectively. The mixture was shaken evenly and then centrifuged at room temperature (2000 r/min, 5 min, centrifugal radius: 10 cm). 100 μL was taken from the lipid layer and aqueous layer of each tube, and the radioactive counts per minute of the two phases were measured. The Log P value was calculated and the results were averaged.

Figure 5:
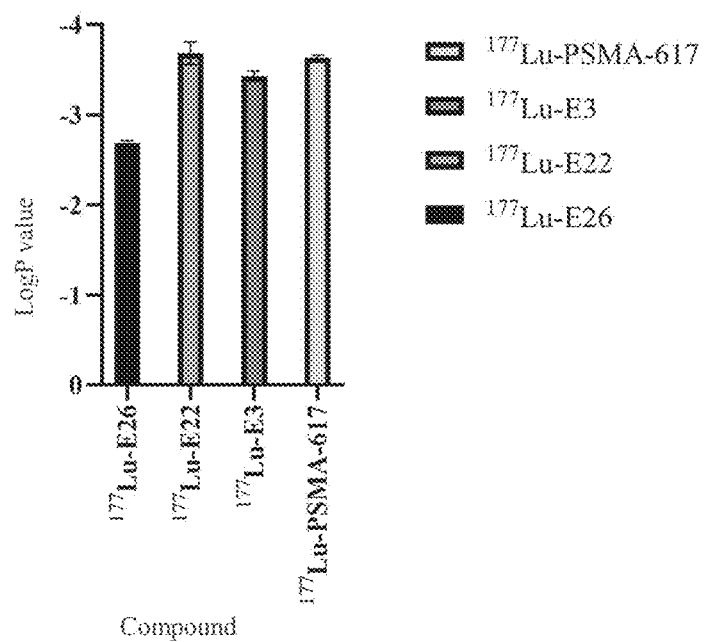
FIG. 5 shows the test result of Log P of effect example 6.

The Log P test results shown in FIG. 5 show that the tested E series compounds all have good hydrophilicity, among which E3 and E22 have similar lipophilicity compared with the reference compound PSMA-617, while E26 has better lipophilicity. In addition, the value of C log P shows that the tested compounds all have good water solubility.

Effect Example 8: Determination of Plasma Protein Binding (PPB) Binding of E Series Compounds Three EP tubes were taken, and 0.2 mL of plasma and 50 μL of $^{177}$Lu-labeled compound were added to each tube. The mixture was incubated in a thermostat at 37° C. for 10 min, and then taken out and added to ultrafiltration tubes, respectively. The ultrafiltration tubes were centrifuged at 13,000 rpm for 45 min. 50 μL of normal saline was then added, and the mixture was centrifuged for another 15 minutes. The radioactive counts per minute of each tube casing and filtrate were then measured. PPB was calculated, and the mean of 3 tubes was recorded. PPB=[(supernatant counts−background counts)]/(subnatant counts+supernatant counts−2*background counts)]*100.

Figure 6:
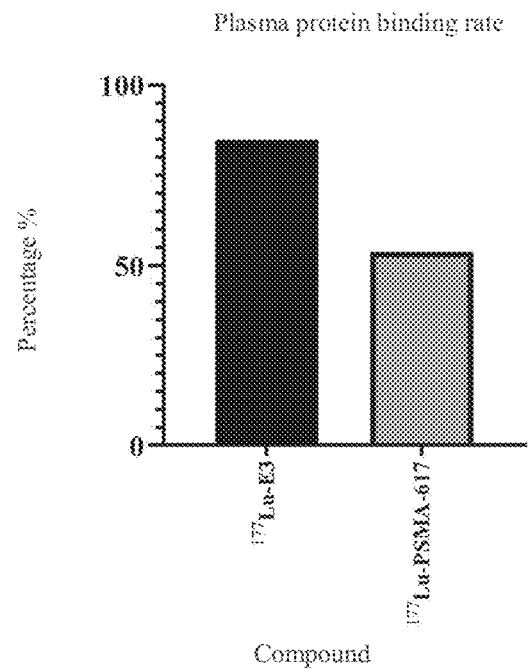
FIG. 6 shows the test result of binding to PPB of effect example 8.

The degree of binding rate of compound to plasma protein (PPB) plays an important role in the circulation of the compound in the blood. Although E3 has similar lipophilicity to the reference compound PSMA-617 either from the structure of the compound or from the Log P results of the compound (FIG. 6), E3 exhibits an extremely high PPB binding rate, which is of great significance for the retention of the compound in the blood.

Effect Example 9: Bio-Distribution of E Series Compounds

In vivo distribution in healthy rats: Radiolabeled E series compounds were injected into the tail vein of SD rats aged 6-9 weeks (Hangzhou Ziyuan Testal Animal Technology Co., Ltd.) (about 7.4 MBq/mouse, specific activity: 84200.14 kBq/μg). At different time points (0.25, 0.5, 1, 2, 4, 6, 24, 48, 72 h) after administration of labeled compounds to SD rats, the animals were euthanized by carbon dioxide inhalation, and the blood and 16 viscera (blood, liver, spleen, lungs, heart, muscle, pancreas, testes) of the animals were collected after euthanasia.

Blood was collected through the abdominal aorta, and immediately after collection, 100 μL was quantified into a designated centrifuge tube (weighed). After the viscera were collected, they were washed twice with deionized water, wiped dry, put into a pre-weighed test tube, and weighed again. The weight of samples was calculated. The sample was measured on the day of collection. All blood samples and tissue samples were measured for radioactive counts using a gamma counter.

Figure 7:
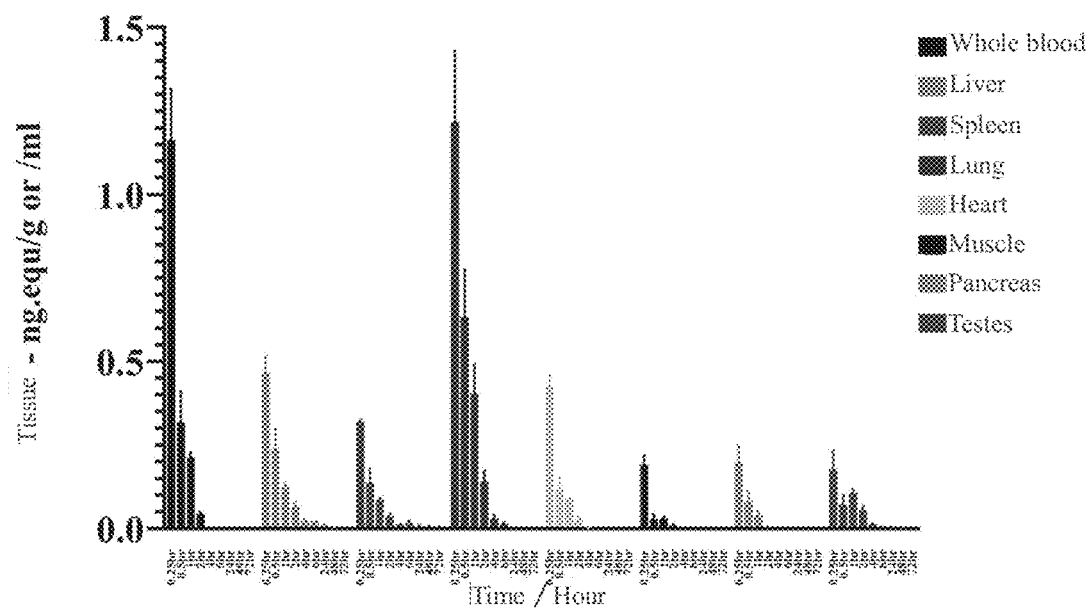
FIG. 7 shows the tissue distribution of $^{177}$Lu-E3 in various organs of normal SD rats in effect example 9.

The test results shown in FIG. 7 show that after intravenous administration, $^{177}$Lu-E3 can be rapidly distributed to various organs of healthy rats and then quickly washed out of the body; the main pathway of drug elimination is accomplished through the kidneys; the uptake of $^{177}$Lu-E3 in each organ is low, and shows good pharmacokinetic properties.

Tissue distribution in PSMA-positive tumor-bearing mice: About 6-9 weeks old (Nod scid) mice (Jiangsu Huajing Molecular Imaging and Drug Research Institute Co., Ltd.) were inoculated subcutaneously with 5×10$^6$ cells of 22rv1 (in 50% Matrigel, Corning) on the right shoulder of animals. When the tumor grew to a size of about 150-350 mm$^3$, $^{177}$Lu-E3 radiolabeled compound was injected into the tail vein of the mouse (about 7.4 MBq/mouse, specific activity: 22423.82 KBq/μg). The animals were euthanized by carbon dioxide inhalation at 0.25, 0.5, 1, 6, 24, 72, 144, and 168 hours respectively after administration. Blood and viscera (blood, liver, spleen, lung, heart, muscle, pancreas, testis, tumor) were collected from animals after euthanasia.

Figure 8:
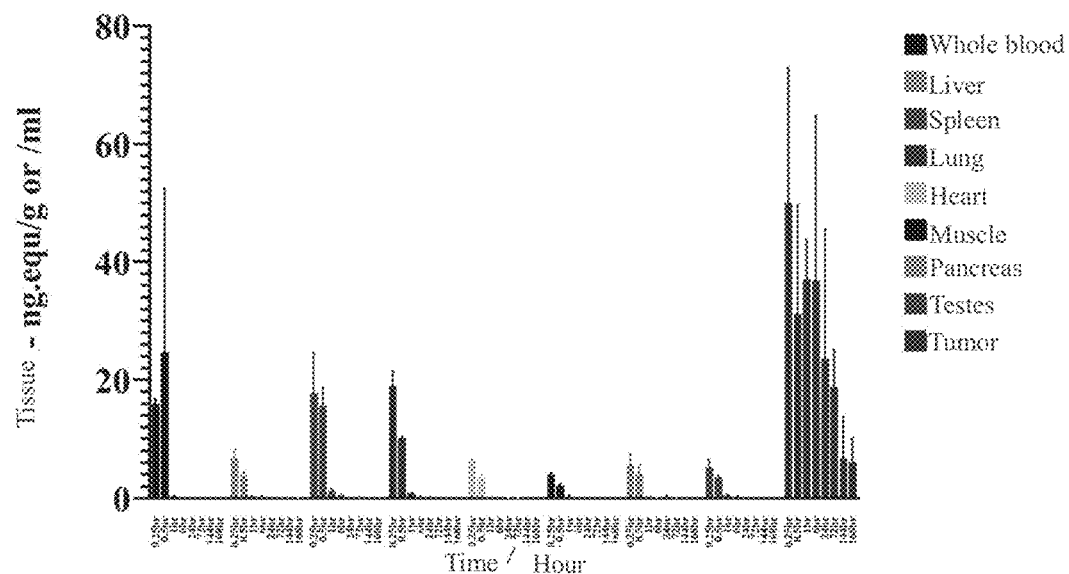
FIG. 8 shows the tissue distribution of $^{177}$Lu-E3 in various organs of 22RV1 tumor-bearing mice in effect example 9.

Blood was collected through the abdominal aorta, and immediately after collection, 100 μL was quantified into a designated centrifuge tube (weighed). After the viscera were collected, they were washed twice with deionized water and wiped dry. The viscera were put into a pre-weighed test tube, and weighed again. The weight of the sample was calculated. The sample was measured on the day of collection. All blood samples and tissue samples were measured for radioactive counts using a gamma counter, and the results are shown in FIG. 8.

After intravenous administration, $^{177}$Lu-E3 is quickly distributed to various organs of tumor-bearing mice. The clearance rate in the blood is relatively fast, and $^{177}$Lu-E3 was excreted through renal excretion. The uptake of $^{177}$Lu-E3 in the tumor reached the highest level 2 hours after administration, and then decreased over time. But even after 7 days, the tumor still contained a high drug concentration. In addition, the uptake in non-target organs is always low and was quickly washed out of the body.

Effect Example 10

Figure 9:
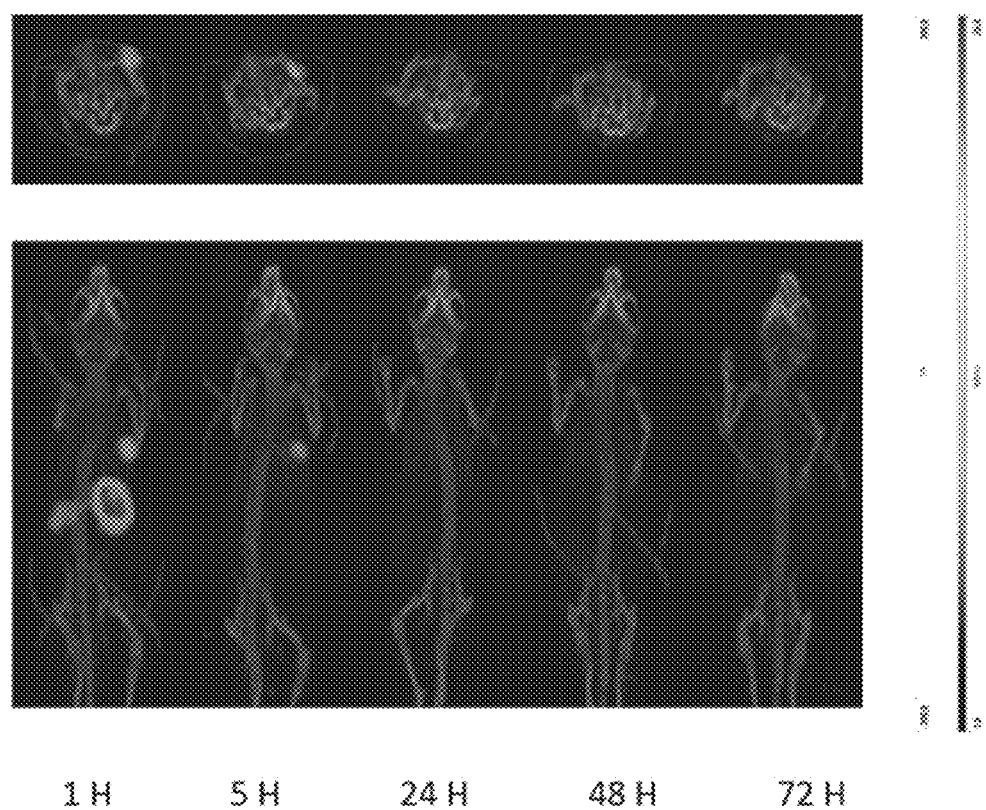
FIG. 9 shows the SPECT imaging of $^{177}$Lu-PSMA-617 of effect example 10.
Figure 10:
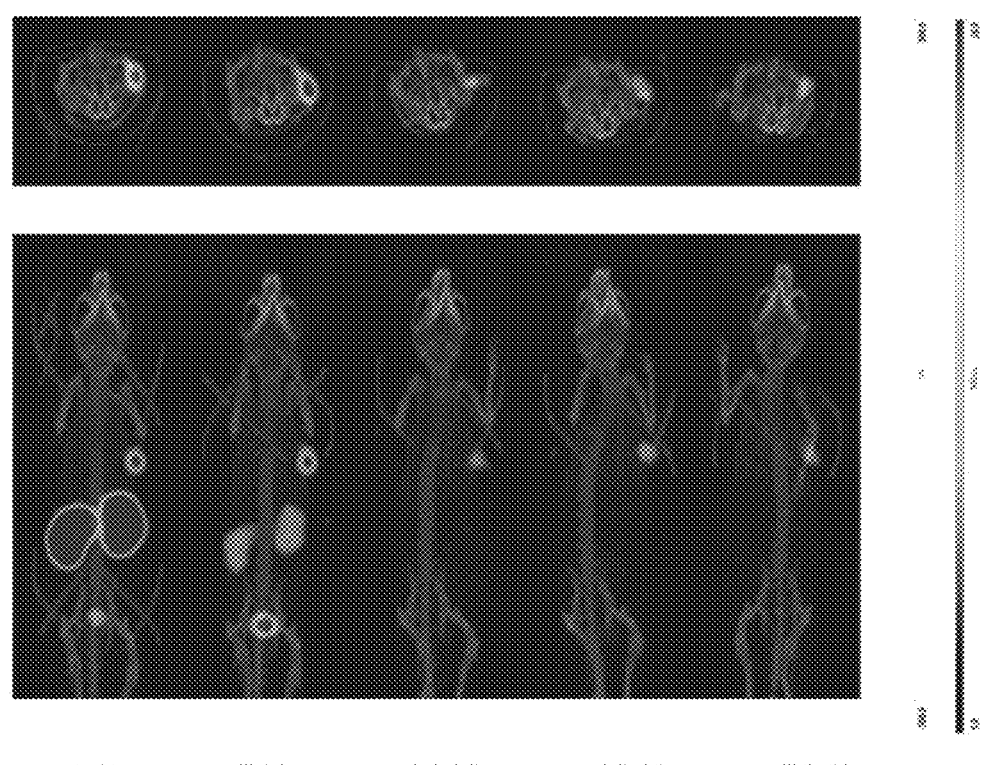
FIG. 10 shows the SPECT imaging of $^{177}$Lu-E3 of effect example 10.
Figure 11:
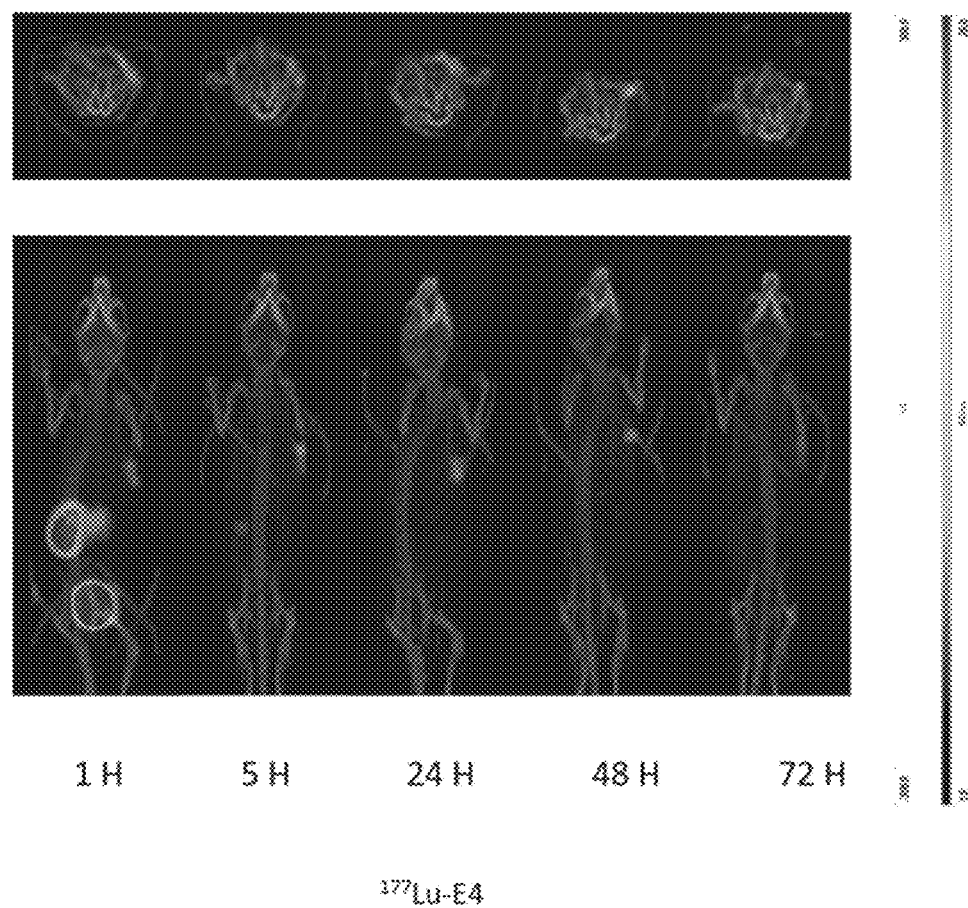
FIG. 11 shows the SPECT imaging of $^{177}$Lu-E4 of effect example 10.
Figure 12:
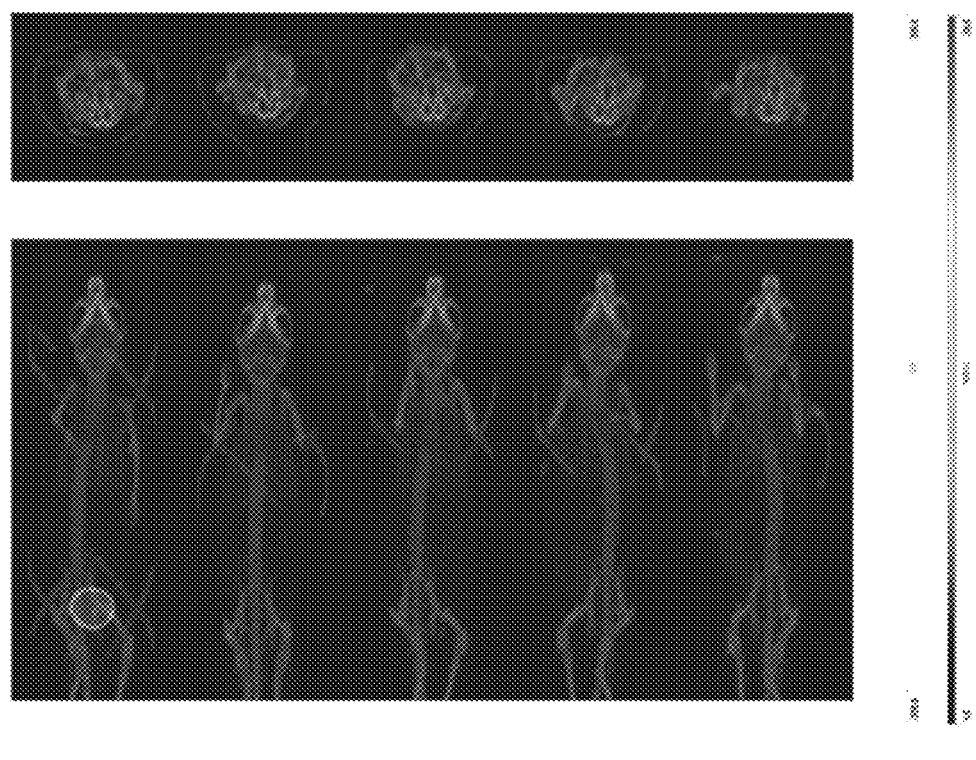
FIG. 12 shows the SPECT imaging of $^{177}$Lu-E8 of effect example 10.
Figure 13:
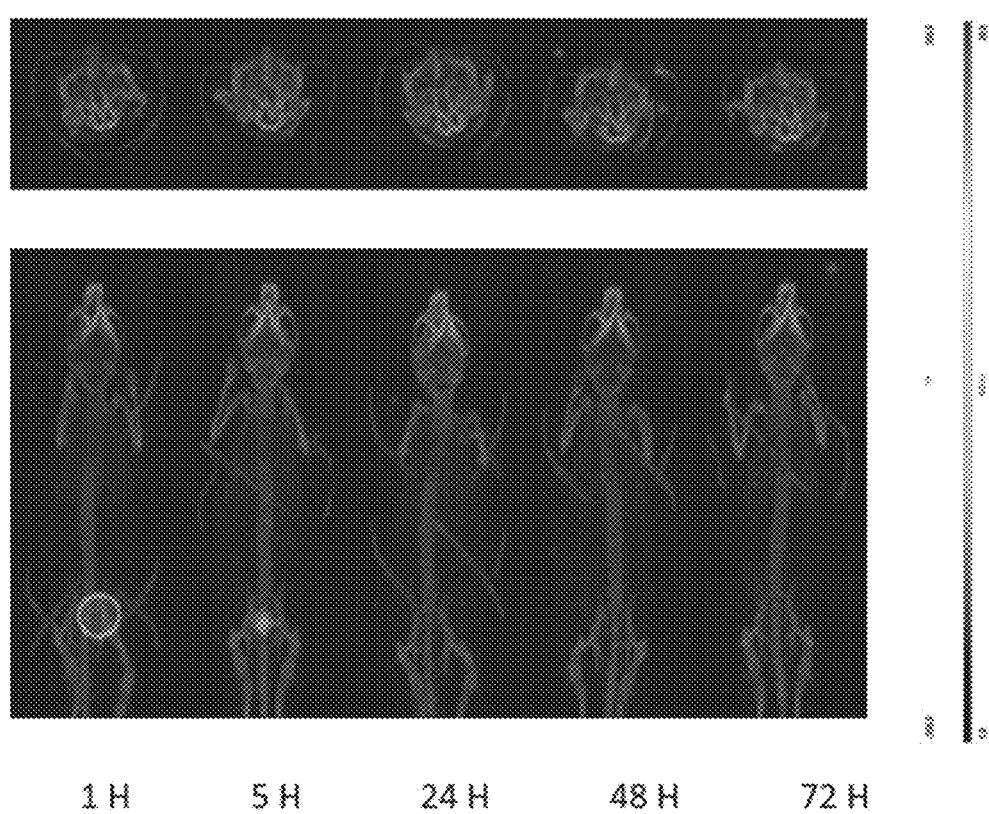
FIG. 13 shows the SPECT imaging of $^{177}$Lu-E16 of effect example 10.
Figure 14:
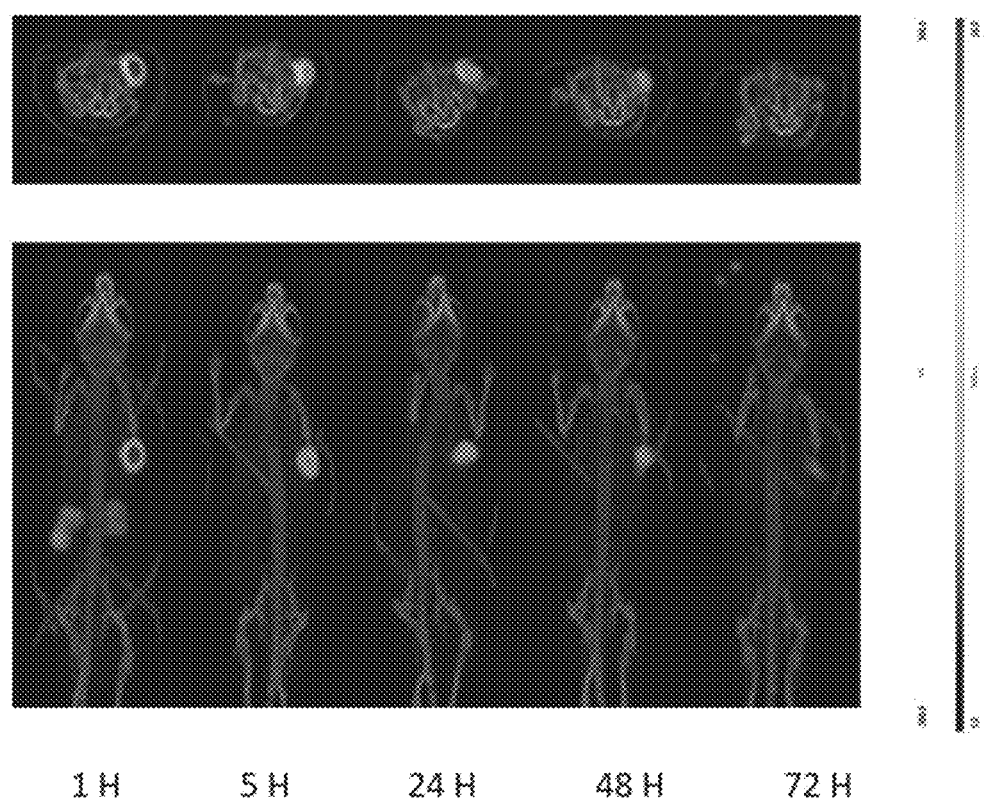
FIG. 14 shows the SPECT imaging of $^{177}$Lu-E18 of effect example 10.
Figure 15:
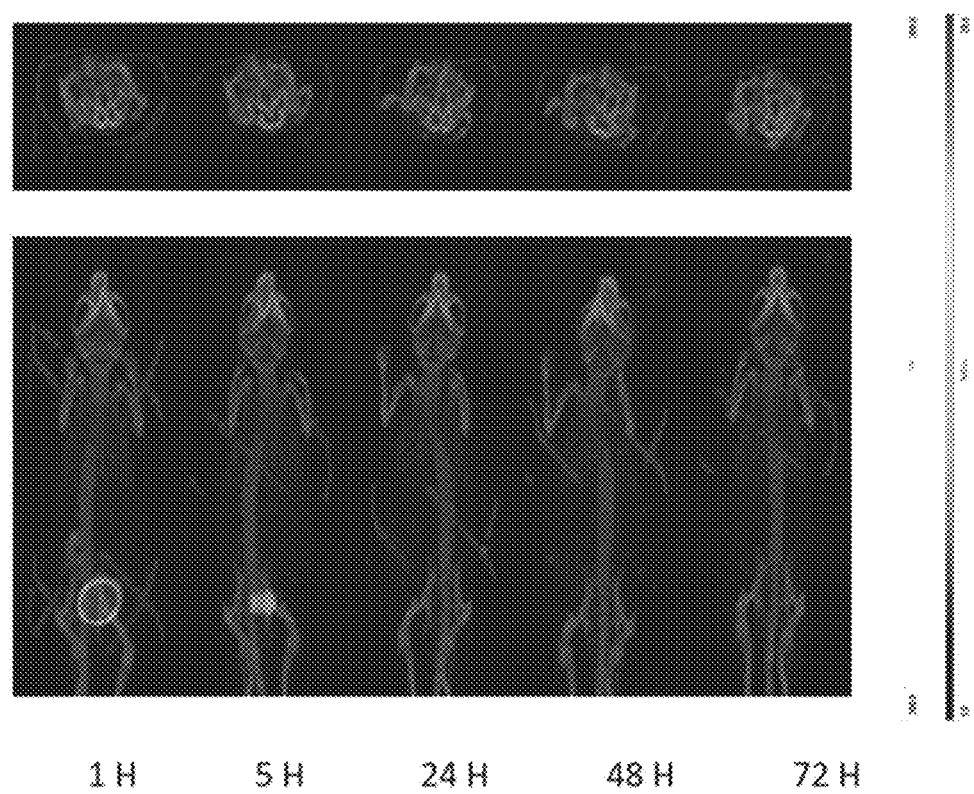
FIG. 15 shows the SPECT imaging of $^{177}$Lu-E24 of effect example 10.

About 4-5 weeks old (balb/c nude, Beijing Vital River) mice were subcutaneously inoculated with 5×10$^6$ cells of 22rv1 (in 50% Matrigel, Corning) on the right scapula of animals. When the tumor grew to a size of about 150-350 mm$^3$, after anesthesia with isoflurane, $^{177}$Lu-PSMA-617, $^{177}$Lu-E3, $^{177}$Lu-E4, $^{177}$Lu-E8, $^{177}$Lu-E16, $^{177}$Lu-E18, $^{177}$Lu-E24 radiolabeled compounds were injected into the tail vein of mice (about 7.4 MBq/mouse, specific activity: 22423.82 KBq/μg). Subsequently, SPECT imaging was performed with a small animal SPECT-CT imaging system (U-SPECT+/CT, MI Labs) at 1 h, 5 h, 24 h, 48 h and 72 h, respectively. $^{177}$Lu-PSMA-617 is shown in FIG. 9, $^{177}$Lu-E3 is shown in FIG. 10, $^{177}$Lu-E4 is shown in FIG. 11, $^{177}$Lu-E8 is shown in FIG. 12, $^{177}$Lu-E16 is shown in FIG. 13, $^{177}$Lu-E8 is shown in FIG. 14, and $^{177}$Lu-E24 is shown in FIG. 15. The results of imaging tests show that after these $^{177}$Lu-labeled E compounds enter the animal body through the tail vein of the animal, they can be quickly distributed to various organs of the animal and then quickly washed out of the body. The main way of drug elimination is through the kidney. The residence time of $^{177}$Lu-E8, $^{177}$Lu-E16, and $^{177}$Lu-E24 in both of animals and tumors expressing PSMA is relatively short, and these compounds are basically washed out of body after 1 hour. Comparing with $^{177}$Lu-PSMA-617, $^{177}$Lu-E3, $^{177}$Lu-E4, and $^{177}$Lu-E8 can also be rapidly excreted from animal body, the PSMA-expressing tumors contain higher uptake of radioactivity while the rest organs show radioactivity as the same as that in background. $^{177}$Lu-E3 and $^{177}$Lu-E18 still show high specific absorption in PSMA-expressing tumors even after 72 hours.

Effect Example 11

Figure 16:
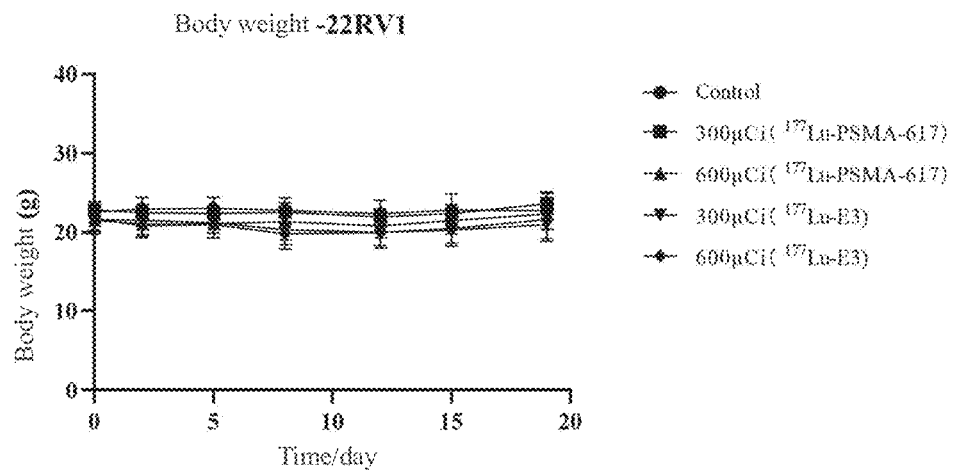
FIG. 16 shows the body weight changes of animals in the pharmacodynamic study of $^{177}$Lu-E3 in effect example 11.
Figure 17:
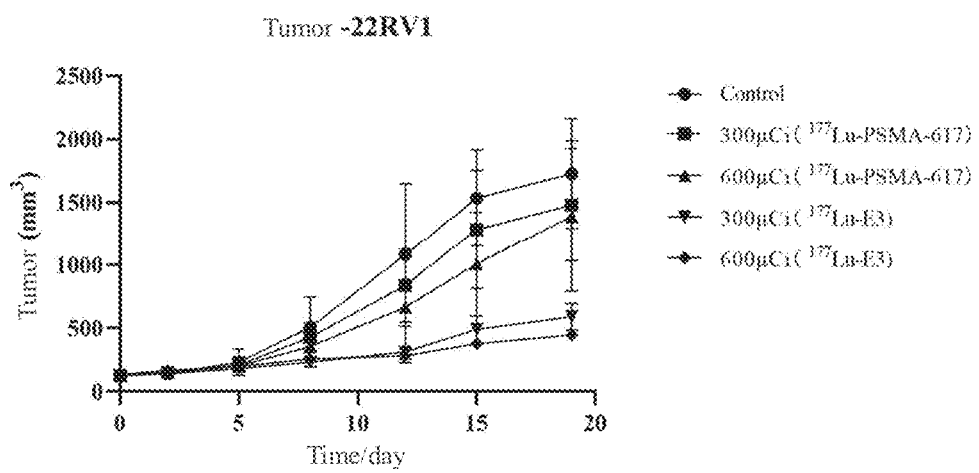
FIG. 17 shows the changes in tumor size in the pharmacodynamic study of $^{177}$Lu-E3 in effect example 11.

About 4-5 weeks (nod scid, Jiangsu Huajing Molecular Imaging and Drug Research Institute Co., Ltd.) mice were inoculated subcutaneously with 1×10$^6$ cells of 22rv1 (in 50% Matrigel, Corning) on the right scapula of animals. When the tumor grew to the size required by the test, the animals were randomly assigned to 5 test groups according to the tumor volume, with 7 animals in each group, and the body weight and tumor size of the animals were measured. On the day of grouping, the control group (normal saline), group 1 ($^{177}$Lu-PSMA-617 300 mCi/animal), group 2 ($^{177}$Lu-PSMA-617 600 mCi/animal), group 3 ($^{177}$Lu-E3 300 mCi/animal), and group 4 ($^{177}$Lu-E3 600 mCi/animal) began to be administered. General health and appearance observations were carried out every day after the start of the test, and the body weight and tumor size of animals were measured before each sample sampling time point. Any unusual observations discovered throughout the study period will be recorded in the raw data. The results of animal weight changes were shown in FIG. 16, and the results of tumor size changes are shown in FIG. 17 and Table 13.

| Group | Test sample | Tumor volume (mm$^3$)$^a$ | | TGI$_{TV}$ (%) | P$^b$ |
| | | Before administration | Administration in groups Day 19 | | |
|---|---|---|---|---|---|
| G1 | Control | 126.09 ± 29.31 | 1,727.18 ± 435.06 | — | — |
| G2 | 300 μCi (PSMA-617) | 126.96 ± 29.56 | 1,480.09 ± 446.83 | 15.49% | 0.3547 |
| G3 | 600 μCi (PSMA-617) | 127.86 ± 29.25 | 1,389.81 ± 598.96 | 21.18% | 0.2904 |
| G4 | 300 μCi (E3) | 126.41 ± 26.77 | 590.66 ± 103.97 | 71.00% | <0.0001 |
| G5 | 600 μCi (E3) | 133.60 ± 35.46 | 447.12 ± 47.84 | 80.42% | <0.0001 |

Note:

$^a$Mean ± standard error;

$^b$Statistical comparison between the tumor volumes of the administration group and the control group on the 19th day after administration in groups, T-test.

The relative tumor inhibition rate is represented by $TGI_{TV}$ (%)=$[1-(T_i-T_0)/(V_i-V_0)]\times 100\%$ ($T_i$: the mean tumor volume of the treatment group on the i-th day of administration, $T_0$: the mean tumor volume of the treatment group on the 0th day of administration; $V_i$: the mean tumor volume of the vehicle control group on the i-th day of administration, $V_0$: the mean tumor volume of the vehicle control group on the 0th day of administration.

The test results show that the efficacy of $^{177}$Lu-E3 in the mouse xenograft tumor model is significantly improved. Comparing with 15-21% of the tumor inhibition rate of $^{177}$Lu-PSMA-617, the tumor growth inhibition rate of $^{177}$Lu-E3 reaches 71-80%. Moreover, the two dosing groups of animals treated with $^{177}$Lu-E3 show no significant difference in the inhibitory effect on tumor growth within the first 10 days after medication. Then it gradually shows the dose-related efficacy difference. The analysis of the overall data of $^{177}$Lu-E3 in the two dose groups shows statistically significant. The results of this experiment demonstrate that $^{177}$Lu-E3 has a better inhibitory effect on the growth of tumors expressing PSMA than $^{177}$Lu-PSMA-617 at the same dose. The efficient inhibitory effect can reduce the drug dose when it is used, which not only can reduce the potential radiation-related drug toxicity, also can reduce drug costs.

Finally, the above-mentioned general description and specific implementation examples have described the present disclosure in detail. Through these descriptions, those skilled in the art can obviously make some modifications or improvements to the present disclosure on the basis of the present disclosure. Therefore, any modification or improvement made without departing from the spirit of the present disclosure belongs to the protection scope of the present disclosure.

What is claimed is:

1. A peptide-urea derivative of formula I, or a pharmaceutically acceptable salt thereof,

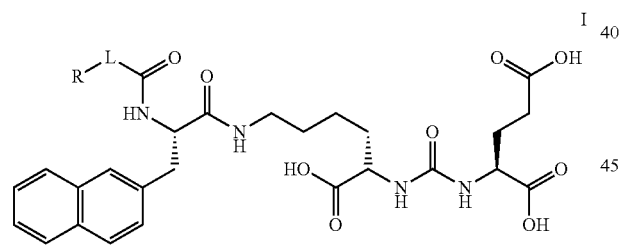

wherein:
L is

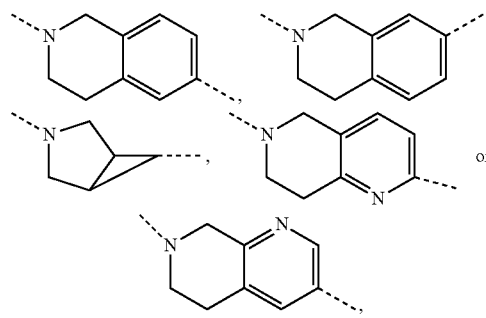

wherein the N atom is linked to R;

R is a group containing a radioactive metal ion, which is composed of a radioactive metal ion and a group with the function of chelating a metal ion, wherein the radioactive metal ion is chelated with the group with the function of chelating a metal ion, and the group with the function of chelating a metal ion is

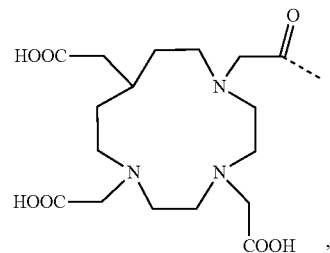

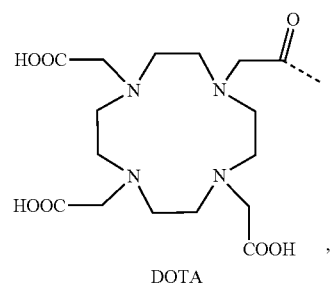
DOTA

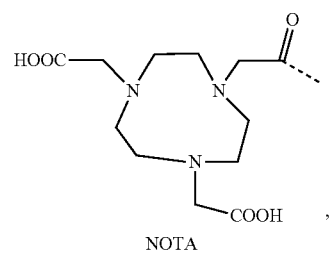
NOTA

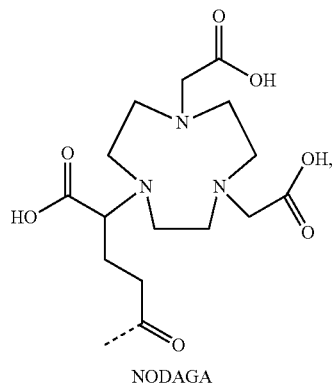
NODAGA

-continued

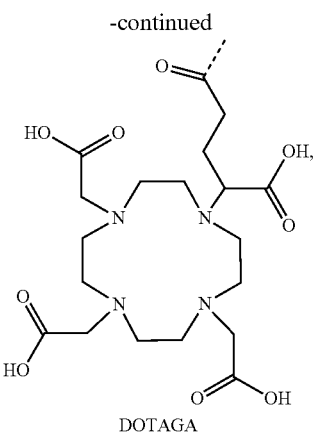
DOTAGA

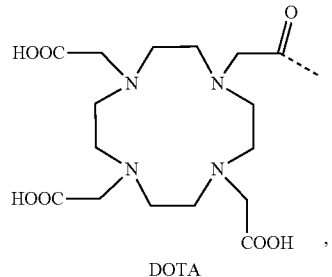
PCTA , or

AAZTA

2. The peptide-urea derivative of formula I according to claim 1, or a pharmaceutically acceptable salt thereof, characterized by meeting one or more of the following conditions:

(31) the radioactive metal ion is a radioactive metal ion releasing α, β or γ rays;

(33) the radioactive metal ion has one or more of the following effects: 1. tracking; 2. delivery; 3. imaging; 4. treatment.

3. The peptide-urea derivative of formula I according to claim 2, or a pharmaceutically acceptable salt thereof, characterized by meeting one or more of the following conditions:

(32) the radioactive metal ion has one or more of the following effects: 1. PET imaging; 2. SPECT imaging; 3. radiation treatment.

4. The peptide-urea derivative of formula I according to claim 2, or a pharmaceutically acceptable salt thereof, characterized by meeting one or more of the following conditions:

(4) the radioactive metal ion is $^{68}$Ga, $^{89}$Zr, $^{64}$Cu, $^{86}$Y, $^{99m}$Tc, $^{111}$In, $^{90}$Y, $^{67}$Ga, $^{177}$Lu, $^{211}$At, $^{153}$Sm, $^{186}$Re, $^{188}$Re, $^{67}$Cu, $^{212}$Pb, $^{225}$Ac, $^{213}$Bi, $^{223}$Ra, $^{212}$Bi or $^{212}$Pb.

5. The peptide-urea derivative of formula I according to claim 4, or a pharmaceutically acceptable salt thereof, characterized by meeting one or more of the following conditions:

(3) the group with the function of chelating a metal ion is

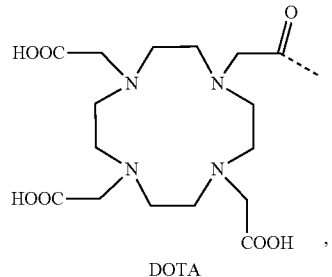
DOTA ,

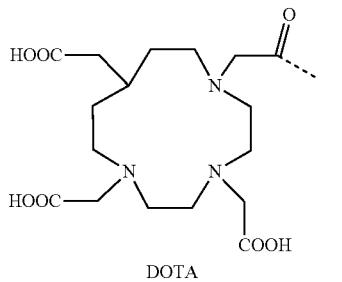
DOTA or

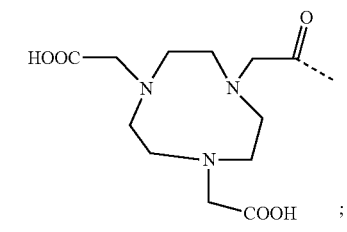
NOTA ;

(4) the radioactive metal ion is $^{68}$Ga$^{3+}$, $^{89}$Zr$^{4+}$, $^{64}$Cu$^{2+}$, $^{86}$Y$^{3+}$, $^{99m}$Tc$^{4+}$, $^{111}$In$^{3+}$, $^{90}$Y, $^{67}$Ga$^{3+}$, $^{177}$Lu$^{3+}$, $^{211}$At, $^{153}$Sm, $^{186}$Re, $^{188}$Re, $^{67}$Cu$^{2+}$, $^{212}$Pb$^{2+}$, $^{225}$Ac$^{3+}$, $^{213}$Bi$^{3+}$, $^{223}$Ra, $^{212}$Bi or $^{212}$Pb$^{2+}$.

6. The peptide-urea derivative of formula I according to claim 1, or a pharmaceutically acceptable salt thereof, characterized in that the peptide-urea derivative of formula I is a compound formed by chelation of compound A and $^{68}$Ga$^{3+}$, wherein the structure of compound A is as shown in any of the following structures:

123 124
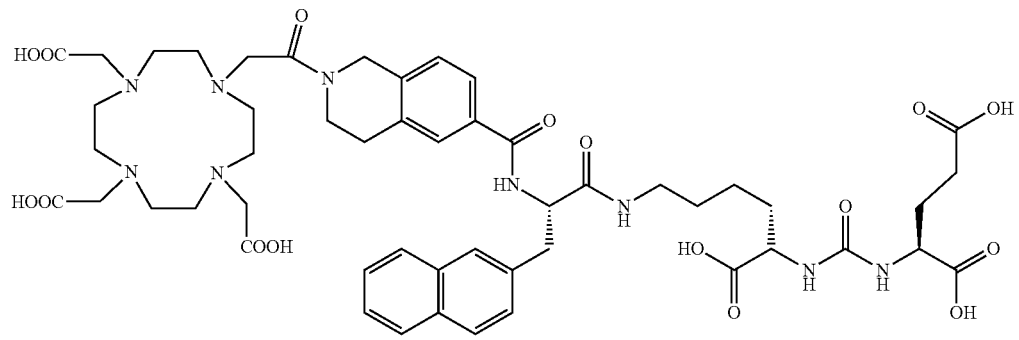
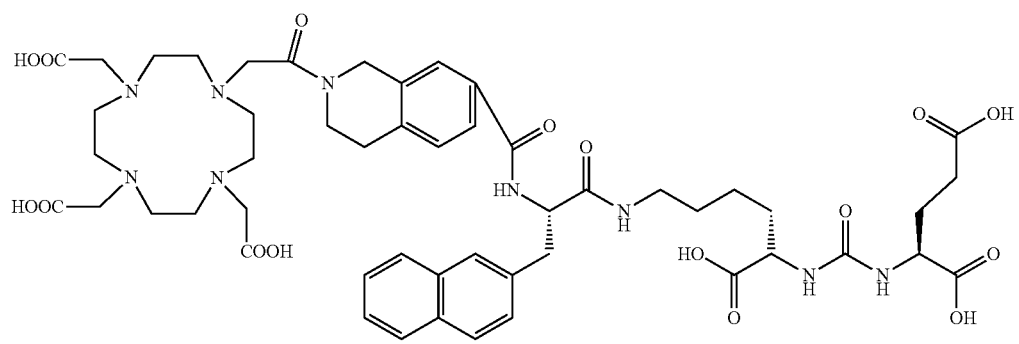
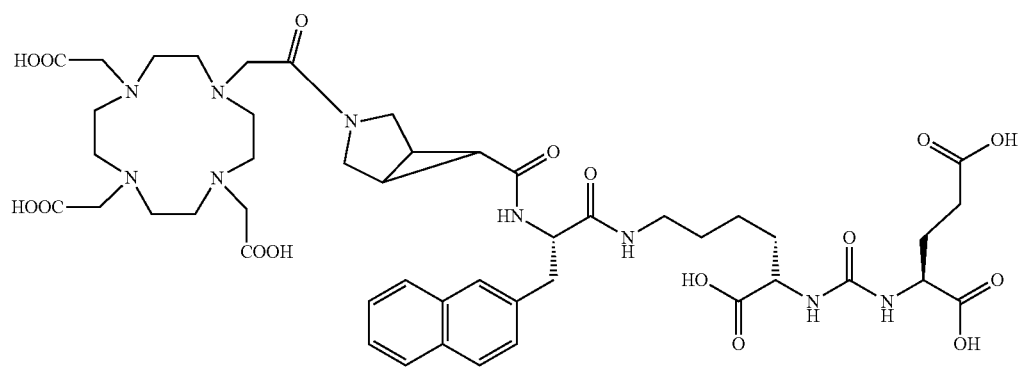
E16
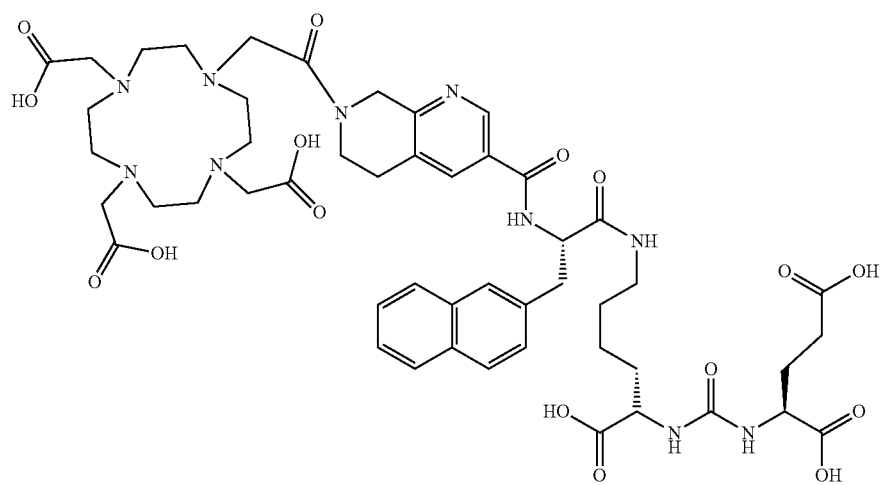

E17
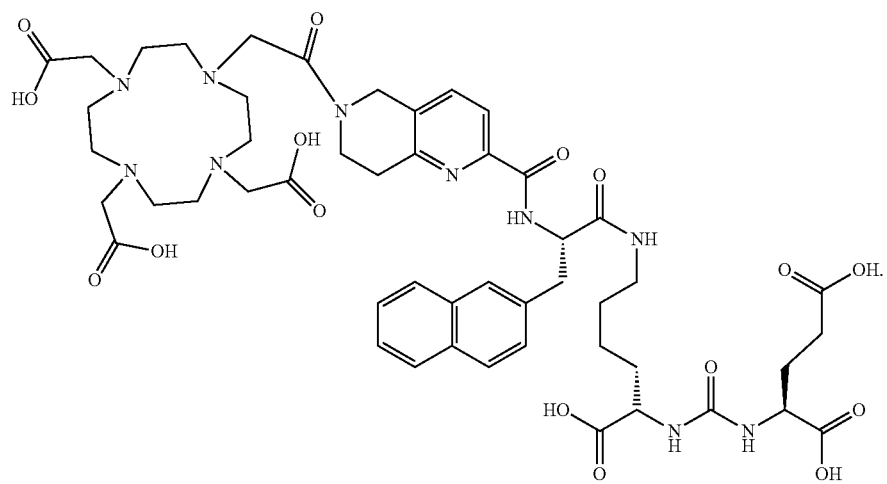
7. The peptide-urea derivative of formula I according to claim 1, or a pharmaceutically acceptable salt thereof, characterized in that the peptide-urea derivative of formula I is a compound formed by chelation of compound A and $^{177}Lu^{3+}$, wherein the structure of compound A is as shown in any of the following structures:
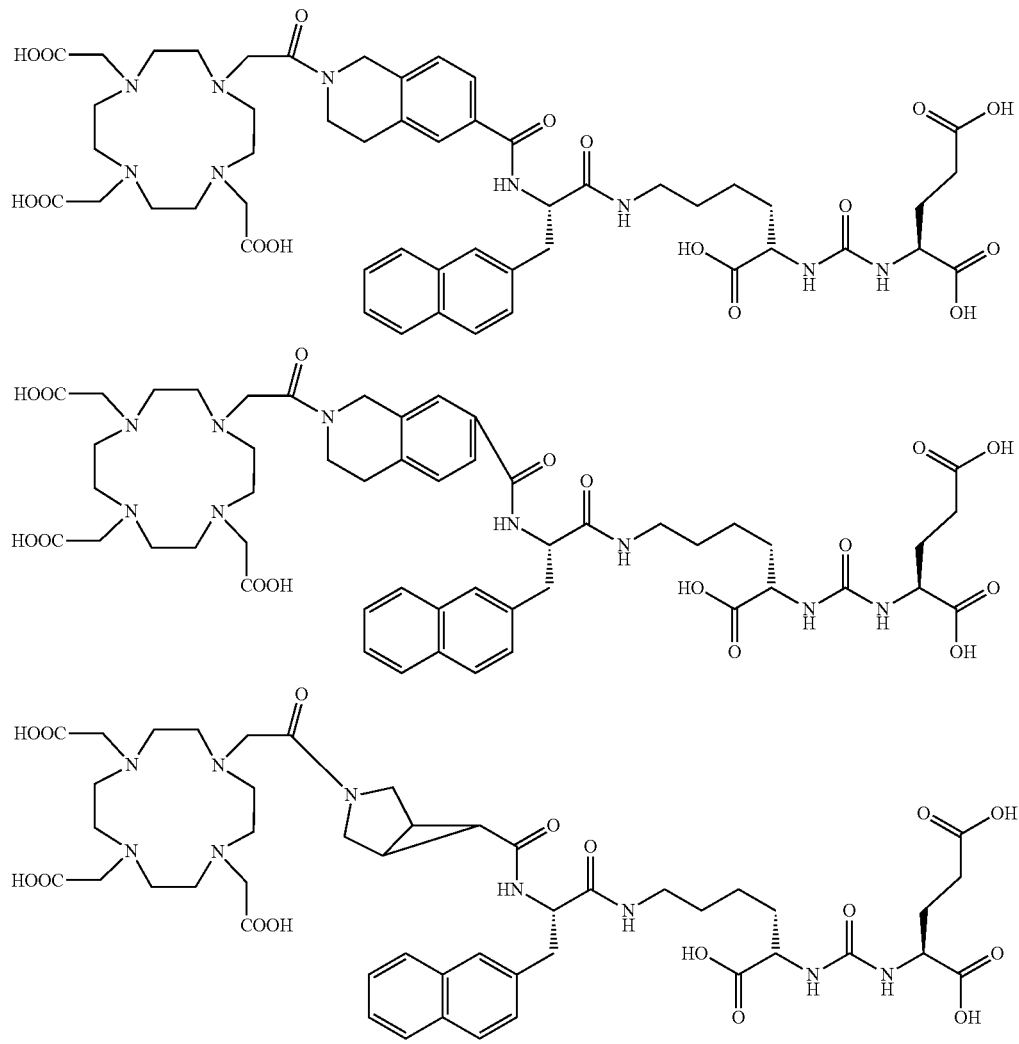

E16
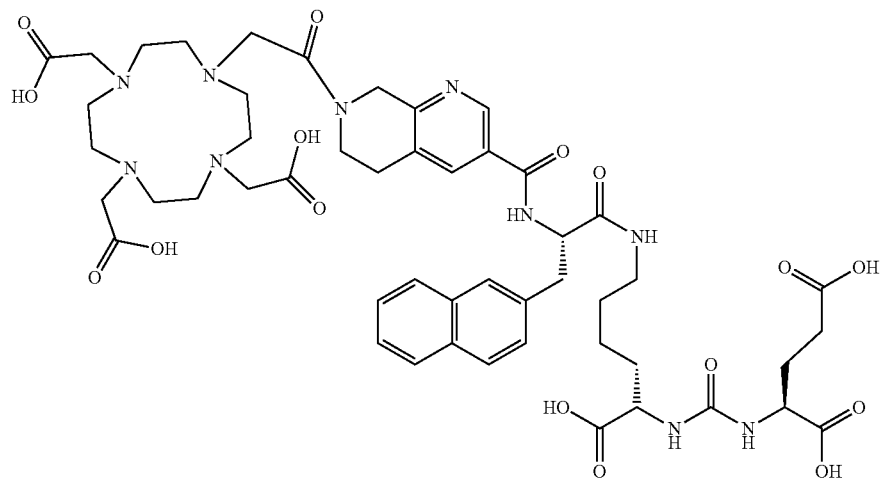
E17
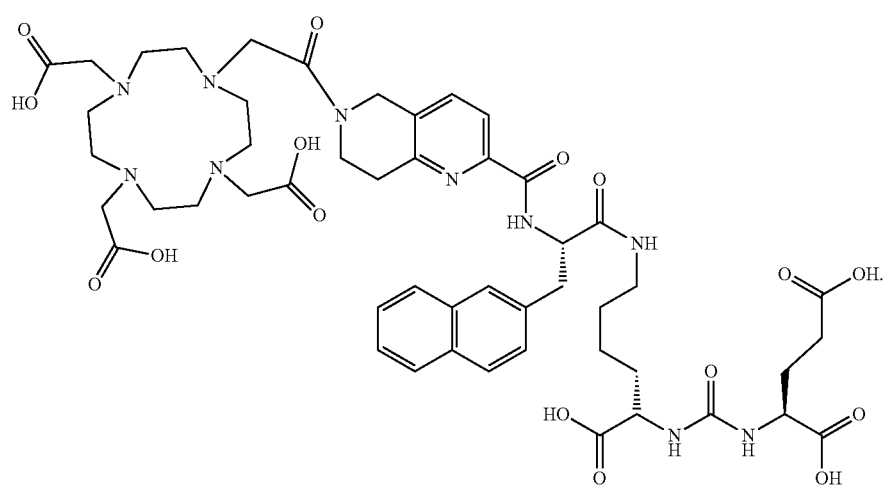
8. The peptide-urea derivative of formula I according to claim 1, or a pharmaceutically acceptable salt thereof, characterized in that the structure of the peptide-urea derivative of formula I is as shown in the following structures:
177Lu-E3
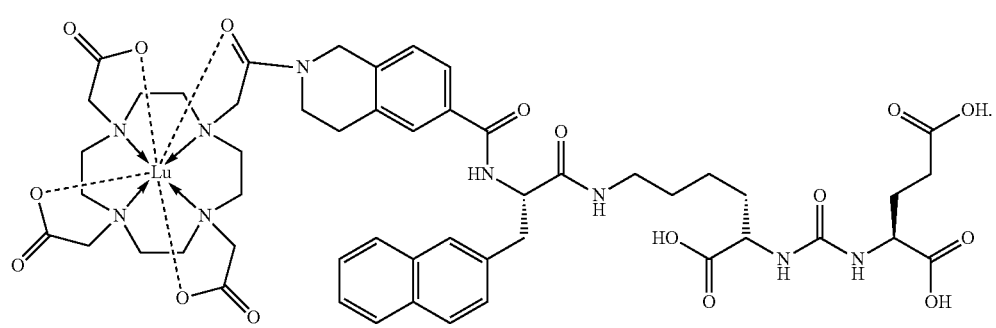

9. A pharmaceutical composition, which comprises substance X and pharmaceutical adjuvant; wherein the substance X is the peptide-urea derivative of formula I according to claim 1, or a pharmaceutically acceptable salt thereof.

10. The pharmaceutical composition according to claim 9, wherein the pharmaceutical adjuvant is selected from one or more of DTPA, ascorbic acid, sodium ascorbate and water.

11. A pharmaceutical composition, which comprises substance X and pharmaceutical adjuvant; wherein the substance X is the peptide-urea derivative of formula I according to claim 6, or a pharmaceutically acceptable salt thereof.

12. The pharmaceutical composition according to claim 11, wherein the pharmaceutical adjuvant is selected from one or more of DTPA, ascorbic acid, sodium ascorbate and water.

13. A pharmaceutical composition, which comprises substance X and pharmaceutical adjuvant; wherein the substance X is the peptide-urea derivative of formula I according to claim 7, or a pharmaceutically acceptable salt thereof.

14. The pharmaceutical composition according to claim 13, wherein the pharmaceutical adjuvant is selected from one or more of DTPA, ascorbic acid, sodium ascorbate and water.

15. A pharmaceutical composition, which comprises substance X and pharmaceutical adjuvant; wherein the substance X is the peptide-urea derivative of formula I according to claim 8, or a pharmaceutically acceptable salt thereof.

16. The pharmaceutical composition according to claim 15, wherein the pharmaceutical adjuvant is selected from one or more of DTPA, ascorbic acid, sodium ascorbate and water.

\* \* \* \* \*